United States Patent
Martinez et al.

(10) Patent No.: US 11,886,244 B2
(45) Date of Patent: Jan. 30, 2024

(54) WEARABLE ELECTRONIC BELT DEVICE

(71) Applicant: Modjoul, Inc., Clemson, SC (US)

(72) Inventors: R. Eric Martinez, Mercer Island, WA (US); Goutam Koley, Anderson, SC (US); Kapil Chalil Madathil, Clemson, SC (US)

(73) Assignee: Modjoul, Inc., Clemson, SC (US)

( * ) Notice: Subject to any disclaimer, the term of this patent is extended or adjusted under 35 U.S.C. 154(b) by 416 days.

(21) Appl. No.: 16/673,670

(22) Filed: Nov. 4, 2019

(65) Prior Publication Data

US 2020/0174517 A1   Jun. 4, 2020

Related U.S. Application Data

(63) Continuation of application No. PCT/US2018/031062, filed on May 4, 2018.
(Continued)

(51) Int. Cl.
    *G01L 1/00* (2006.01)
    *G06F 1/16* (2006.01)
    (Continued)

(52) U.S. Cl.
    CPC .............. *G06F 1/163* (2013.01); *G01L 1/005* (2013.01); *G01S 19/01* (2013.01);
    (Continued)

(58) Field of Classification Search
    CPC .............. G06F 1/163; G06Q 10/0635; G06Q 10/0637; G06Q 10/06398; G01L 1/005; H04W 4/80
    See application file for complete search history.

(56) References Cited

U.S. PATENT DOCUMENTS

| 2010/0312297 | A1 | 12/2010 | Volpe et al. |
| 2011/0090079 | A1 | 4/2011 | Morino et al. |

(Continued)

FOREIGN PATENT DOCUMENTS

| CN | 205041401 U | 2/2016 |
| CN | 103550921 A8 | 1/2017 |

(Continued)

OTHER PUBLICATIONS

McGrew et al., "Datagram Transport Layer Security (DTLS) Extension to Establish Keys for the Secure Real-time Transport Protocol (SRTP)," IETF Trust, Internet Engineering Task Force (IETF) Request for Comments: 5764, May 2010, 26 pages.

(Continued)

*Primary Examiner* — Anthony M Haughton
(74) *Attorney, Agent, or Firm* — Davis Wright Tremaine LLP

(57) ABSTRACT

A belt wearable by a human subject includes a variety of sensors that collect information about the wearer, the wearer's environment, and the wearer's movements. A communication interface on the belt allows sensor data collected by the belt to be transferred to a storage server. In some examples, the communication interface is a Wi-Fi interface, a cellular interface, or a removable memory interface. The data is processed to identify activities performed by the wearer such as walking, driving, and working at heights. In some examples, events such as aggressive driving events, slips and falls, and unsafe lifting are detected. In some examples, this information is used to generate reports that allow an employer to manage the productivity and safety of a workforce.

4 Claims, 51 Drawing Sheets

Related U.S. Application Data

(60) Provisional application No. 62/501,558, filed on May 4, 2017.

(51) Int. Cl.

| | |
|---|---|
| *H04W 4/80* | (2018.01) |
| *G01S 19/01* | (2010.01) |
| *G06Q 10/0635* | (2023.01) |
| *G06Q 10/0637* | (2023.01) |
| *G06Q 10/0639* | (2023.01) |
| *H04R 1/02* | (2006.01) |
| *H04W 64/00* | (2009.01) |

(52) U.S. Cl.
CPC ..... *G06Q 10/0635* (2013.01); *G06Q 10/0637* (2013.01); *G06Q 10/06398* (2013.01); *H04R 1/028* (2013.01); *H04W 4/80* (2018.02); *H04W 64/00* (2013.01)

(56) References Cited

U.S. PATENT DOCUMENTS

| | | | |
|---|---|---|---|
| 2013/0314210 A1* | 11/2013 | Schoner | G08B 13/2485 340/8.1 |
| 2015/0161377 A1 | 6/2015 | Rodzevski et al. | |
| 2015/0289822 A1 | 10/2015 | Dugan | |
| 2017/0222676 A1 | 8/2017 | Piccioni | |
| 2017/0245806 A1* | 8/2017 | Elhawary | A61B 5/681 |
| 2017/0347965 A1* | 12/2017 | Elhawary | A61B 5/6824 |

FOREIGN PATENT DOCUMENTS

| | | |
|---|---|---|
| EP | 2520472 A2 | 11/2012 |
| TW | 201413630 A | 4/2014 |
| TW | 201644255 A | 12/2016 |
| WO | 2016126639 A1 | 8/2016 |

OTHER PUBLICATIONS

Medvinsky et al., "Addition of Kerberos Cipher Suites to Transport Layer Security (TLS)," Request for Comments 2712, Standards Track, Oct. 1999, 7 pages.
Merkle et al., "Elliptic Curve Cryptography (ECC) Brainpool Curves for Transport Layer Security (TLS)," IETF Trust, Internet Engineering Task Force (IETF) Request for Comments: 7027, Category: Informational, Oct. 2013, 10 pages.
Metzger et al., "IP Authentication Using Keyed MD5," Request for Comments: 1828, Standards Track, Aug. 1995, 6 pages.
Moriai et al., "Addition of Camellia Cipher Suites to Transport Layer Security (TLS)," Request for Comments: 4132, Standards Track, Jul. 2005, 7 pages.
Newman, "Using TLS with IMAP, POP3 and ACAP," Request for Comments: 2595, Standards Track, Jun. 1999, 15 pages.
Orman, "The OAKLEY Key Determination Protocol," Request for Comments: 2412, Informational, Nov. 1998, 56 pages.
Phelan et al., "Datagram Transport Layer Security (DTLS) over the Datagram Congestion Control Protovol (DCCP)," Network Working Group Request for Comments: 5238, Category: Standards Track, May 2008, 10 pages.
Rescorla et al., "Datagram Transport Layer Security Version 1.2," IETF Trust, Internet Engineering Task Force (IETF) Request for Comments: 6347, Category: Standards Track, Jan. 2012, 32 pages.
Rescorla et al., "Datagram Transport Layer Security," Request for Comments: 4347, Standards Track, Apr. 2006, 25 pages.
Rescorla et al., "HTTP Over TLS," The Internet Society, Network Working Group Request for Comments: 2818, Category: Informational, May 2000, 7 pages.
Rescorla et al., "TLS Elliptic Curve Cipher Suites with SHA-256/384 and AES Galois Counter Mode (GCM)," Network Working Group Request for Comments: 5289, Category: Informational, Aug. 2008, 6 pages.
Rescorla et al., "Transport Layer Security (TLS) Renegotiation Indication Extension," IETF Trust, Internet Engineering Task Force (IETF) Request for Comments: 5746, Category: Standards Track, Feb. 2010, 15 pages.
Salowey et al., "AES Galois Counter Mode (GCM) Cipher Suites for TLS," Network Working Group Request for Comments: 5288, Category: Standards Track, Aug. 2008, 8 pages.
Salowey et al., "Transport Layer Security (TLS) Session Resumption without Server-Side State," Request for Comments: 5077, Standards Track, Jan. 2008, 20 pages.
Salter et al., "Suite B Profil for Transport Layer Security (TLS)," IETF Trust, Internet Engineering Task Force (IETF) Request for Comments: 6460, Category: Informational, Jan. 2012, 14 pages.
Santesson et al., "TLS User Mapping Extension," Request for Comments: 4681, Standards Track, Oct. 2006, 11 pages.
Santesson, "TLS Handshake Message for Supplemental Data," Request for Comments: 4680, Standards Track, Sep. 2006, 10 pages.
Schlyter, J., and W. Griffin, "Using DNS to Securely Publish Secure Shell (SSH) Key Fingerprints," Request for Comments: 4255, Standards Track, Jan. 2006, 9 pages.
Stebiula, D., and J. Green, "Elliptic Curve Algorithm Integration in the Secure Shell Transport Layer," Request for Comments: 5656, Standards Track, Dec. 2009, 19 pages.
Sury, O., "Use of the SHA-256 Algorithm With RSA, Digital Signature Algorithm (DSA), and Elliptic Curve DSA (ECDSA) in SSHFP Resource Records," Request for Comments: 6594, Standards Track, Apr. 2012, 9 pages.
Taylor et al., "Using the Secure Remote Password (SRP) Protocol for TLS Authentication," Network Working Group Request for Comments: 5054, Category: Informational, Nov. 2007, 24 pages.
Tibshirani, "A proposal for variable selection in the Cox model," Depailment of Preventive Medicine and Biostatistics and Department of Statistics University of Toronto, Apr. 13, 1994, 12 pages.
Tuexen et al., "Datagram Transport Layer Security (DTLS) for Stream Control Transmission Protocol (SCTP)," IETF Trust, Internet Engineering Task Force (IETF) Request for Comments: 6083, Category: Standards Track, Jan. 2011, 9 pages.
Turner et al., "Prohibiting Secure Sockets Layer (SSL) Version 2.0," IETF Trust, Internet Engineering Task Force (IETF) Request for Comments: 6176, Mar. 2011, 4 pages.
Ylonen, T., and C. Lonvick, "The Secure Shell (SSH) Authenication Protocol," Request for Comments: 4252, Standards Track, Jan. 2006, 16 pages.
Ylonen, T., and C. Lonvick, "The Secure Shell (SSH) Connection Protocol," Request for Comments: 4254, Standards Track, Jan. 2006, 23 pages.
Ylonen, T., and C. Lonvick, "The Secure Shell (SSH) Protocol Architecture," Request for Comments: 4251, Standards Track, Jan. 2006, 28 pages.
Ylonen, T., and C. Lonvick, "The Secure Shell (SSH) Transport Layer Protocol," Request for Comments: 4253, Standards Track, Jan. 2006, 30 pages.
Atkinson, "IP Authentication Header," Request for Comments: 1826, Standards Track, Aug. 1995, 14 pages.
Atkinson, R., "IP Encapsulating Security Payload (ESP)," Request for Comments: 1827, Standards Track, Aug. 1995, 13 pages.
Atkinson, R., "Security Architecture for the Internet Protocol," Request for Comments: 1825, Standards Track, Aug. 1995, 23 pages.
Bellare, M., et al., "The Secure Shell (SSH) Transport Layer Encryption Modes," Request for Comments: 4344, Standards Track, Jan. 2006, 12 pages.
Bider, D., and M. Baushke, "SHA-2 Data Integrity Verification for the Secure Shell (SSH) Transport Layer Protocol," Request for Comments: 6668, Standards Track, Jul. 2012, 6 pages.
Blake-Wilson et al., "Elliptic Curve Cryptogtraphy (ECC) Cipher Suites for Transport Layer Security (TLS)," The Internet Society, Network Working Group Request for Comments: 4492, Category: Informational, May 2006, pp. 1-35.
Blake-Wilson et al., "Transport Later Security (TLS) Extensions," The Internet Society, Network Working Group Request for Comments: 4366, Category: Standards Track, Apr. 2006, pp. 1-30.

(56) References Cited

OTHER PUBLICATIONS

Blake-Wilson et al., "Transport Layer Security (TLS) Extensions," Request for Comments: 3546, Standards Track, Jun. 2003, 28 pages.
Blumenthal et al., "Pre-Shared Key (PSK) Ciphersuites with NULL Encryption for Transport Layer Security (TLS)," Request for Comments: 4785, Standards Track, Jan. 2007, 5 pages.
Brown et al., "Transport Layer Security (TLS) Authorization Extensions," Internet Engineering Task Force (IETF) Request for Comments: 5878, Cateogry: Experimental, May 2010, 19 pages.
Chown et al., "Advanced Ecryption Standard (AES) Ciphersuites for Transport Layer Security (TLS)," The Internet Society, Network Working Group Request for Comments: 3268, Category: Standards Track, Jun. 2002, 7 pages.
Cohn et al., "MQTT Version 3.1.1," Oasis, ISO/IEC 20922, Oct. 29, 2014, 81 pages.
Cusack, F., and M. Forssen, "Generic Message Exchange Authenticatioin for the Secure Shell Protocol (SSH)," Request for Comments: 4256, Standards Track, Jan. 2006, 12 pages.
Dang, "Recommendation for Applications Using Approved Hash Algorithms" NIST Special Publication 800-107, Revision 1, National Institute of Standards and Technology (NIST), Aug. 2012, retrieved on Nov. 24, 2015, from https://nvlpubs.nist.gov/nistpubs/Legacy/SP/nistspecialpublication800-107r1.pdf, 25 pages.
Dierks et al., "The TLS Protocol Version 1.0," Request for Comments 2246, Jan. 1999, 75 pages.
Dierks et al., "The Transport Layer Security (TLS) Protocol Version 1.2," Request for Comments 5246, Standards Track. Aug. 2008, 98 pages.
Eastlake, "Transport Layer Security (TLS) Extensions: Extension Definitions," Request for Comments: 6066, Standards Track, Jan. 2011, 25 pages.
Eronen et al., "Pre-Shared Key Ciphersuites for Transport Layer Security (TLS)," Request for Comments 4279, Dec. 2005, 16 pages.
Extended European Search Report daed Dec. 9, 2020, Application No. 18793825.3, 8 pages.
Ford-Hutchinson et al., "Securing FTP with TLS," The Internet Society, Network Working Group Request for Comments: 4217, Oct. 2005, 29 pages.
Friedl, M., et al., "Diffie-Hellman Group Exchange for the Secure Shell (SSH) Transport Layer Protocol," Request for Comments: 4419, Standards Track, Mar. 2006, 10 pages.
Friend et al., "Transport Layer Security (TLS) Protocol Compression Using Lempel-Ziv-Stac (LZS)," The Internet Society, Network Working Group Request for Comments: 3943, Nov. 2004, 13 pages.
Galbraith, J. and R. Thayer, "The Secure Shell (SSH) Public Key File Format," Request for Comments: 4716, Nov. 2006, 11 pages.
Galbraith, J., and P. Remaker, "The Secure Shell (SSH) Session Channel Break Extension," Request for Comments: 4335, Standards Track, Jan. 2006, 6 pages.
Galbraith, J., et al., "Secure Shell Public Key Subsystem," Request for Comments: 4819, Standards Track, Mar. 2007, 18 pages.
Gutmann et al., "Encrypt-then-MAC for Transport Layer Security (TLS) and Datagram Transport Layer Security (DTLS)," IETF Trust, Internet Engineering Taskforce (IETF) Request for Comments: 7366, Category: Standards Track, Sep. 2014, 7 pages.
Harris, B., "Improved Arcfour Modes for the Secure Shell (SSH) Transport Layer Protocol," Request for Comments 1345, Standards Track, Jan. 2006, 5 pages.
Harris, B., "RSA Key Exchange for the Secure Shell (SSH) Transport Layer Protocol," Request for Comments: 4432, Standards Track, Mar. 2006, 8 pages.
Hoffman et al., "SMTP Service Extension for Secure SMTP over Transport Layer Security," The Internet Society, Network Working Group Request for Comments: 3207, Category: Standards Track, Feb. 2002, 9 pages.
Hollenbeck, "Transport Layer Security Protocol Compression Methods," Request for Comments: 3749, Standards Track. May 2004, 8 pages.
Housley, R., "Using Advanced Encryption Standard (AES) CCN Mode With IPsec Encapsulating Security Payload (ESP)," Request for Comments: 4309, Standards Track, Dec. 2005, 14 pages.
Hutzelman, J., et al., "Generic Security Service Application Program Interface (GSS-API) Authentication and Key Exchange for the Secure Shell (SSH) Protocol," Request for Comments: 4462, Standards Track, May 2006, 28 pages.
Igoe, K., "Suite B Cryptographic Suites for Secure Shell (SSH)," Request for Comments: 6239, Informational, May 2011, 15 pages.
Igoe, K., and D. Stebila, "X.509v3 Certificates for Secure Shell Authentication," Request for Comments: 6187, Standards Track, Mar. 2011, 17 pages.
Igoe, K., and J. Solinas, "AES Galois Counter Mode for the Secure Shell Transport Layer Protocol," Request for Comments: 5647, Informational, Aug. 2009, 10 pages.
International Search Report and Written Opinion dated Jul. 20, 2018, International Patent Application No. PCT/US2018/031062, filed May 4, 2018, 16 pages.
Kanno et al., "Addition of the Camellia Cipher Suites to Transport Layer Security (TLS)," IETF Trust, Internet Engineering Task Force (IETF) Request for Comments: 6367, Category: Informational, Sep. 2011, 8 pages.
Karn et al., "The ESP DES-CBC Transform," Request for Comments: 1829, Standards Track, Aug. 1995, 11 pages.
Kato et al., "Camellia Cipher Suites for TLS," IETF Trust, Internet Engineering Task Force (IETF) Request for Comments: 5932, Category: 4132, Category: Standards Track, Jun. 2010, 6 pages.
Kent et al., "Security Architecture for the Internet Protocol," Request for Comments: 2401, Standards Track, Nov. 1998, 62 pages.
Kent, S., "IP Encapsulating Security Payload (ESP)," Request for Comments: 4303, Standards Track, Dec. 2005, 45 pages.
Kent, S., and K. Seo, "Security Architecture for the Internet Protocol," Request for Comments: 4301, Standards Track, Dec. 2005, 102 pages.
Khare et al., "Upgrading to TLS within HTTP/1.1," Request for Comments: 2817, Standards Track, May 2000, 13 pages.
Kim et al., "Addition of the ARIA Cipher Suites to Transport Layer Security (TLS)," IETF Trust, Internet Engineering fask Force (IETF) Request for Comments: 6209, Category: Informational, Apr. 2011, 9 pages.
Lee et al., "Addition of SEED Cipher Suites to Transport Layer Security (TLS)," Request for Comments: 4162, Standards Track, Aug. 2005, 6 pages.
Lehtinen, S., and C. Lonvick, "The Secure Shell (SSH) Protocol Assigned Numbers," Request for Comments: 4250, Standards Track, Jan. 2006, 19 pages.
Liu et al., "SLEP: Sparse learning with efficient projections—Version 4.1," Computer Science Center, Arizona State University, Dec. 28, 2011, 61 pages.
Mavrogiannopoulos et al., "Using OpenPGP Keys for Transport Layer Security (TLS) Authentication," Request tor Comments: 6091, Informational, Feb. 2011, 9 pages.
Mavrogiannopoulos, "Using OpenPGP Keys for Transport Layer Security (TLS) Authentication," Network Working Group Request for Comments: 5081, Category: Experimental, Nov. 2007, 8 pages.
McGrew et al., "AES-CCM Cipher Suites for Transport Layer Security (TLS)," Request for Comments: 6655, Standards Track, Jul. 2012, 8 pages.
Intellectual Property Office of Taiwan, "Office Action" in application No. 107115354 dated Oct. 31, 2022, 3 pages.
Australian Patent Office, "Examination Report" in Application No. 2018261181, dated Feb. 24, 2023, 3 pages.
Intellectual Property Office of Taiwan, "Decision Notice" in Application No. 107115354, dated Jun. 27, 2023, 3 pages.

* cited by examiner

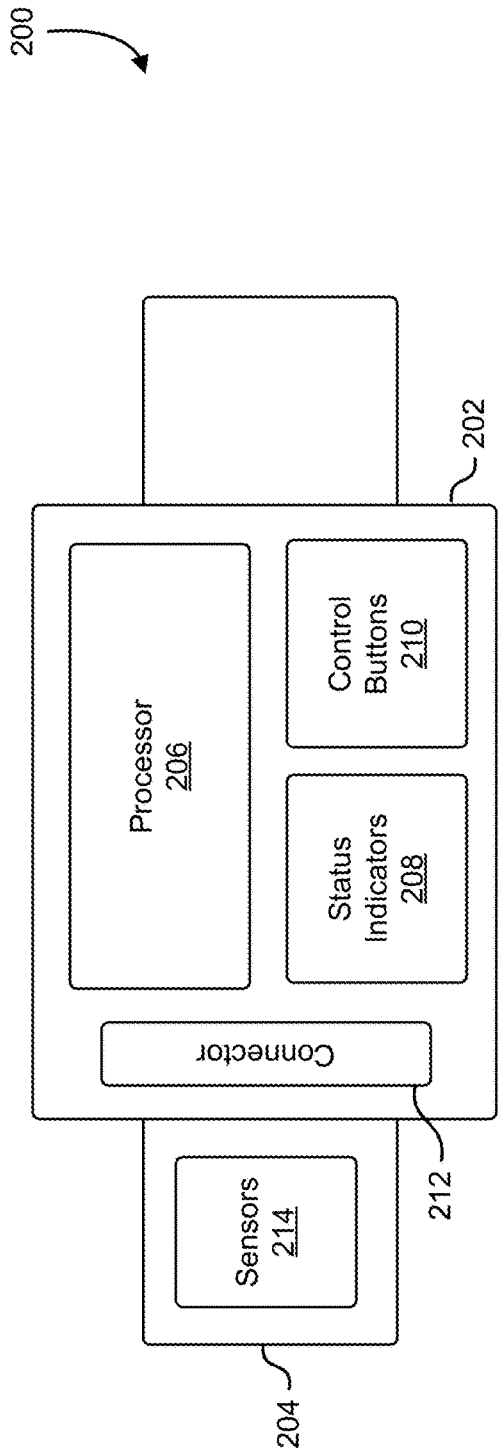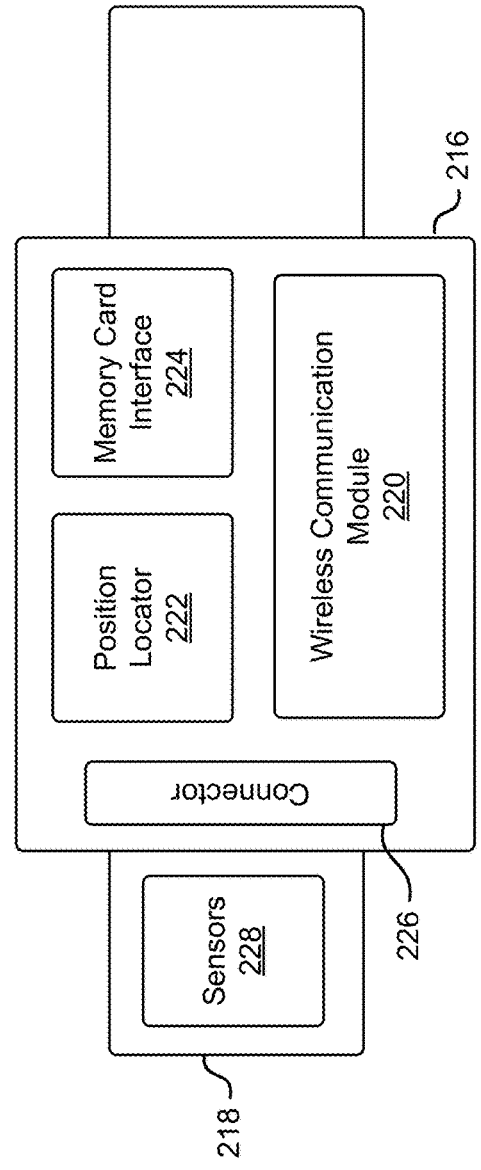

| Name | Designation | Role | Supervisor Name | Shift Start Time | Shift End Time | Update Shift Time |
|---|---|---|---|---|---|---|

No data available in table

Showing 0 of 0 entries                                              Previous   Next

Add New

Roger Moore
Warehouse Supervisor
Fedex

| Show 10 ▪ entries | | | | Search | |
|---|---|---|---|---|---|
| Location Code △ | Location Name | Address | Contact | Delete |
| Clemson Warehouse | | 105 Sloan Street, Clemson, South Carolina 20631 | 230-939-3864 | 🗑 |
| Clemson Warehouse | | 105 College Street, Washington D.C., Columbia 29631 | 630-999-3864 | 🗑 |

Showing 1 to 2 of 2 entries        Previous [1] Next

Thomas Anderson
CIO
Fedex

DEVICE STATS
Available Devices    2
Active Devices       2
Suspended Devices   24

Thomas Anderson
CIO
Fedex

| DEVICE STATS | |
|---|---|
| Available Devices | 2 |
| Active Devices | 2 |
| Suspended Devices | 24 |

Configure Organization Metrics

- ☑ Idle Time
- ☑ Sitting
- ☑ Standing
- ☑ Stuck in Traffic
- ☑ Lying
- ☑ Time to Exit Vehicle

- ☑ Drive Time
- ☑ Driving

- ☑ Aggressive Events
- ☑ Hard Acceleration
- ☑ Hard Corner
- ☑ Hard Brake
- ☑ Swerve
- ☑ Over Speed Limit

- ☑ Work Time
- ☑ Walking
- ☑ Running
- ☑ Walking up Stairs
- ☑ Walking Down Stairs

- ☑ Bend
- ☑ Bending

- ☑ Pulling
- ☑ Pushing
- ☑ Scrubbing

- ☑ Near Miss Events
- ☑ Falling
- ☑ Slipping
- ☑ Tripping

- ☑ Working From Heights
- ☑ Working From Heights

Update Configuration

WEARABLE ELECTRONIC BELT DEVICE

CROSS-REFERENCE TO RELATED APPLICATIONS

This application is a continuation of International Application No. PCT/US2018/031062, filed May 4, 2018, which claims priority from U.S. Provisional Patent Application No. 62/501,558, filed May 4, 2017, the disclosures of which are hereby incorporated herein in their entirety.

BACKGROUND

The management of employees in a business environment is an important problem. As employees perform their duties, employees may move about, operating machinery, driving, and performing various tasks at different locations. Monitoring the actions of employees is generally performed by supervisors who observe, track, and monitor the employees directly. This may require a significant number of supervisors, which can be expensive. In some cases, due to the physical distribution of the workforce, direct real-time supervision of individual employees may be impractical. Improved supervision can provide both improved worker safety and efficiency and, therefore, systems that provide improved monitoring of worker activities can benefit both the employer and the employee.

BRIEF DESCRIPTION OF THE DRAWINGS

Various embodiments in accordance with the present disclosure will be described with reference to the drawings, in which:

FIGS. 2*a* and 2*b* illustrate a belt that collects sensor data in accordance with various embodiments;

FIG. 34 illustrates an example of an administration tab on a supervisor dashboard in accordance with an embodiment;

FIG. 42 illustrates an example of an organization tab of a CIO dashboard in accordance with an embodiment;

FIG. 43 illustrates an example of a work location tab of a CIO dashboard in accordance with an embodiment;

FIG. 44 illustrates an example of a metrics configuration tab of a CIO dashboard in accordance with an embodiment;

FIG. 46 illustrates an example of a device management tab of a CIO dashboard in accordance with an embodiment;

DETAILED DESCRIPTION

Figure 1:
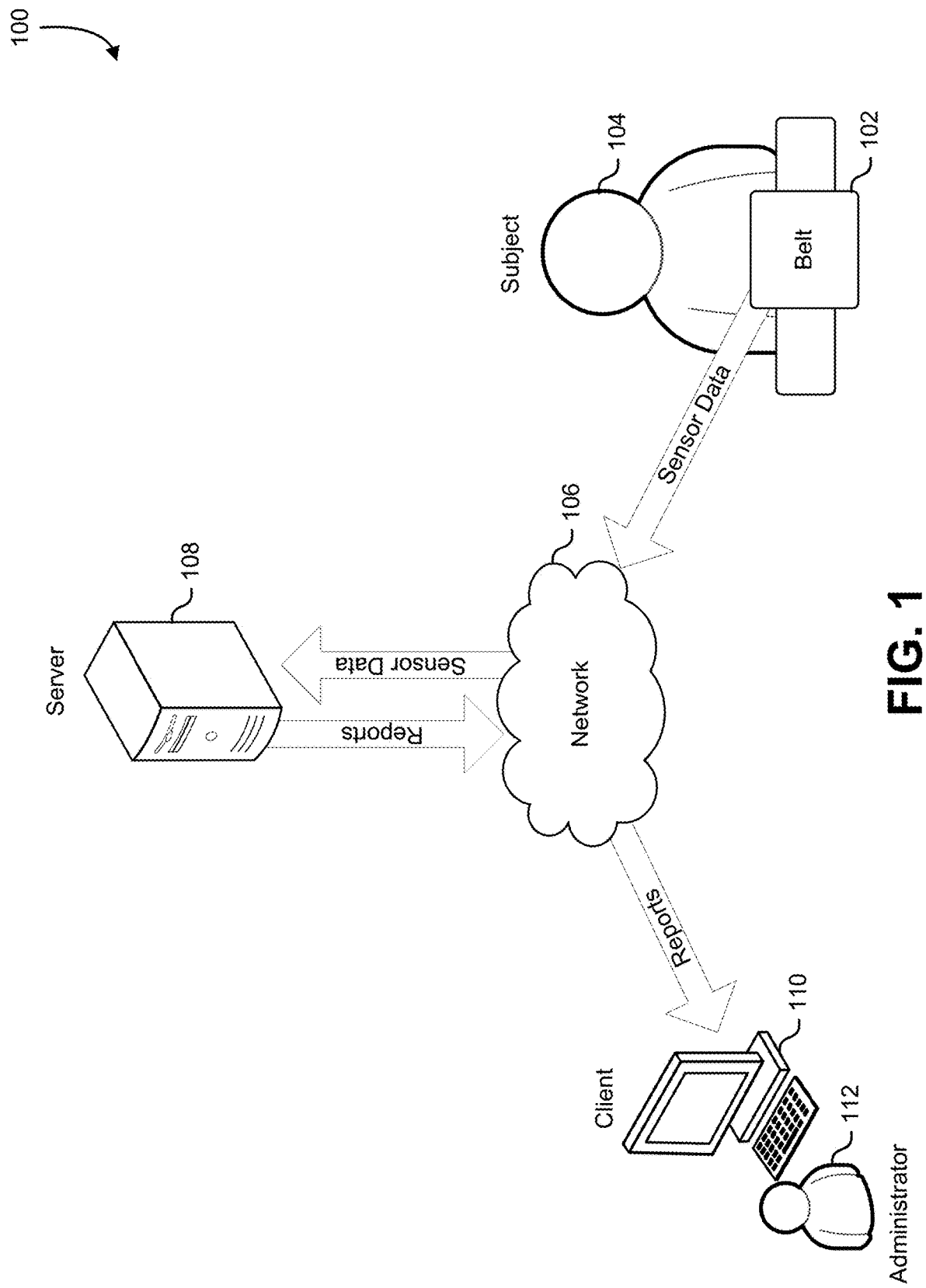
FIG. 1 illustrates an example environment in which the invention may be practiced in accordance with various embodiments.

The present document describes a system that includes a wearable belt that, when worn by a subject, collects data regarding a subject (such as a person) and the subject's environment. In various embodiments, the belt includes a processor and memory storing executable instructions that, as a result of being executed by the processor, cause the belt to collect data from a collection of sensors on the belt. In some examples, the sensors include sensors that monitor environmental conditions such as temperature, humidity, altitude, sound exposure, and geographic location. In another example, the system includes sensors that monitor the subject and record motion, acceleration, body temperature, heart rate, and steps taken. In an embodiment, the belt includes a wireless interface, such as a Wi-Fi or cellular interface, for transmitting the data to a remote server. In various embodiments, the remote server records the environmental conditions and other sensor data and determines a set of activities performed by the subject. Using an administrative console or other interface, an administrator is able to monitor the activity of a plurality of subjects. For example, in a business environment, a manager is able to use the system to acquire information regarding the productivity and safety of both individual workers and the workforce as a whole.

Various embodiments of the belt may include different configurations of sensors. In one embodiment, the belt includes a number of environmental sensors such as light sensors, temperature sensors (thermometers), atmospheric pressure sensors (absolute or relative air pressure sensors), humidity sensors, global-positioning sensors (such as Global Positioning System ("GPS") or Global Navigation Satellite System ("GLONASS") sensors), air quality sensors (particulate sensors or chemical sensors), moisture sensors, radiation sensors, acceleration sensors (accelerometers), shock and vibration sensors (Piezo electric sensors), orientation sensors (flux magnetometers or gravity sensors), and sound sensors (microphones). In another embodiment, the belt includes a number of sensors designed to measure characteristics of the subject such as body temperature sensors, strain gauges connected to various portions of the belt, clothing of the subject, or the subject itself, heart rate monitors, motion sensors, blood pressure sensors, or biometric sensors.

In some examples, sensors are positioned on the belt itself, including the inside and outside of the belt buckle, or waist strap of the belt. In other examples, sensors may be placed elsewhere on the subject and connected to the belt with wires, fiber-optic connections or wireless connections such as Bluetooth. In some embodiments, the belt may connect to remote environmental sensors in the vicinity of the subject via an infrared, radiofrequency, Bluetooth, or Wi-Fi connection. For example, the belt may connect to a wireless camera positioned in a room when the subject enters the room, and image data streamed from the camera to the belt where the data is stored in memory until it can be uploaded to a remote server. In another example, the belt may connect to an environmental sensor via Bluetooth at a remote outdoor location, retrieve temperature, humidity, and position information from the sensor, and relay the information to the remote server via a cellular connection on the belt. In yet another example, the belt may connect to a sensor via a near field radiofrequency connection, and data indicating the presence of the connection is sent to the remote server allowing the remote server to infer that the subject is near the sensor.

In an embodiment, the belt includes a number of strain sensors and orientation sensors that can be used to indicate a level of motion and exertion of the subject. In one implementation, a strain gauge is affixed to a section of the belt strap. As tension on the belt increases, the data collected by the strain gauge provides a measurement of the force exerted on the belt. Belt tension, in some examples, may be used as a proxy for estimating the lifting force exerted by a given subject. In some examples, a pair of strain gauges attached to calibrated material is inserted into the belt strap, and a differential signal from the two strain gauges provides an indication of force on the strap. In another implementation, a spring and displacement sensor are used to measure the tension on the belt strap. In another implementation, suspenders are added to the belt, and similar techniques are used to measure the strain on each suspender. In an embodiment, the belt includes one or more accelerometers that detect changes in the position of the subject. In one implementation, the belt includes X, Y, and Z-axis accelerometers that detect acceleration in three-dimensional space. In an embodiment, the belt includes positional indicators such as a flux magnetometer or solid-state compass to detect the direction the belt is facing and a gravity sensor to determine vertical orientation.

In an embodiment, the data collected with the sensors is stored in a memory on the belt, and a record of the data collection is maintained in a log file. The log file may include metadata regarding the data collection such as the time that the data was collected, the resolution and scaling of the collected data, and the authentication code or checksum for the data. In an embodiment, the belt uploads the data to a remote server using one or more communication interfaces. The communication interfaces may include a wireless interface such as a cellular interface, a Wi-Fi interface, an infrared interface, a Bluetooth interface, or a radiofrequency interface. The communication interfaces may include wired interfaces such as serial interfaces, Universal Serial Bus ("USB") interfaces, parallel interfaces, fiber optic interfaces, or Ethernet interfaces. In some examples, the belt may use a short-range wireless or wired connection to a long-range wireless device such as a cell phone in a hotspot configuration. In a hotspot configuration, data is transmitted from the belt to the long-range wireless device, and the long-range wireless device relays the data to a destination such as a remote server. In one embodiment, the belt includes an interface to removable memory such as an SD card interface. A removable memory is inserted into the interface, and sensor data is written to the removable memory. The memory may be removed periodically in order to transfer the data to the remote server, the memory is removed from the belt and connected to an interface that is in communication with the remote server (for example, via either a local connection or a network connection).

Data collected by the belt device may be processed in a variety of ways. In some embodiments, the belt device includes a processor and memory containing executable instructions that, as a result of being executed by the processor, transform the data or process the data into new data which is stored in a writable memory on the belt device. The new data or transform data may then be transmitted to a remote server for additional processing. In other examples, data is transferred to the remote server where it is then processed by the remote server. In some embodiments, as a result of processing the data, the remote server sends commands to the belt that cause the belt to modify future data collection. For example, the remote server may command that the belt sample particular data more frequently based on determinations made during the processing of the data.

In an embodiment, the system performs activity detection as part of processing the data collected by the belt device. Activities detected may include driving activities, working from height activities, lifting activities, walking jogging and running activities, traversing stairs, sleeping, tripping, falling, bending, twisting, pushing, and idle activities. Information about these activities may be used to improve the safety, productivity, and effectiveness of a work environment. Insights from this analysis may also be used to study activity patterns of an individual or a collection of individuals differentiated based on occupation, location, health condition, and other factors.

FIG. 1 illustrates an example environment 100 in which the invention may be practiced in accordance with various embodiments. In an embodiment, a belt 102 containing a variety of sensors and a communication interface is worn by a subject 104. The sensors may include strain sensors, temperature sensors, humidity sensors, moisture sensors, light sensors, shock and vibration sensors, altitude sensors, sound sensors, and other sensors. In some embodiments, the belt collects additional sensor data from sensors located in proximity to the belt via a short-range wireless communication link. For example, the belt may collect sensor data from a watch worn by the subject 104. In another example, the belt may collect environmental information from a sensor located in a room with the subject 104. The short-range wireless communication link may be a Bluetooth link, an infrared communication link, a radiofrequency communication link, or other short-range communication link.

The sensor data collected by the belt 102 is transmitted over a network 106 to a server 108 using a communication interface on the belt 102. In an embodiment, the communication interface is a cellular communication interface. The cellular communication interface may be based on GSM, Enhanced Data rates for GSM Evolution ("EDGE"), universal mobile telecommunications system ("UMTS") or long-term evolution ("LTE") standards. In another embodiment, the communication interface is a Wi-Fi interface, and the belt 102 connects to the network 106 via a Wi-Fi hotspot or router. In yet another embodiment, the communication interface enables connection to a cellular phone via either a wired or wireless connection, and the cellular phone relays information over the network 106 to the server 108. In yet another embodiment, the communication interface is a removable memory interface, and data is transmitted to the server 108 by writing the data on removable memory, removing the removable memory from the belt 102, and making the removable memory accessible to the server 108.

In an embodiment, the belt 102 includes strap portion and the buckle that fastens the ends of the strap together. The buckle incorporates a circuit board with a microcontroller, battery, I/O interface, and other circuitry. In some implementations, one or more sensors or other circuitry is positioned on the strap portion, and circuitry on the strap portion is connected to the circuitry on the buckle using flexible circuit board, ribbon cable, serial cable, or flex circuit.

The server 108 may be a computer server, server cluster, virtual computer system, container runtime, or serverless program execution environment. The server 108 includes an interface, such as an Ethernet interface, to the network 106. In an embodiment, the network 106 is the Internet. The server 108 receives information from the belt 102 and, in some examples, from one or more additional belts. In some examples, the server 108 validates the received sensor data by confirming a digital signature provided with the data by the belt 102. In some examples, after determining that the data is valid, the server 108 confirms receipt of the data, and the belt 102 deletes the data from memory on the belt 102.

The server 108 processes the sensor data to identify various conditions, activities, and events associated with the subject 104. In various examples, the server 108 uses the sensor data to identify activities such as driving, walking, working from heights, bending, lifting, and other activities. In some examples, the server 108 uses the sensor data to detect events such as unsafe driving events, slips and falls, injuries, or health emergencies.

In an embodiment, the server 108 produces reports which are transmitted to a client computer system 110 and viewed by an administrator 112. The reports allow the administrator 112 to obtain an overview of the workforce including safety statistics, injury statistics, worker productivity, and activity breakdowns (histograms). In one implementation, the client may be a personal computer system, laptop, tablet computer system, cell phone, or mobile device that hosts a web browser application. The server 108 provides the reports to the client computer system 110 by implementing a Web server. The reports are produced in hypertext markup language ("HTML") and are mapped to uniform resource locators ("URL"). The administrator 112 selects the URL in the browser application, and the browser application sends a hypertext transfer protocol ("HTTP") request to the server 108 specifying the URL. In response to the request, the server 108 retrieves the associated report in HTML format and returns the report to the web browser running on the client computer system 110. The web browser renders the report onto a display that is visible to the administrator 112. Reports may include links to other reports and active interface elements based on JavaScript or other script languages. For example, a report describing overall safety measures of the workforce may contain hyperlinks to individual safety incidents of individual workers. In another example, a report describing the activities of an individual worker may include hyperlinks to reports showing how the workforce as a whole performs the similar activity.

The server 108 may provide event notifications to the administrator 112. Notifications may be provided for events such as unsafe driving events, fall events, excessive idle time events, injury events, or medical emergency events. In one example, the administrator 112 is able to define a bounded geographical area, and events are provided when the subject 104 enters or exits the bounded geographical area. In another example, the bounded geographical area is a three-dimensional geographical area an entry or exit may occur vertically as well as horizontally. Event notifications may be provided as emails, text messages, pager messages, voicemails, automated phone calls. In some implementations, the server 108 generates and sends the notifications. In another implementation, the client computer system 110 receives information from the server 108, generates one or more notifications based at least in part on the information, and transmits the notifications to the administrator 112. In order to receive the notifications, the administrator 112 specifies a notification communication channel to the client computer system 110 or the server 108 by providing an email address, phone number, or pager ID.

FIGS. 2a and 2b illustrate a belt that collects sensor data in accordance with various embodiments. The belt includes a buckle portion with a variety of circuitry and a strap portion with a variety of sensors. FIG. 2a illustrates the back of the belt, and FIG. 2b illustrates the front of the belt.

FIG. 2a illustrates the back of the belt buckle 202 and strap 204. The belt buckle 202 includes a processor 206, a set of status indicators 208, and a set of control buttons 210. In some implementations, the processor 206 is a microcontroller that includes a processing unit, readable memory containing executable instructions, and read/write memory in an integrated unit. In another implementation, the processor 206 includes a microprocessor, computer-readable memory, and read/write memory which are interconnected on a circuit board. In one implementation, the belt has a flexible circuit board making up the belt body and buckle, and it has a connector that connects it to the other flexible circuit board which collects sensor information.

In an embodiment, the status indicators 208 include a number of lights such as light emitting diodes ("LEDs"), incandescent lights, plasma emitters, liquid crystal displays ("LCD's"), or organic light emitting devices ("OLED"). In one embodiment, a multicolor LED having three states (red, green, and blue) is used. Red signals a belt malfunction, green signals that the belt is powered on, and blue signals that location tracking for the belt is functioning (for example, the GPS receiver on the belt is locked to one or more GPS satellites or other signal emitters).

In an embodiment, the control buttons 210 include an on/off toggle switch. In one example, the control buttons 210 include a multifunctional button that may be used to place the belt in a hotspot mode and allows the user to reset the circuitry on the belt. In some embodiments, the belt includes two or more control buttons, including a power button to turn the belt ON and OFF and a multifunctional button, such as above. Different numbers of buttons and distributions of functions among buttons are also considered as being within the scope of the present disclosure.

In an embodiment, power is optimized in order to save battery life. The system, in an embodiment, includes multiple distributed sensors 214 along the belt, as well as a microprocessor that draws electrical current when the belt is turned on. In some examples, a real time feedback system monitors the effective usage of the individual sensors in order to reduce the overall power consumption. Based at least in part on one or more of the activities identified, location, time, and other factors, individual sensors are put into a sleep state that reduces power consumption. For example, if an employee works standing in a specific place regularly, location sensing will be put into a low-power sleep state. Movement of the employee, which is sensed by motion sensors, triggers the location tracking to be re-enabled and placed in a higher power consuming state. Based at least in part on activity patterns of a worker in a particular job and the activity pattern of that person, in an embodiment, sensor usage is adjusted over time using machine-learning algorithms.

In an embodiment, power consumption may be minimized by using a WiFi network for data transmission when its Wi-Fi access point is accessible and available. If Wi-Fi is not available, a cellular interface may be used on an intermittent basis to reduce power consumption. When a Wi-Fi connection is available, cellular interface components may be turned off or maintained in a low-power state. In general, usage of WiFi connectivity results in consumption of lower power compared to using a 3G/4G/LTE network. In various implementations, the sensor Belt is provided with the ability to connect to WiFi networks by entering credentials into a Mobile app connected to the belt. In some examples, since power consumed for data transmission is approximately proportional to the amount of data generated, data collected is reduced by using methods similar to methods used to save power drawn by sensors as mentioned above. Data compression methods may also be used to reduce the volume of data ultimately uploaded to a cloud-based data storage service.

Another major source of power consumption is in the components responsible for data transmission to cloud using WiFi or 3G network. In an embodiment, certain measures are taken to reduce the power consumption of the Wi-Fi module. In some examples, the Wi-Fi module is operated at low transmission speeds to consume less power. Out of six channels at which the Wi-Fi module can operate, the one with the lowest power consumption is used. Usage of Wi-Fi in the low transmission speeds results in lower consumption of power. The sensor Belt is configured so that it gains access to any Wi-Fi network by entering credentials into a Mobile app. If the available Wi-Fi strength is below a specified threshold, the Wi-Fi module is put to sleep to prevent the Wi-Fi module from using power while the Wi-Fi module keeps looking for Wi-Fi networks.

Based at least in part on the work pattern of an individual belt, the belt may be trained to record data from a subset of the available sensors. Sensors outside the subset will be left off or in a low-power state and turned on only as necessary. The sensor usage may, in various embodiments, be determined using an unsupervised machine learning process in advanced stages of the belt development. This is an ongoing process that takes into account the work schedule of the person (i.e., a person who mostly walks around on flat ground doesn't need to have all the accelerometers or gyroscopes working at the same time). In another example, a person who mostly works on flat ground does not need to have the altimeter measurement done frequently. In some examples, the belt is remotely advised on the sensor data to be collected and the frequency of data collection based on the automated learning process.

In an embodiment, a connector 212 provides an electrical connection between the front of the belt and the back of the belt, and/or between electrical components on the belt buckle 202 and electrical components on the strap 204. In one implementation, the connector includes through-hole connectors that allow electrical connections to be established between the front side and back side of the belt buckle 202. In another implementation, the connector includes a ribbon cable, serial cable, wire, or flex circuit that enables a flexible coupling between the components on the belt buckle 202 and the components on the strap 204.

FIG. 2b illustrates an example of electrical components on the front of the buckle 216 and strap 218. In an embodiment, a cellular communication module 220, a position locator 222, and a memory card interface 224 are located on the front of the buckle 216. The wireless communication module 220 can be a cellular communication interface, a Wi-Fi interface, a blue tooth interface, an infrared interface, a radiofrequency interface, or other communication interface. In one implementation, the wireless communication module 220 is a cellular interface that implements a data protocol such as EDGE, 2G, 3G, or LTE. In another implementation, the wireless communication module 220 is a Wi-Fi interface that connects to an Internet router or Internet hotspot. In yet another implementation, the wireless communication module 220 is a Bluetooth interface that connects to an Internet router, hotspot, or cell phone configured to act as a wireless hotspot.

The position locator 222 collects electrical signals that allow the belt to determine its geographical location. In an embodiment, the position locator 222 is a Global Positioning System receiver or a GLONASS receiver. In an embodiment, the position locator 222 is a near field radiofrequency receiver that receives position information from location beacons. In an embodiment, the position locator 222 is a Wi-Fi interface that implements the Wi-Fi positioning system.

In some embodiments, indoor positioning is provided on the belt device. Indoor positioning is a challenge due to limited and often unreliable GPS signals indoors. To address this, in an embodiment, an indoor map is generated using accelerometer/gyroscope to count steps and a magnetometer to determine the direction of movement to generate a breadcrumb report indoors. In some implementations, the GPS may be utilized to correct the breadcrumb report. Thus the combination of accelerometer/gyroscope, magnetometer, and GPS will be used to generate a more accurate map of the movements indoors than if the map was generated using techniques individually.

The memory card interface 224 provides an interface to removable computer-readable memory. In one embodiment, the memory card interface 224 is an SD card interface for removable SD card memory. In another embodiment, the memory card interface 224 is a USB interface. In yet another embodiment, the memory card interface 224 is a Sim card interface. As described above, the belt buckle includes a connector 226 that allows electrical components on the front of the buckle to be connected to optical components on the back of the buckle. The connector 226 may, in various embodiments, allow components on the buckle to be connected to electrical components on the strap 218. In various embodiments, the front of the strap 218 may include one or more sensors 228 which provide sensor data to the electronic components on the buckle 216.

In various embodiments, a variety of sensors may be positioned on the strap of the belt. In one implementation, the sensors include one or more strain sensors that detect tension on the strap material. The sensors may be positioned on the inside or outside of the belt. In some examples, curvature of the belt may be detected by placing a strain sensor on opposing sides of the belt strap. As the belt is curved around the body of the subject, the outside strain sensor is stretched more than the inside strain sensor, providing an indication of curvature. In some implementations, a plurality of pairs of strain sensors is positioned around the strap, and the differential signals between opposing pairs of strain sensors provide a measure of curvature around the waist of the subject. In another example, a pair of strain sensors on the top edge of the belt and the bottom edge near the center of the back of the belt provide an indication of bowing of the belt when the subject bends at the waist. When the subject bends over, a belt loop on the center of subject's trousers pulls down on the belt and the belt bows into a slight V-shape. A resulting differential signal between the pair of strain sensors provides a signal that is roughly proportional to the amount the subject bends.

In additional examples, the sensors on the belt strap may include temperature sensors, humidity sensors, moisture sensors, microphones, audible speakers, accelerometers, altimeters, atmospheric sensors, chemical contamination sensors, radiation sensors, and environmental sensors. In some examples, the sensors include orientation sensors such as solid-state flux magnetometers, Hall effect sensors, directional light sensors, and gravity sensors.

Figure 3:
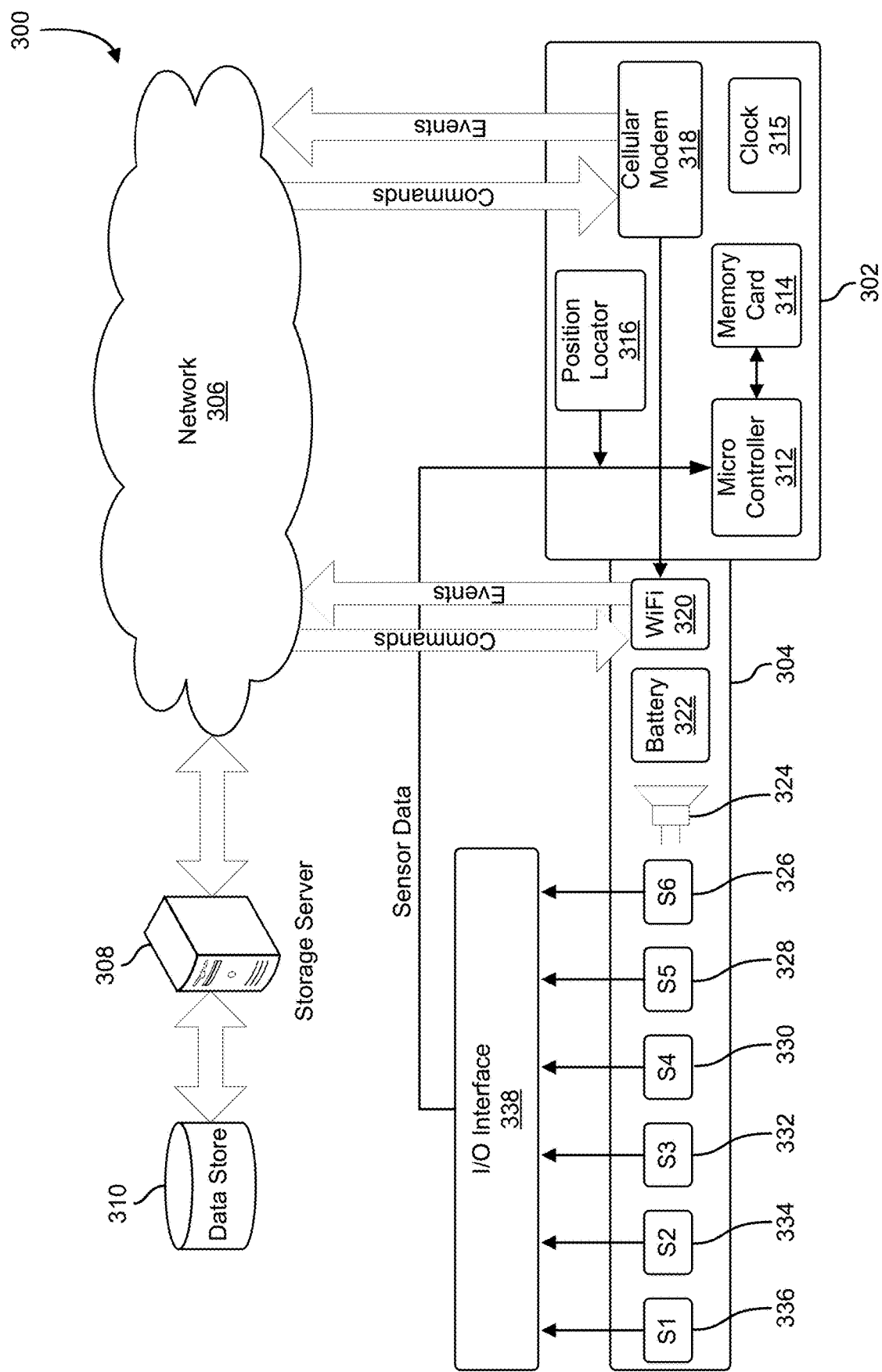
FIG. 3 illustrates an example of a belt that collects and uploads a variety of sensor data to a server in accordance with various embodiments.

FIG. 3 illustrates an example of a system 300 that includes a belt that collects and uploads a variety of sensor data to a server in accordance with various embodiments. In an embodiment, the system 300 includes a belt that has a buckle portion 302 connected to a strap portion 304. The belt includes various electronic components and a wireless interface that exchanges data over a network 306 with the storage server 308. The storage server 308 maintains a data store 310 on a disk drive, external storage device, optical storage device, or solid-state memory connected to the storage server 308.

In an embodiment, the buckle portion 302 includes a microcontroller 312, a memory card interface and memory card 314, a clock 315, a position locator 316, and a cellular modem 318. The strap portion 304 includes, in an embodiment, a Wi-Fi interface 320, a battery 322, and a speaker 324 such as a buzzer or Piezo electric speaker. The speaker 324 may be used to notify the wearer of various events that would require his or her attention. In various implementations, the battery 322 may be a replaceable single-use battery such as a lithium or alkaline cell, or a rechargeable lithium-ion, nickel cadmium, or nickel metal hydride cell. In an embodiment, the belt includes charging circuitry to recharge the battery. In an embodiment, the strap portion 304 includes a first strain sensor 336, a second strain sensor 334, a third strain sensor 332, a fourth strain sensor 330, the fifth strain sensor 328, and a sixth strain sensor 326. In an embodiment, the belt omits the cellular modem 318.

A set of sensor data is collected by the strain sensors and sent to the microcontroller on the buckle portion 302 using an I/O interface 338. In an embodiment, the I/O interface 338 includes a set of multiplexed analog-to-digital converters that convert analog signals produced by the strain sensors into digital data which may be read by the microcontroller 312. In various examples, additional sensor data may be provided from other environmental sensors on the belt. The microcontroller 312 sends the collected data to the storage server 308 via the Wi-Fi interface 320 or cellular modem 318 based at least in part on the availability of Wi-Fi and cellular signals. The storage server 308 stores the sensor data on the data store 310. In various embodiments, the storage server 308 may process the sensor data to identify various activities performed by the wearer of the belt. In additional embodiments, various reports and analyses may be made by the storage server 308 and provided to an administrator.

In an embodiment, two pressure sensors and combination of the altimeter/temperature sensor/humidity sensor are present along the length of the belt. In one example, the Wi-Fi on the buckle refers to the Wi-Fi chip that sends the sensor data to a database service (or other data storage service). In some embodiments, a buzzer is included to notify the user about events that would require the attention of the wearer. In an embodiment, the combination of the altimeter/temperature sensor/humidity sensor is on a first rigid board along the length of the belt. There are four interconnected batteries that power the rigid/flex circuit board. The batteries are small and spread across to allow for the flexion of the belt body.

Figure 4:
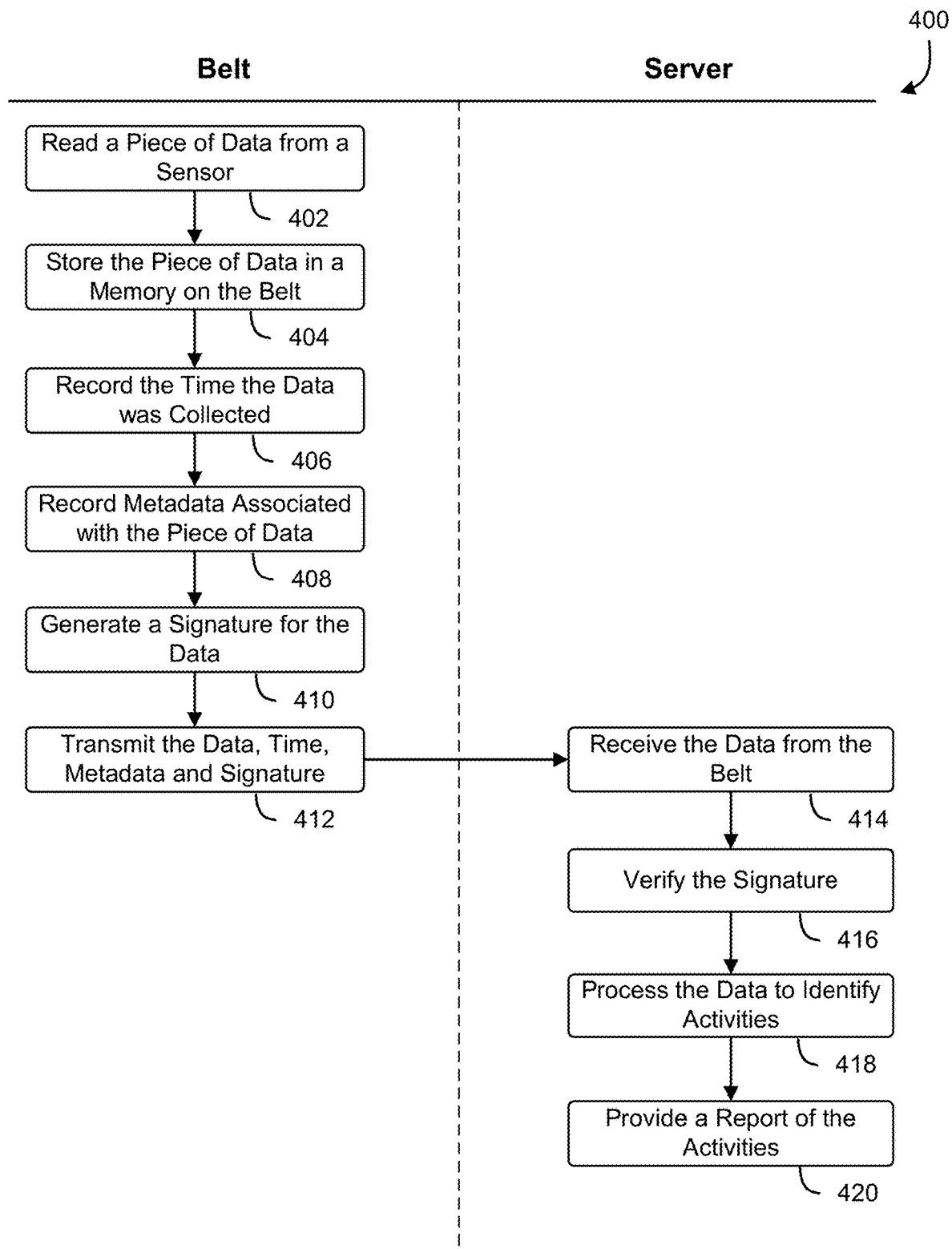
FIG. 4 illustrates an example of a process that, as a result of being performed by a belt and a server, generates and transfers a sensor-data record, in accordance with various embodiments.

FIG. 4 illustrates an example of a process 400 that, as a result of being performed by a belt and a server, generates and transfers a sensor-data record, in accordance with various embodiments. The process begins at block 402 with the belt reading a piece of data from a sensor, such as a strain sensor, a temperature sensor, or other sensor. In an embodiment, a processor on the belt acquires the data by selecting an analog-to-digital conversion channel corresponding to a particular strain sensor and reads a digital representation of an analog voltage produced by the strain sensor. At block 404, the belt stores the piece of data in a memory on the belt. In some implementations, at block 406, the belt records a time at which the sensor data was collected. In some implementations, at block 408, the belt records metadata associated with the piece of data such as environmental conditions at the time the data was read, a resolution and scale for the data, a name or an identifier associated with the sensor, or other metadata. In an embodiment, at block 410, the belt generates a digital signature for the sensor data. In some implementations, the digital signature is generated for the combination of the sensor data, the timestamp and the metadata. The digital signature may be generated with a cryptographic key stored on the belt. In some examples the cryptographic key is in a symmetric cryptographic key pair where the private key is used to generate the signature, and the public key is provided to a data storage server or other data consumer. In an embodiment, the digital signature is generated by a crypto processor containing a temper-resistant memory, and the cryptographic key is maintained as a non-exportable value in the tamper-resistant memory.

In an embodiment, at block 412, the belt transmits the data, time, metadata and digital signature to the server computer system. In some implementations, if a Wi-Fi signal is available, the data is transmitted over a Wi-Fi signal to the server. If a Wi-Fi signal is not available, or if the network to which the server is connected is not accessible via any available Wi-Fi network, a cellular interface may be used to transmit the data to the server.

In an embodiment, at block 414, the server receives the data, and optional time, metadata and signature from the belt. In some examples, if a digital signature is received, the server verifies the integrity of the data, at block 416, by verifying the signature using the cryptographic key or a public key corresponding to the cryptographic key used above. If the server determines that the signature is valid, the data is determined to be authentic, and the server processes 418 the data to identify various activities performed by the wearer of the belt. In some examples, activity classification is performed. At block 420, in various embodiments, the server calculates metrics from the classified data which may be presented in various dashboards for use by managers, administrators, or other persons. In some implementations, reports and/or metrics are created from the analyzed data in the form of webpages which are served over a computer network to a browser running on a remote computer system, and the remote computer system presents the reports and/or metrics on a display.

Figure 5:
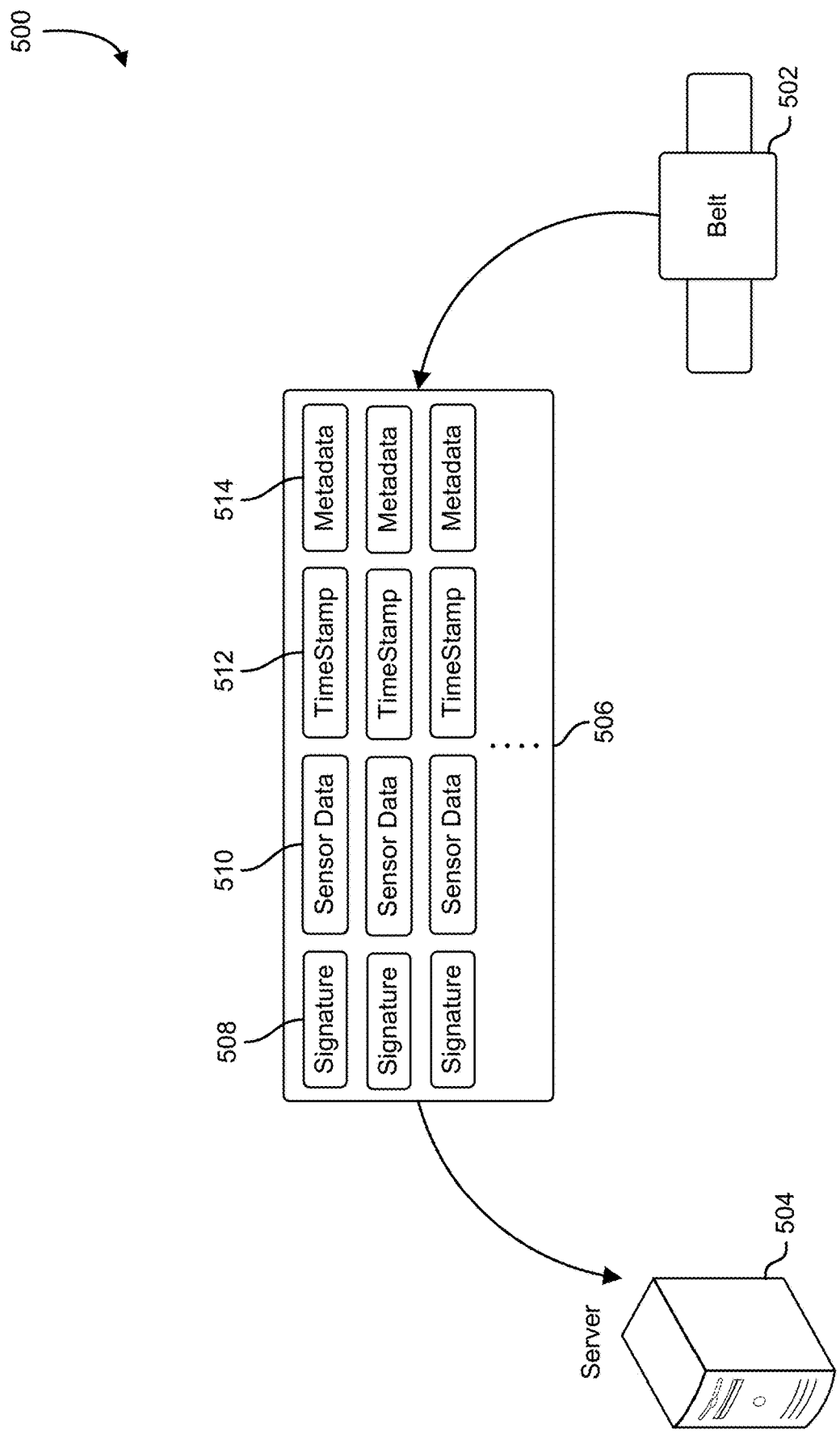
FIG. 5 illustrates an example of data exchanged between a belt and a server in accordance with various embodiments.

FIG. 5 illustrates an example of a system 500 that exchanges data between a belt and a server in accordance with various embodiments. In an embodiment, a belt 502 collects sensor data, timestamps, and other metadata which is then signed and sent to a server computer system 504. In various embodiments, the server computer system receives, validates, and stores the sensor data for use in identifying activities performed by the wearer of the belt.

In some implementations, the data is sent from the belt to the server as it is collected, with a single data entry and associated metadata sent to the server computer system 504 in real time. In another implementation, sensor data is collected in a memory on the belt 502 until a threshold amount of data is collected. The threshold may be determined based on the size of available buffer memory, a maximum allowable latency, or combination of the two. When the threshold amount of data is collected, the belt 502 assembles a data packet 506 in which the data and its associated metadata is transmitted to the server computer system 504.

In an embodiment, the data packet 506 includes one or more sensor data records, and each sensor data record includes a signature field 508, a sensor data field 510, a timestamp 512, and the metadata field 514. The signature field 508 contains a digital signature of the sensor data, timestamp, and metadata is generated with a cryptographic key by the belt 502. Upon receipt of the data, the server computer system 504 is able to determine the authenticity of the data by validating the signature 508 against the received sensor data, timestamp, and metadata. The sensor data 510 is the data collected by the belt 502. The timestamp 512 is a representation of the time at which the sensor data 510 was collected by the belt 502. The metadata 514 contains, in various embodiments, environmental data, or other characteristics of the sensor data 510 as described above.

Figure 6:
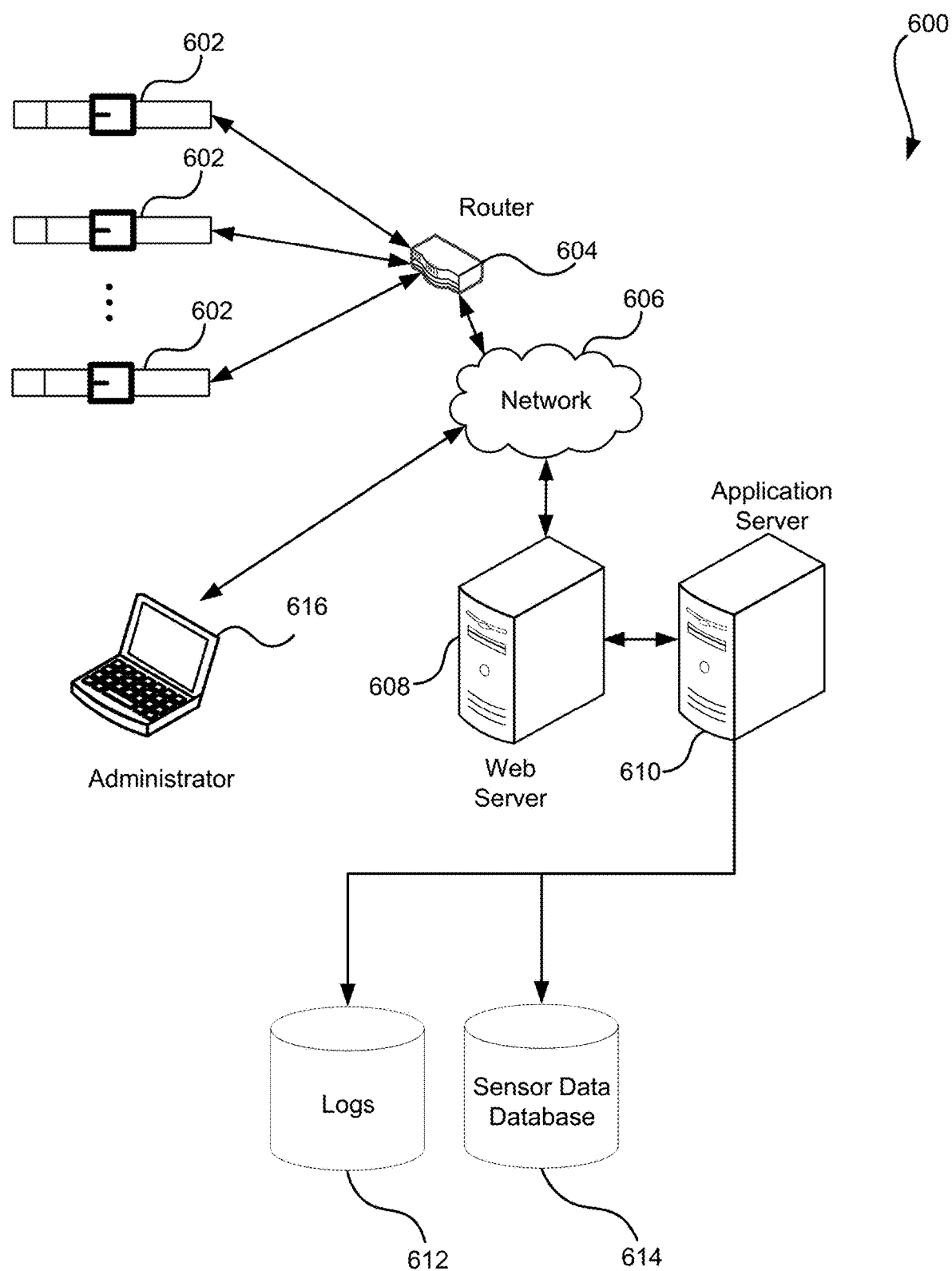
FIG. 6 illustrates an example of a system that generates and presents an activity report to an administrator, in accordance with various embodiments.

FIG. 6 illustrates an example of a system 600 that generates and presents an activity report to an administrator 616, in accordance with various embodiments. In an embodiment, a set of belts 602 as described elsewhere in the present document connect via a router 604 to a computer network 606. In some examples, the router 604 is a hub or switch and the network 606 is a local network. In another example, the router 604 is a network router and the network 606 is the Internet. In an embodiment, each belt in the set of belts 602 connects to a Web server 608. The Web server 608 is connected to an application server 610 which maintains a log database 612 and a database of sensor data 614. In some implementations, the database of sensor data 614 is a Cloudant NoSQL Database.

In one example, a belt in the set of belts 602 collects a set of sensor data. The sensor data is uploaded through the router 604 over the computer network 606 to the Web server 608. In some implementations, the sensor data is uploaded via an FTP connection. In other implementations, the sensor data is uploaded as a parameter of a web request. The Web server 608 sends the data to the application server 610, and the application server stores the sensor data in the database of sensor data 614. A log entry is created on the log database 612 recording that the data was received from the belt.

In some examples, MQ telemetry transport ("MQTT") 8883 port is used by each belt to connect to an organization's Internet of things foundation ("IOTF"). In FIG. 6, MQTT (MQ Telemetry Transport) is an ISO standard (ISO/IEC PRF 20922) publish-subscribe-based "lightweight" messaging protocol for use on top of the TCP/IP protocol. It is designed for connections with remote locations where a "small code footprint" is required or the network bandwidth is limited. MQTT TLS/SSH port 8883 is used by belts to send data to a database service used to implement the database of sensor data 614.

In an example, the belt comes online once every five minutes for few seconds and sends the data acquired over the interval to the database service and resumes the data collection process. Note that other frequencies, which may or may not be periodic, may be used. In an embodiment, if the WiFi network is not available, the data is accumulated in the SD storage and then is later sent when the network is available.

Figure 7:
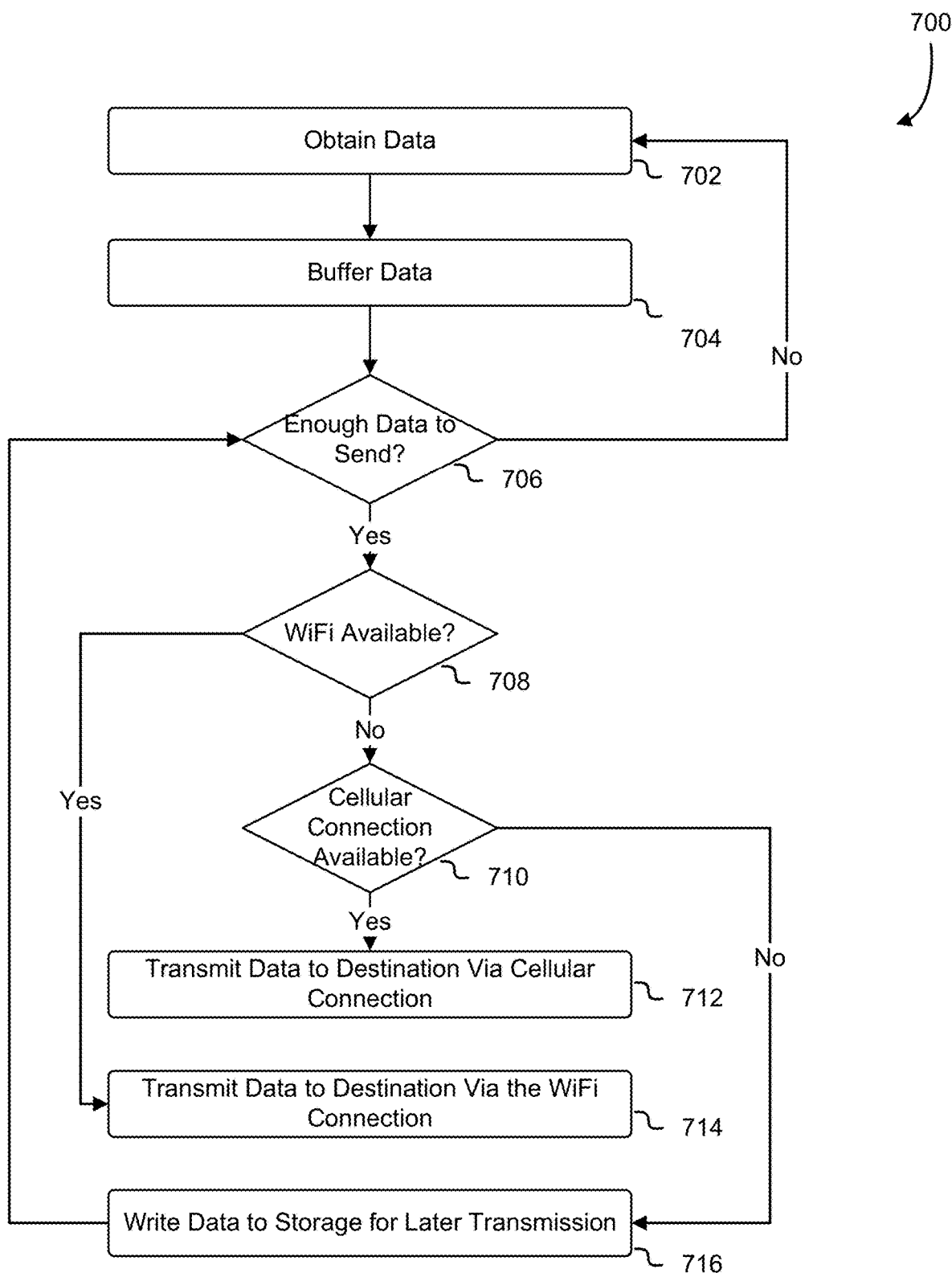
FIG. 7 illustrates an example of a process that, as a result of being performed by a belt, transmits data to a storage server, in accordance with various embodiments.

FIG. 7 illustrates an example of a process 700 that, as a result of being performed by a belt, transmits data to a storage server, in accordance with various embodiments. In an embodiment, the process begins at block 702 with a belt obtaining sensor data from one or more sensors. In some examples, the sensor data may include a timestamp, metadata, and a digital signature to authenticate the data. At block 704, the belt stores the obtained sensor data in a buffer on the belt. At decision block 706, the belt determines whether there is enough data in the buffer to send to a data storage server. If there is not enough data in the buffer to send to a data storage server, execution returns to block 702 and additional data is obtained. If there is enough data in the buffer to send to a data storage server, execution advances to decision block 708. In some implementations, determining if there is enough data in the buffer is accomplished by comparing the amount of data in the buffer to a threshold amount of data. In other implementations, determining if there is enough data in the buffer is accomplished based at least in part on the age of the data in the buffer. For example, if the oldest data in the buffer exceeds a threshold age, the data in the buffer is sent to the data storage server. In some implementations, a combination of these techniques may be used.

At decision block 708, the belt determines if the data storage service is accessible via a Wi-Fi connection. If the data storage server is accessible via a Wi-Fi connection, execution advances to block 714 and the data is transmitted to the data storage service via the Wi-Fi connection. If the data storage server is not accessible via a Wi-Fi connection, execution advances to decision block 710. In some embodiments, if the belt does not contain a cellular interface, execution proceeds to block 716. At decision block 710, the belt determines whether the data storage server is accessible via a cellular connection. If the data storage server is accessible via a cellular connection, execution advances to block 712 and the belt transmits the data to the data storage server using the cellular connection. If the data storage server is not accessible via a cellular connection, execution advances to block 716 and the data is written to memory on the belt device for later transmission. In some examples, the data is retained in the buffer on the belt for later transmission.

In an embodiment, at block 716, if data is retained for later transmission, execution returns to block 702 and additional data is obtained. If the data is successfully transmitted at either blocks 712 or 714, in various embodiments, execution returns to block 702 where the belt obtains new data.

Figure 8:
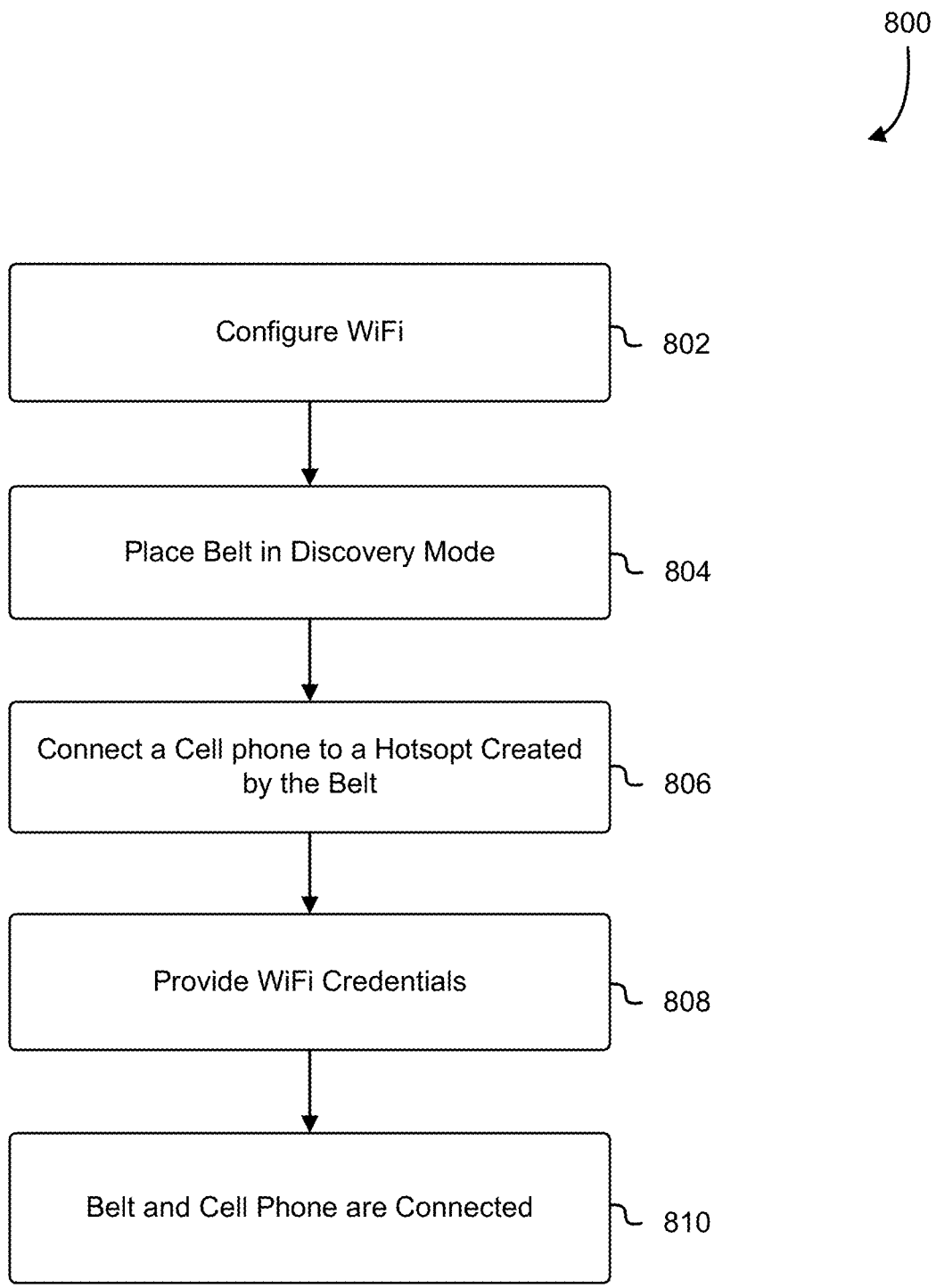
FIG. 8 illustrates an example of a process that, as a result of being performed by a belt and a cell phone, establishes a hotspot network, in accordance with various embodiments.

FIG. 8 illustrates an example of a process that, as a result of being performed by a belt and a cell phone, establishes a hotspot network, in accordance with various embodiments. The process of configuring a Wi-Fi hotspot begins at block 802. At block 804, the belt is placed in discovery mode. In some examples, the belt is placed in discovery mode by pressing a start button on the belt with a long button press that exceeds a threshold amount of time. In discovery mode, the belt generates a hotspot ID and broadcasts the hotspot ID via the Wi-Fi interface on the belt. In an embodiment, the hotspot ID is unique for each belt. At block 806, the user connects a cell phone to the Wi-Fi hotspot broadcast by the belt using the Wi-Fi interface on the cell phone. At block 808, the belt requests credentials to authorize connection to the Wi-Fi hotspot. In an example, the user enters the SSID and password of the belt into a dialogue displayed by the cell phone to authorize connection to the Wi-Fi hotspot.

At block 810, the belt and the cell phone are connected via a Wi-Fi interface. In some examples, the cell phone uses a cellular connection of the belt to transmit data through the belt to a network. In other examples, the belt uses a cellular connection on the cell phone to transmit data through the cell phone to a network.

Figure 9:
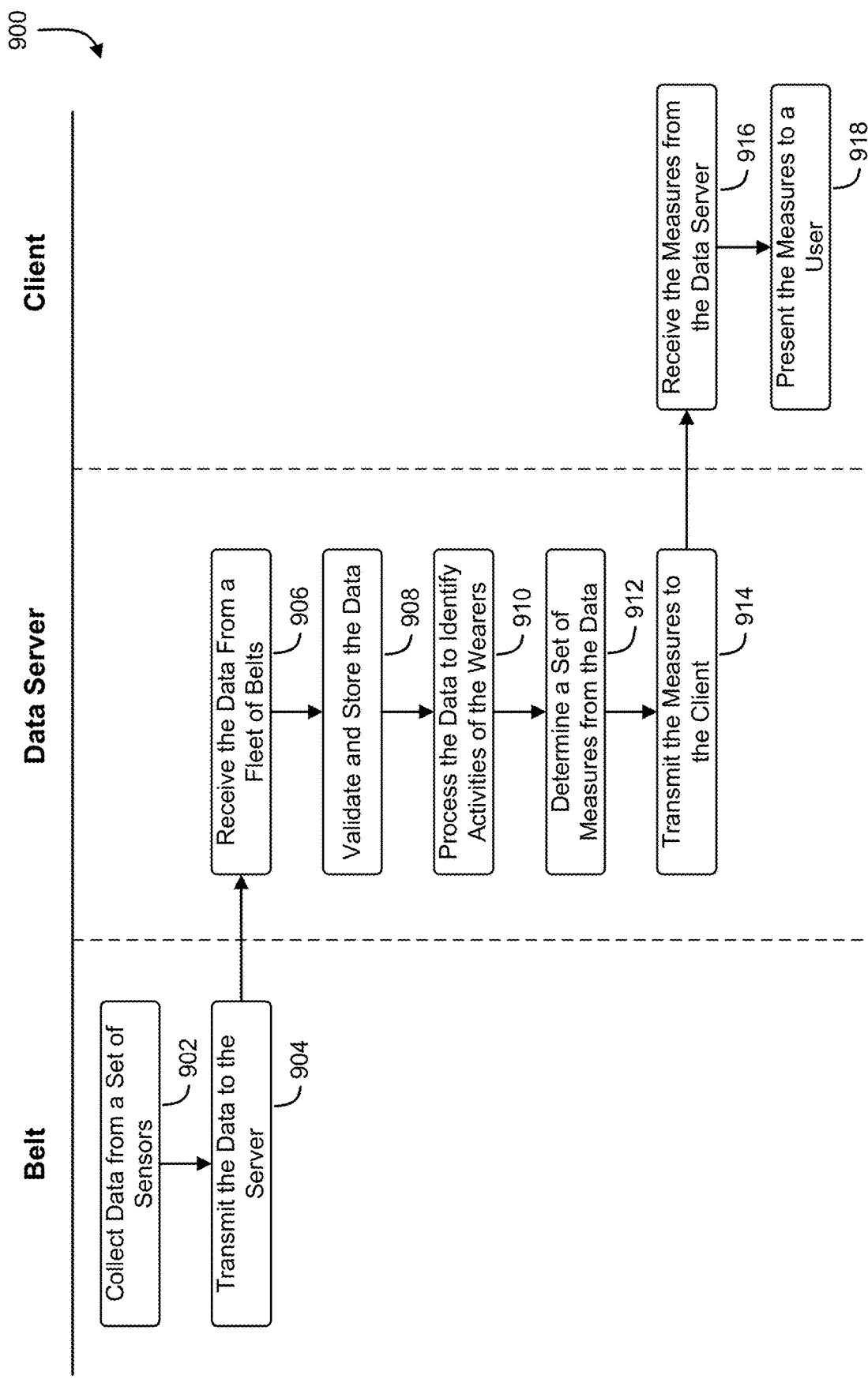
FIG. 9 illustrates an example of a process that, as a result of being performed by a belt, a server, and a client computer system, produces a report and presents the report to an administrator, in accordance with various embodiments.

FIG. 9 illustrates an example of a process 900 that, as a result of being performed by a belt, a server, and a client computer system, produces a report and presents the report to an administrator, in accordance with various embodiments. The process begins at block 902 with a belt collecting a set of data from a set of sensors on the belt. In some implementations, the set of data may include metadata associated with the data and validation signatures that assure the authenticity of the data. At block 904, the belt transmits the data and, optionally, the metadata and validation signatures to a data server. In some examples, the data is transmitted over a Wi-Fi or cellular connection.

In an embodiment, at block 906, the data server receives the data from the belt. In some examples, the data includes an identifier that identifies the belt within a fleet of belts, each of which sends data to a data server. At block 908, the data server validates the data received by confirming that the belt is within the fleet of managed belts and, if available, by validating a signature of the data. The data server stores the data in a memory or other storage device accessible to the data server. At block 910, the data server processes the sensor data from each belt to identify activities performed by the wearer of each belt. The activities may include activities such as driving, working from heights, and other activities described elsewhere in the present document. In some examples, the activity information associated with each belt is used to synthesize 912 a set of measures that are attributable to the wearer. The measures may include things such as amount of time spent idle, amount of time spent driving, and amount of time spent working from heights. At block 914, the data server transmits the measures to a client computer system. In some implementations, the data server generates reports based on the sensor data and/or the measures and transmits the reports to the client computer system.

In an embodiment, at block 916, the client computer system receives the measures and/or reports from the data server. In some implementations, the reports are received in the form of a webpage. At block 918, an application running on the client computer system displays the measures and reports to a user, administrator, or manager. In some implementations, the application is a web browser, and the web browser renders the webpage on a display on the client device.

Figure 10:
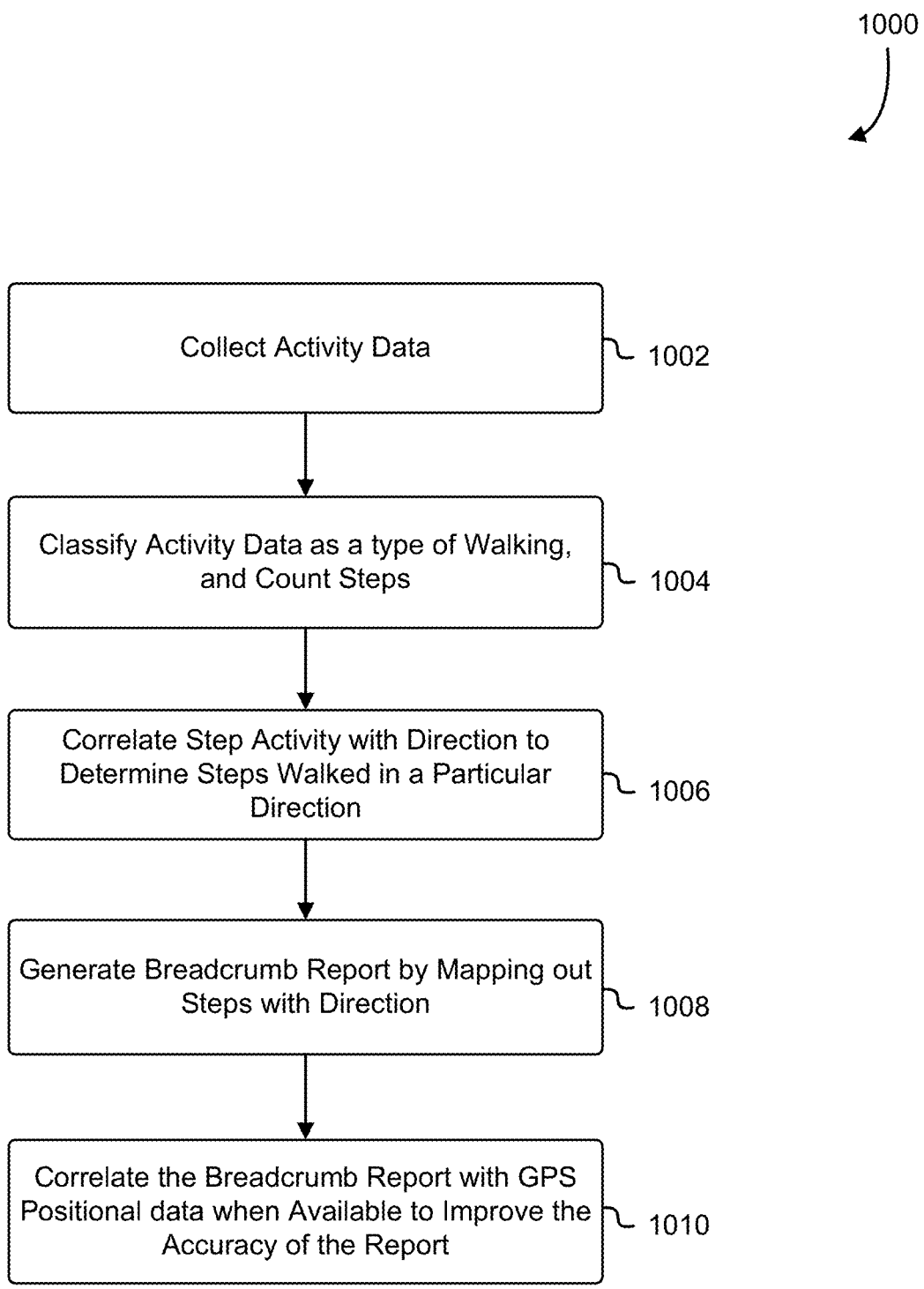
FIG. 10 illustrates an example of a process that, as a result of being performed by a computer system, produces a report showing the movements of a subject, in accordance with various embodiments.

FIG. 10 illustrates an example of a process 1000 that, as a result of being performed by a computer system, produces a report showing the movements of a subject, in accordance with various embodiments. In an embodiment, the movements of the subject are collected using a belt that has a GPS receiver, as well as indoor navigation sensors such as accelerometers, magnetometers, and gyroscopes. Indoor positioning is a challenge due to limited and often unreliable GPS signals indoors. To address this, in an embodiment, an indoor map is generated using an accelerometer/gyroscope to count steps and a magnetometer to determine the direction of movement to generate a breadcrumb report indoors. Wherever possible, the GPS will then be utilized to correct the breadcrumb report as much as possible. Thus the combination of accelerometer/gyroscope, magnetometer, and GPS is used to generate a more accurate map of the movements indoors than if the map was generated using individual techniques by themselves.

The process begins at block 1002 where, in an embodiment, the computer system collects activity data from a belt worn by a subject. The activity data includes activities such as walking, jogging, running, riding, driving, or crawling. At block 1004, the computer system analyzes the activities and identifies those activities that can be classified as a walking-type activity. A walking-type activity includes activities such as walking, jogging, running, or crawling where motion can be discerned in terms of a direction and a number of steps. In an embodiment, at block 1006, the computer system correlates each step activity with a direction to determine a distance moved in a particular direction. At block 1008, the computer system generates a breadcrumb report by mapping the distance and direction of travel of each successive step from a known start location. At block 1010, the system determines if GPS data is available, and if GPS data is available, the position predicted by the step activity is corrected to improve the accuracy of the report.

Figure 11:
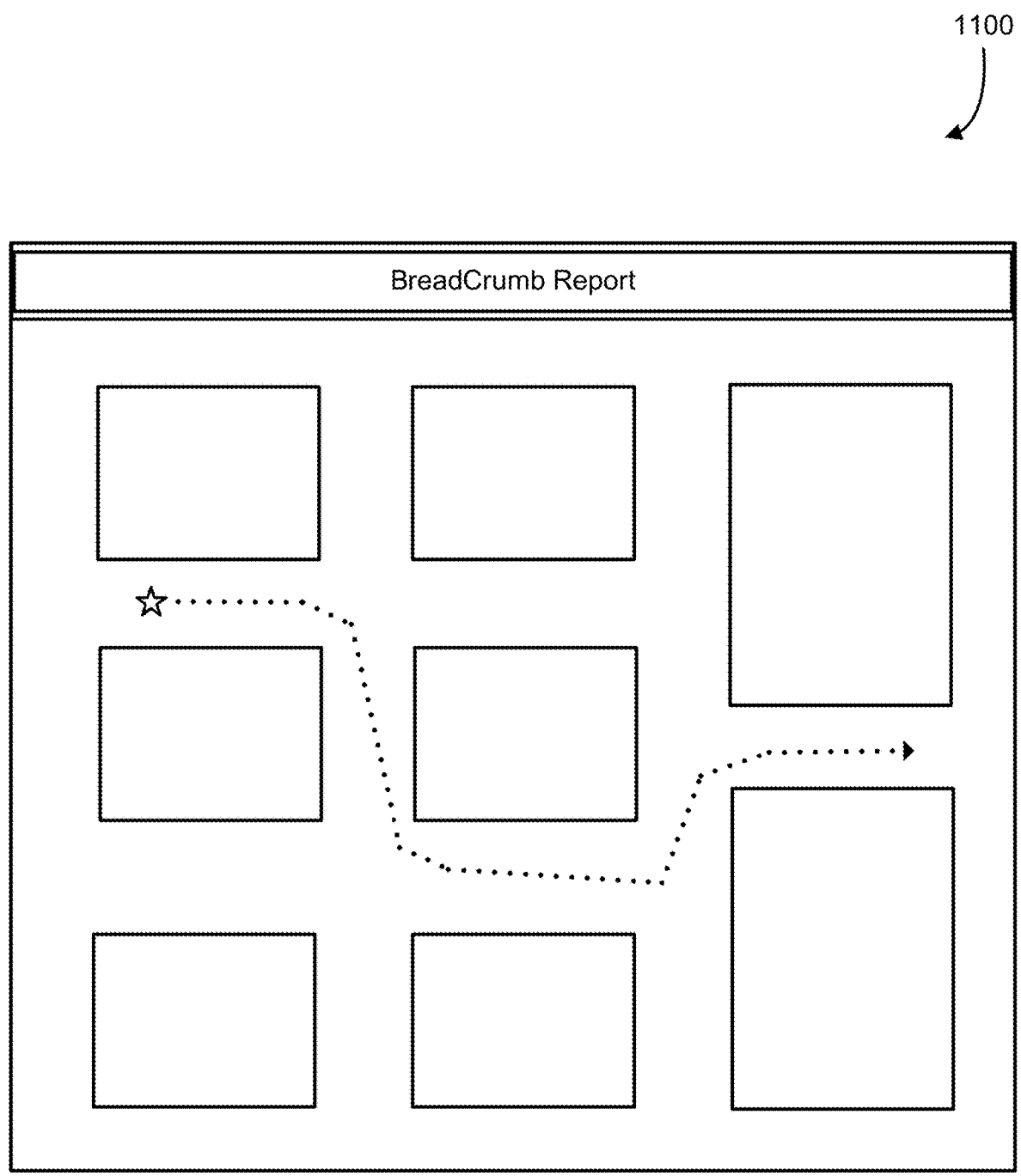
FIG. 11 illustrates an example of a breadcrumb report that shows the movement of the subject, in accordance with various embodiments.

FIG. 11 illustrates an example of a breadcrumb report that shows the movement of the subject, in accordance with various embodiments. A breadcrumb report is the map of the movement of the user either outdoors or indoors. The outdoor breadcrumb report is generated using a GPS chip integrated with the system. For an indoor breadcrumb report, the accuracy of the breadcrumb report may be impaired in many circumstances due to weak global positioning signals. To mitigate against weak signals, in an embodiment, the system uses step counting along with direction measurement (using a magnetometer or other direction sensor) to generate an indoor breadcrumb report. When available, a GPS signal may be used to augment and/or correct the breadcrumb report.

Figure 12:
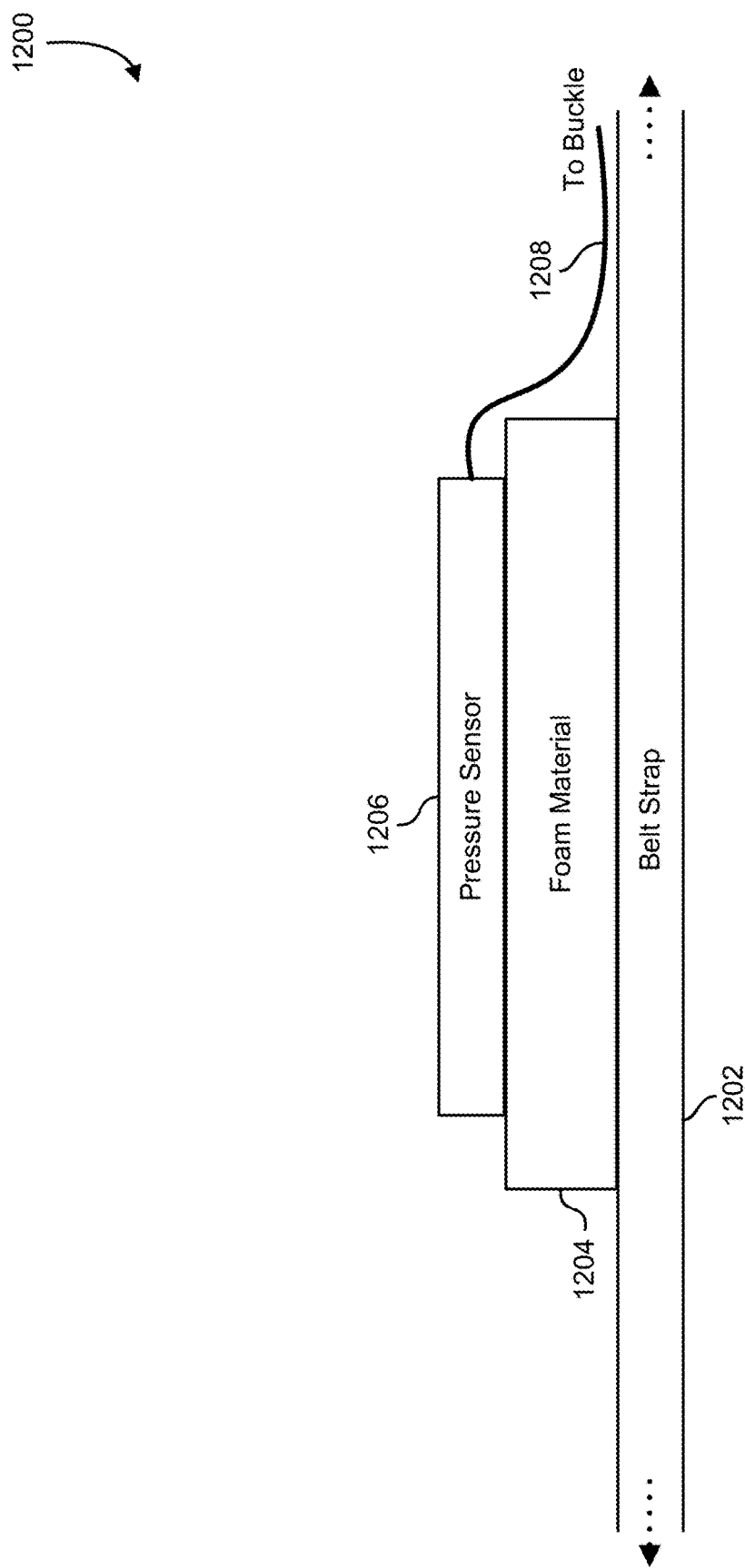
FIG. 12 illustrates an example of a sensor mounted to a belt for determining that strain on the back of a person, in accordance with various embodiments.

FIG. 12 illustrates an example of a sensor mounted to a belt for determining the strain on the back of a person, in accordance with various embodiments. In an embodiment, a belt strap 1202 made of leather, plastic, or other flexible material capable of being wrapped around the subject is fitted with a sensor for measuring the strain on the back of the subject. In an embodiment, a layer of foam material 1204 is attached to the belt strap 1202 using adhesive, mechanical fasteners, hook and loop fasteners, or other attachment methods. A pressure sensor 1206 is attached to the foam material, and a sensor wire 1208 runs from the pressure sensor 1206 to a buckle containing memory for storing sensor data. In some examples, the pressure sensor is a force sensitive resistor ("FSR"). In some embodiments, the pressure sensor 1206 may be mounted directly to the belt strap 1202. In some embodiments, the pressure sensor is a switch that is mounted on the inside of the belt which is depressed when the belt is under sufficient tension. In some examples, the pressure sensor protrudes into the interior of the belt to maintain contact with the wearer even if the belt is loose.

In some examples, measurement of strain directly on a belt may be challenging. In an embodiment, the belt uses FSRs to obtain strain data around the waist of a person. FSRs can sense the amount of pressure applied on their surface, which is proportional to the amount of strain at that location. An advantage of using an FSR is that strain at multiple locations around the back can be measured, which can then be combined with information from other sensors to provide insights on the classification and prediction of various activities, especially the amount of bending, strain on the person's back, and method of bending.

In some embodiments, pressure sensors are used to act as strain sensors. If the wearable device is in the form of a belt that is not in direct contact with the skin, measurement of strain on the waist region of the body may be difficult to achieve directly. However, the information on strain helps determine the risk of injury the wearer is exposed to. To address this limitation, pressures at multiple points on the belt (which is generally to be proportional to strain) is used to model risk of back injury. In various embodiments, there are a number of ways that the accuracy of sensor data collected is improved even if the belt is not being properly worn. In some examples, the wearer is alerted using an LED signal or buzzer that the belt is not aligned correctly or not worn tight enough (based at least in part on information provided by the pressure sensor). In another example, a foamy material placed under the pressure sensors (see the figure below), ensures that the pressure sensor is able to generate some signal even when the belt is somewhat loose (from bending or improper wearing).

Temperature and humidity sensors continuously monitor the temperature and humidity where the employee is working. The temperature and humidity readings will be correlated with productivity and safety to see if temperature or humidity is a dependent factor. In some examples, temperature and humidity monitoring may be used to detect and alert users of abnormal changes in battery temperature and, if necessary, turn off the battery.

Altimeter and motion sensors data will be used to approximately determine when, how long, and at what height a person is working, when he/she is working from heights, be it indoors or outdoors. In various embodiments, this information is used to determine the risk associated with working from heights based at least in part on the number of accidents over a period. Also, this information may be correlated with geographic location, nature of job, and other factors. Height above ground level may be detected using different algorithms based on a known pressure at ground level, atmospheric pressure conditions determined from regional weather, and an atmospheric pressure sensor on the belt. In some embodiments, ultrasonic ranging sensors or a radar altimeter may be used to determine height above the ground level. Working from height, even as low as knee height, may be considered a risk in some environments, and the sensors are able to determine if such a risk exists.

In various embodiments, the system determines the driving habits of the subject wearing the belt. In an embodiment, driving habits of a specific driver are determined using sensors on the belt instead of a device attached to the vehicle. In this way, the driving habits of the driver are established and recorded rather than the vehicle itself. However, in other embodiments, the belt may interface with various sensors on the vehicle in order to collect information such as vehicle speed, airbag deployment, G forces, and fuel usage, relaying this data to a storage server in association with the identity of the driver determined from the belt. In various examples, the system determines time taken by the driver to get out of vehicle after the vehicle is stopped, and time spent and tasks performed before starting the vehicle again will be derived from sensor data.

In various examples, the determination of driver habits is made from the sensor measurements in terms of the number and frequency of various driving parameters such as hard brake, hard acceleration, swerves, driving above speed limit, etc. The sensors in the belt, specifically the accelerometer and the GPS chips, will provide information regarding these activities.

The entry and exit of the driver from the vehicle is classified as an activity, and the number and duration of such activities are recorded.

Figure 13:
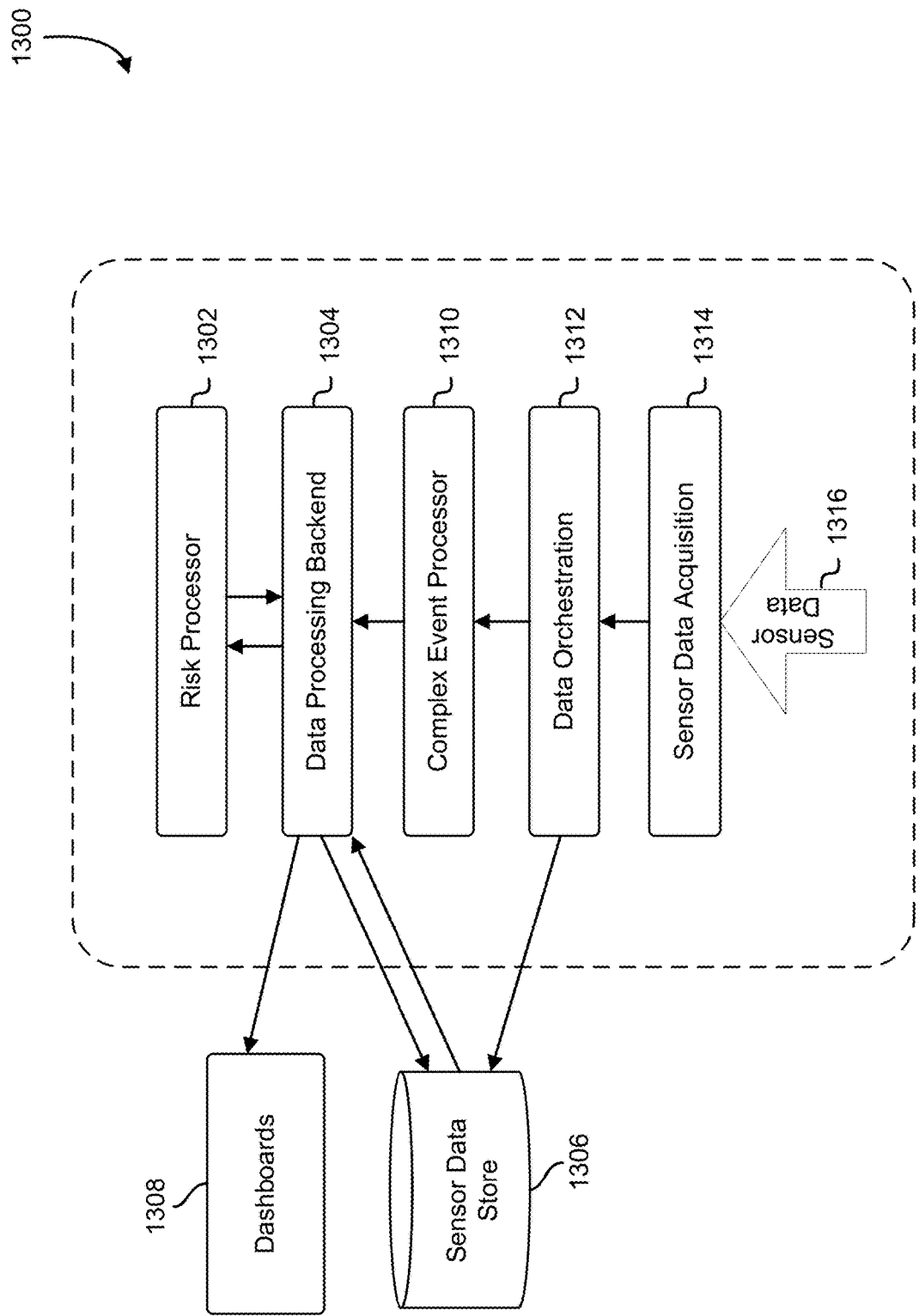
FIG. 13 illustrates an example of a data modeling system that analyzes sensor data to produce a set of reports and dashboards, in accordance with various embodiments.

FIG. 13 illustrates an example of a data modeling system 1300 that analyzes sensor data to produce a set of reports and dashboards, in accordance with various embodiments. In an embodiment, the system includes a risk processor 1302, the data processing backend 1304, a complex event processor 1310, a data orchestration component 1312, and a sensor data acquisition component 1314. The system analyzes sensor data 1316 which is stored in a sensor data store 1306 to produce a set of dashboards 1308.

In an embodiment, data analysis models for activity classification are based at least in part on a collection of distributed sensors on an electronic device, such as a belt described in the present document. In some examples, a collection of distributed sensors is used to classify workplace events such as slips, trips, falls, collisions, walking, running, lifting weights, drilling, painting, pushing, pulling heavy objects and so on. When a belt containing the sensors is worn by a user, the sensors, which may include sensors such as an accelerometer, gyroscope, magnetometer, pressure sensor, and altimeter, start capturing sensor data 1316. The sensor data 1316 is collected by the sensor data acquisition component 1314. In an embodiment, the sensor data is transferred to the sensor data store 1306 via the data orchestration component 1312. In some embodiments, the sensor data store 1306 is a storage service accessible via an online service.

In an embodiment, raw signals are processed using mathematical models and algorithms developed for activity classification. Raw signals are filtered and smoothed. Signals are segmented into windows. Time and frequency domain features are calculated for each window. The input is sent to the activity classification model, which has been trained to recognize activities. Using the model, the signal is classified into one of a set of pre-defined classes of activities. Performance metrics (for example step count for walking, jogging, running, upstairs, and downstairs) are calculated for each activity.

In an embodiment, the sensor data acquisition component 1314 receives messages via MQTT using a publisher/subscriber model. In an embodiment, the data orchestration component 1312 listens to IoT Paas, and categorizes and pushes data forward to a relevant endpoint in the complex event processor 1310. In an embodiment, the complex event processor 1310 aggregates sensor events and categorizes the data before forwarding the data to the data processing backend 1304. In an embodiment, the data processing backend 1304 is implemented using JavaScript and provides API endpoints for the front-end and API consumers. In an embodiment, the data processing backend 1304 preprocesses data for the mathematical models. In an embodiment, the risk processor 1302 implements mathematical models that predict risk using preprocessed sensor data provided by the data processing backend 1304.

Figure 14:
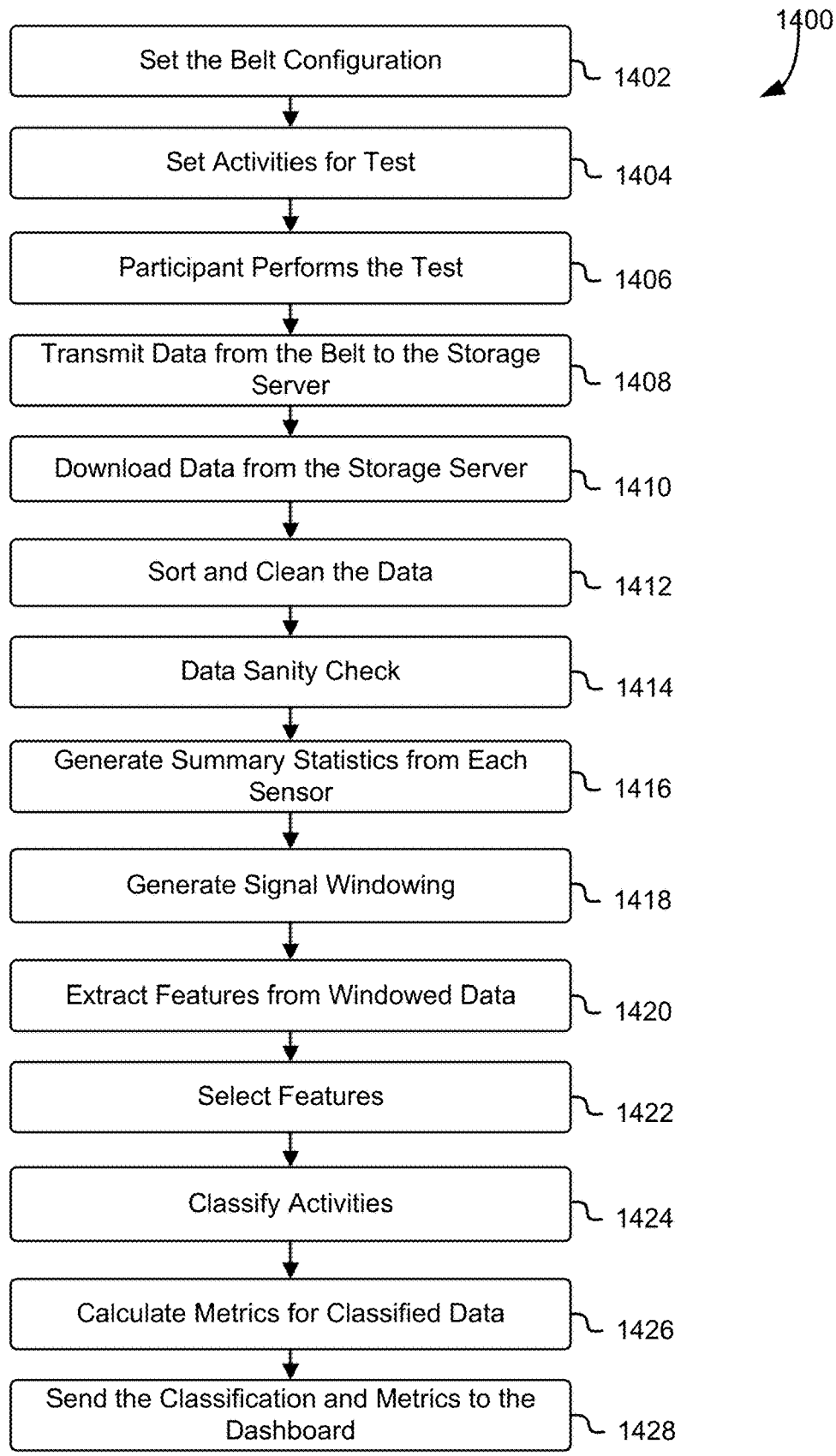
FIG. 14 illustrates an example of a process that, as a result of being performed by a sensor data collection system, produces activity classifications and metrics that are presented to an administrator, in accordance with various embodiments.

FIG. 14 illustrates an example of a process 1400 that, as a result of being performed by a sensor data collection system, produces activity classifications and metrics that are presented to an administrator, in accordance with various embodiments. The process begins at block 1402 where the system sets the configuration of a belt containing a collection of sensors that collects sensor data associated with the activities of a subject wearing the belt. At block 1404, the system selects a collection of activities that are to be classified. At block 1406, while wearing the belt, the participant performs the activities to be tested. The data collected from the sensors on the belt while the test is performed is transmitted 1408 from the belt to a storage server. In an embodiment, at block 1410, the data stored on a storage server is downloaded to an analysis server. At block 1412, the analysis server sorts and cleans the data and performs 1414 a data sanity check. Data that is out of range or clearly an error is removed. In an embodiment, at block 1416, the system generates summary statistics for each sensor. At block 1418, the system generates signal windows over which the sensor data is to be processed. Features are extracted 1420 from the windowed sensor data. At block 1422, a set of features is selected. In an embodiment, at block 1424, the system classifies the activities detected during the processing of the sensor data. At block 1426, metrics are calculated for the classified data. In some examples, the classified data is processed to generate one or more reports or other data summaries. At block number 1428, the classifications, metrics, and reports are sent to an administrative console where they are displayed to the user such as a manager or administrator.

Figure 15:
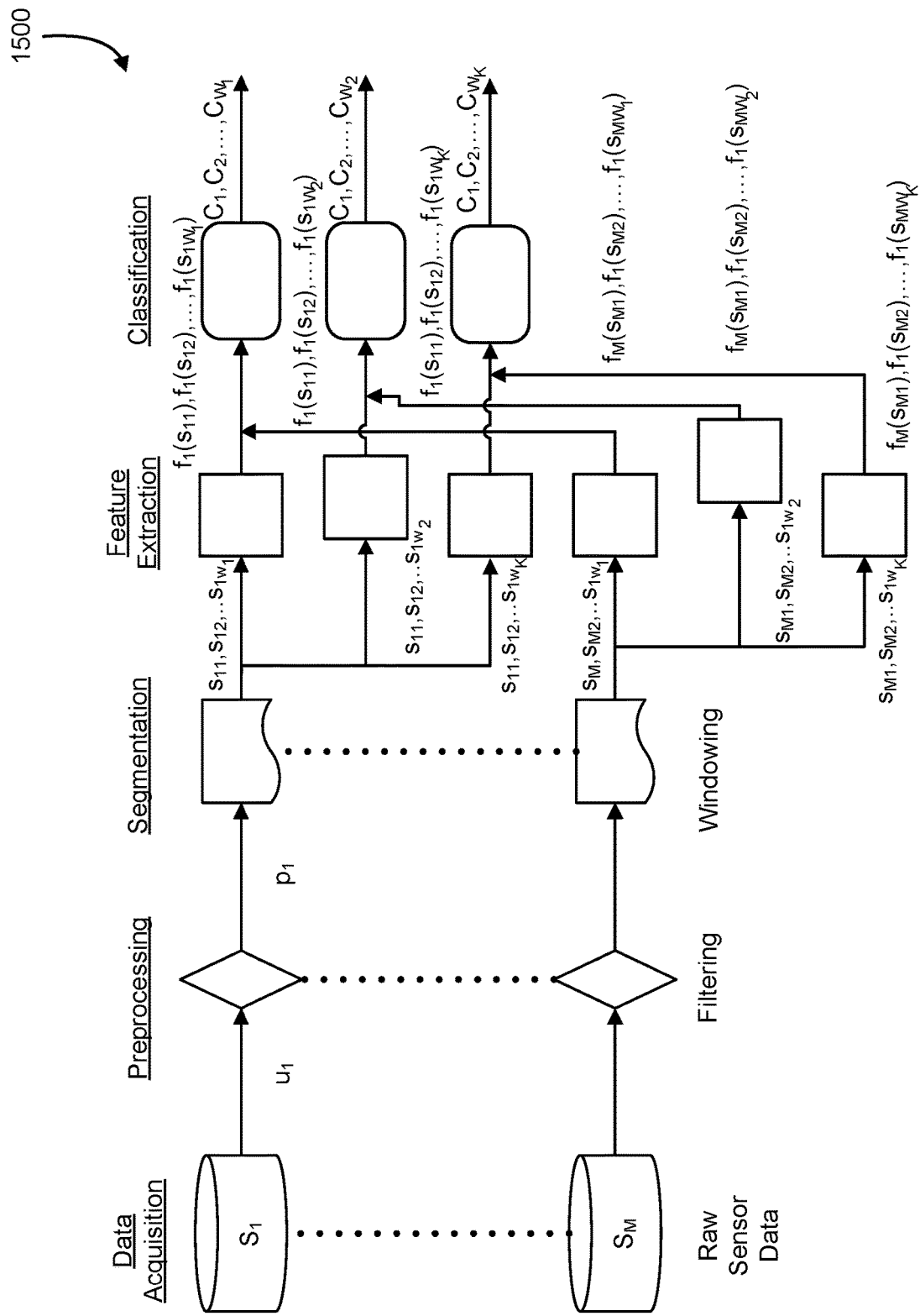
FIG. 15 illustrates an example of a machine learning process 1500 that produces activity classifications and metrics, in accordance with various embodiments.

FIG. 15 illustrates an example of a machine learning process 1500 that produces activity classifications and metrics, in accordance with various embodiments. In an embodiment, the process includes a unique activity recognition algorithm. In the unique activity recognition algorithm, each set of activities brings a different pattern recognition problem. For example, discriminating between walking, running, and standing still is much easier than incorporating more complex activities such as watching TV, eating, ascending, and descending. The system analyzes a unique set of activities including more complex tasks such as bending in different directions, back extensions and so on.

In an embodiment, the system selects a window length for processing. The window length is determined by dividing the measured time series in time windows to relax the human activity recognition problem. In an embodiment, the selection of the window length is important because the computational complexity depends on the number of samples processed. In some examples, by providing rather narrow windows, performance is enhanced but entails higher overhead due to the recognition algorithm being triggered more frequently. In addition, short time windows may not provide sufficient information to fully describe the performed activity. In other examples, if the windows are excessively long, there may be more than one activity within a single time window. In an embodiment, the system uses optimization algorithms to find the optimal length of the window to provide both recognition quality and processing efficiency.

Figure 16:
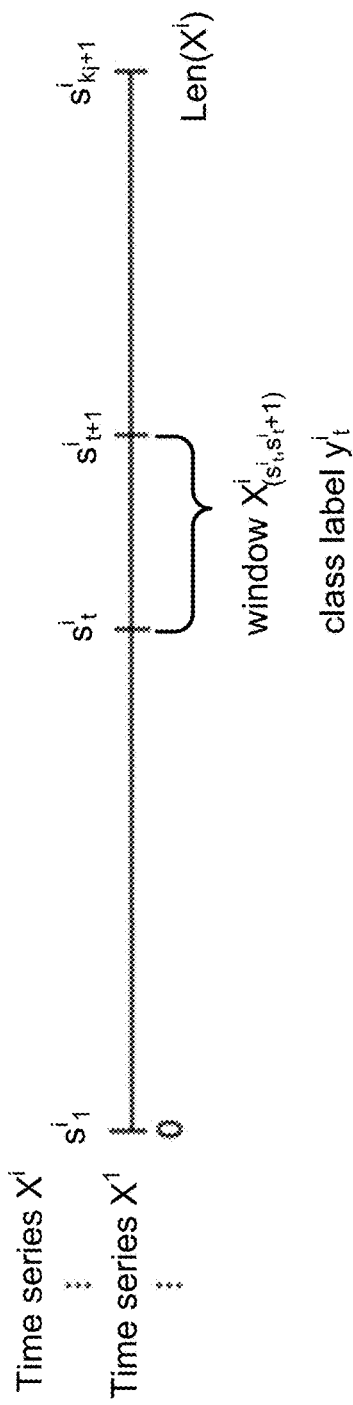
FIG. 16 illustrates an example of change points between activities $s_1^i, \ldots, s_{k_i+1}^i$ and the class labels $s_t^i$ provided, in accordance with an embodiment.

FIG. 16 illustrates an example of change points between activities $s_1^i, \ldots, s_{k+1}^i$ and the class labels $s_t^i$ provided, in accordance with an embodiment. In an embodiment, once the weight vectors $\{w_j\}$ have been learned through the training of the classification algorithm, the weight vectors are used to segment unseen time series X by finding a set of change points $S_1, \ldots, S_{k+1}$ such that:

$$\text{minimize}_{k,s_t,y_t,\varepsilon_t} \sum_{t=1}^{k} \varepsilon_t$$

subject to: $l_{min} \leq s_{t+1} - s_t \leq l_{max} \; \forall \, t, s_1 = 0, s_{k+1} = len(X),$ $(w_{y_t} - w_y)^T \varphi(X_{(s_t, s_{t+1})}) \geq 1 - \varepsilon_t \; \forall \, t, y \neq y_t$ Observe that the number of windows k is not known in advance and, therefore, needs to be optimized over. In the above formulation, $l_{min}$ and $l_{max}$ are the minimum and maximum lengths of windows, which can be inferred from training data. $w_y^T \varphi(X_{s_t,s_{t+1}})$ is the classification score for assigning window $X_{(s_t,s_{t+1})}$ to classy. The system operates to maximize the difference between the classification score of the winning class $y_t$ and that of any other class $y \neq y_t$, filtering through the Hinge loss. The system seeks a windowing technique in which each resulting window is assigned a class label with acceptable confidence.

Figure 17:
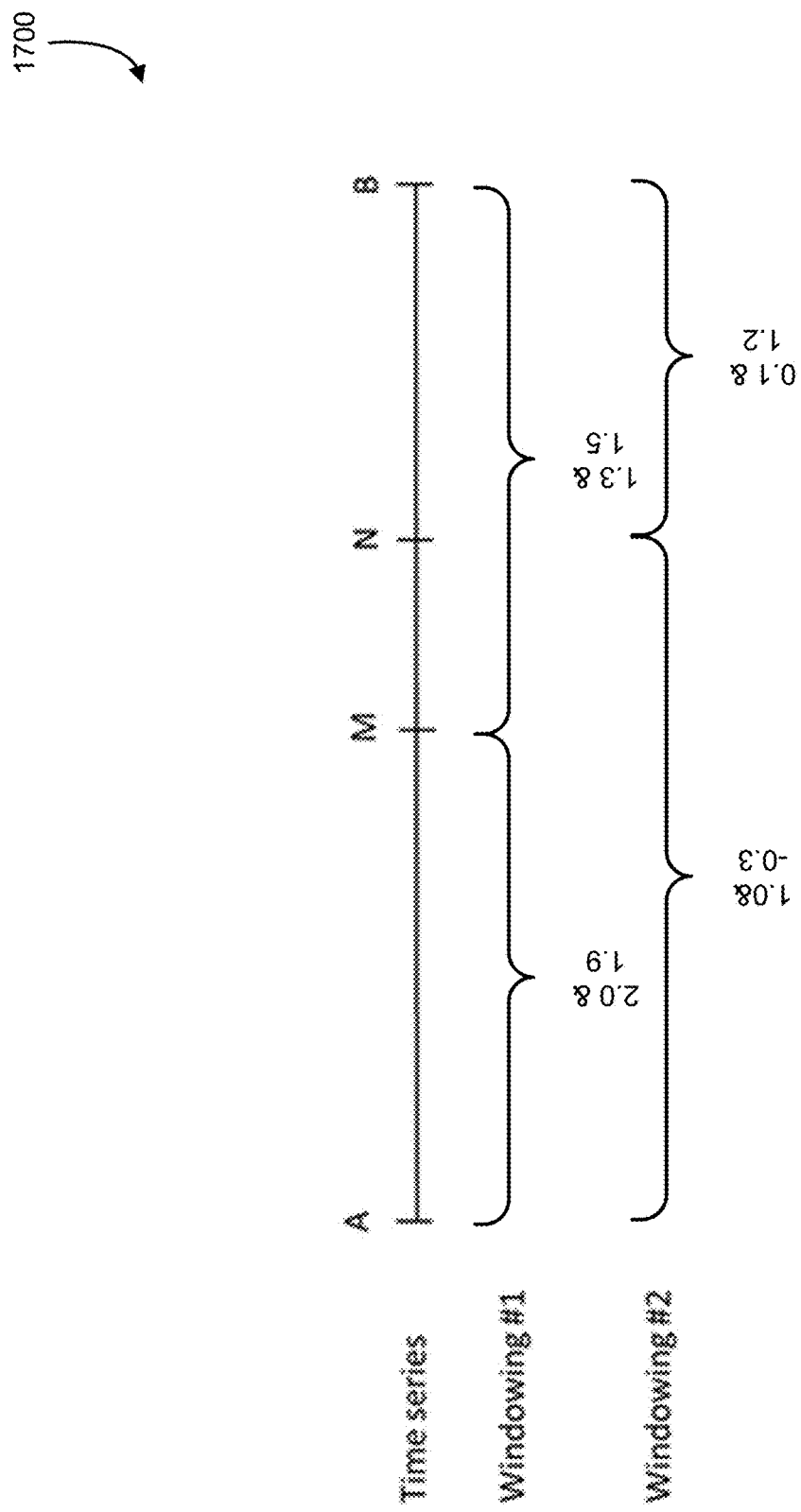
FIG. 17 illustrates an example of a windowing technique in accordance with an embodiment.

In an embodiment, windowing criterion (see the equation above) involves suppressing the non-maximum classes. To see the difference between these two criteria, consider breaking a time series AB in FIG. 17 at either M or N. For simplicity in the explanation, suppose there are only two classes, and the classification scores of the first and second class for some segments in FIG. 17 are shown separately. Consider the segment AM, even though the classification score of the winning class, class 1, is high, the classification score of the alternative, class 2, is also similarly high. The criterion used by the system seeks the optimal segmentation that maximizes the difference between the classification scores of the winning class and the next best alternative, filtering through the robust Hinge loss.

FIG. 17 illustrates an example of a windowing technique in accordance with an embodiment. In the example shown in FIG. 17, the problem presented is which windowing technique is preferred, breaking time series AB at M or N? Suppose there are only two classes, classification scores of the first and second class for corresponding segments are printed separated by a & symbol, in order. The windowing criterion of the system prefers to cut at N because the resulting segments can be confidently classified.

In an embodiment, features are selected using "minimum mutual information" between features as criteria for minimum redundancy and the maximal mutual information between the classes and features. Combined with the Correlation-based Feature Selection ("CFS") approach, CFS works under the assumption that features should be highly correlated with the given class but uncorrelated with each other.

Various algorithms may be utilized, such as Sparse Group LASSO Least absolute shrinkage and selection operator ("LASSO") regression [Tibshirani, 1994].

$\min\{|Ax-Y|+\lambda_1|x|_1\}$

In another example, sparse learning with efficient projections ("SLEP") may be used [Liu, 2011].

$\lambda 1, \lambda 2$: regularization parameters for group sparsity $\min(|Ax-Y|+\lambda_1|x|_1+\lambda_2 \Sigma_{i=1}^g w_i^g |xG_i|_2)$ $A \in R^{m \times n}, y \in R^{m \times 1}, x \in R^{n \times 1}$ x is divided by g non-overlapping groups In an embodiment, information theory is integrated with regularized sparse learning optimization for optimal feature selection. MI ranking finds the most informative features by capturing the nonlinear dependency to the class without any assumption about nature of the relationship.

$I(X;Y) = ZY\,ZX\,p(x,y)\log[p(x,y)/p(x)p(y)]d(x)d(y)$ p(x,y)=joint probability density function of X and Y
p(x),p(y)=marginal probability density function of X and Y (M) features based on MI and then (K) features with LASSO or SGL In an embodiment, the system provides clear visual reports of the above events on a time scale. In some examples, there are two main types of screens on the dashboard.

In some examples, there are screens that contain performance and safety related information. These screens are updated dynamically. Throughout the day, different performance measurements are calculated and the dashboard is updated every 30 minutes. In some implementations, these screens provide both dynamic information that gets updated during the day, every 30 minutes, as well as historical data, going back as far as three months ago.

In additional examples, there are screens that are primarily used to change the settings and set-ups.

Figure 18:
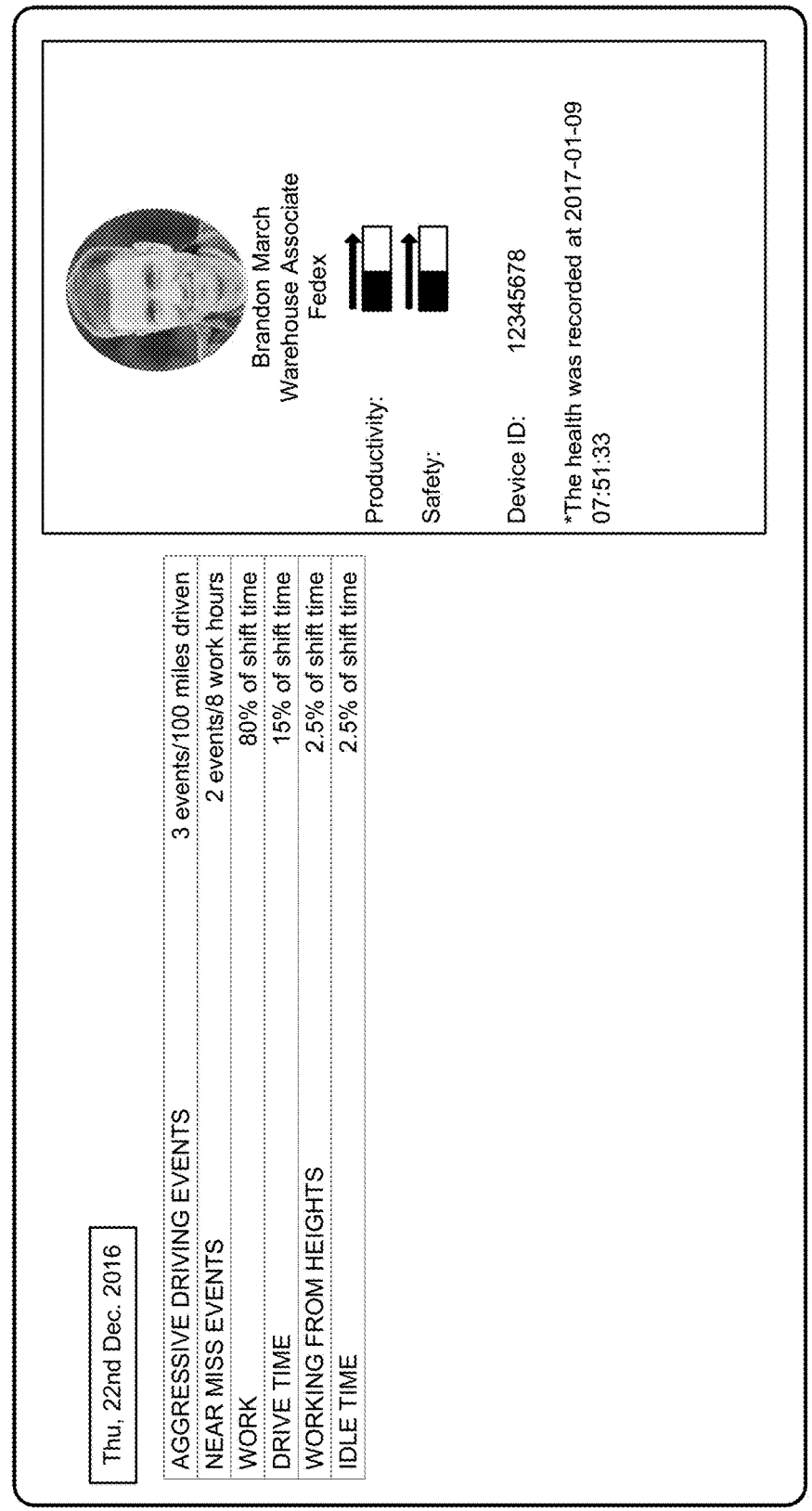
FIG. 18 illustrates an example of a user interface that shows an employee scorecard in accordance with an embodiment.

FIG. 18 illustrates an example of a user interface that shows an employee scorecard in accordance with an embodiment. On the employee scorecard screen, each employee is able to see a summary of their daily performance. The scorecard gives a summarized report of the number of aggressive driving behaviors that happened on a selected day. Using the scorecard, a user can see how many near-miss events the employee had including falls, slips, and trips. Total time an employee spends at work is divided into three groups: work, idle, and driving time.

Figure 19:
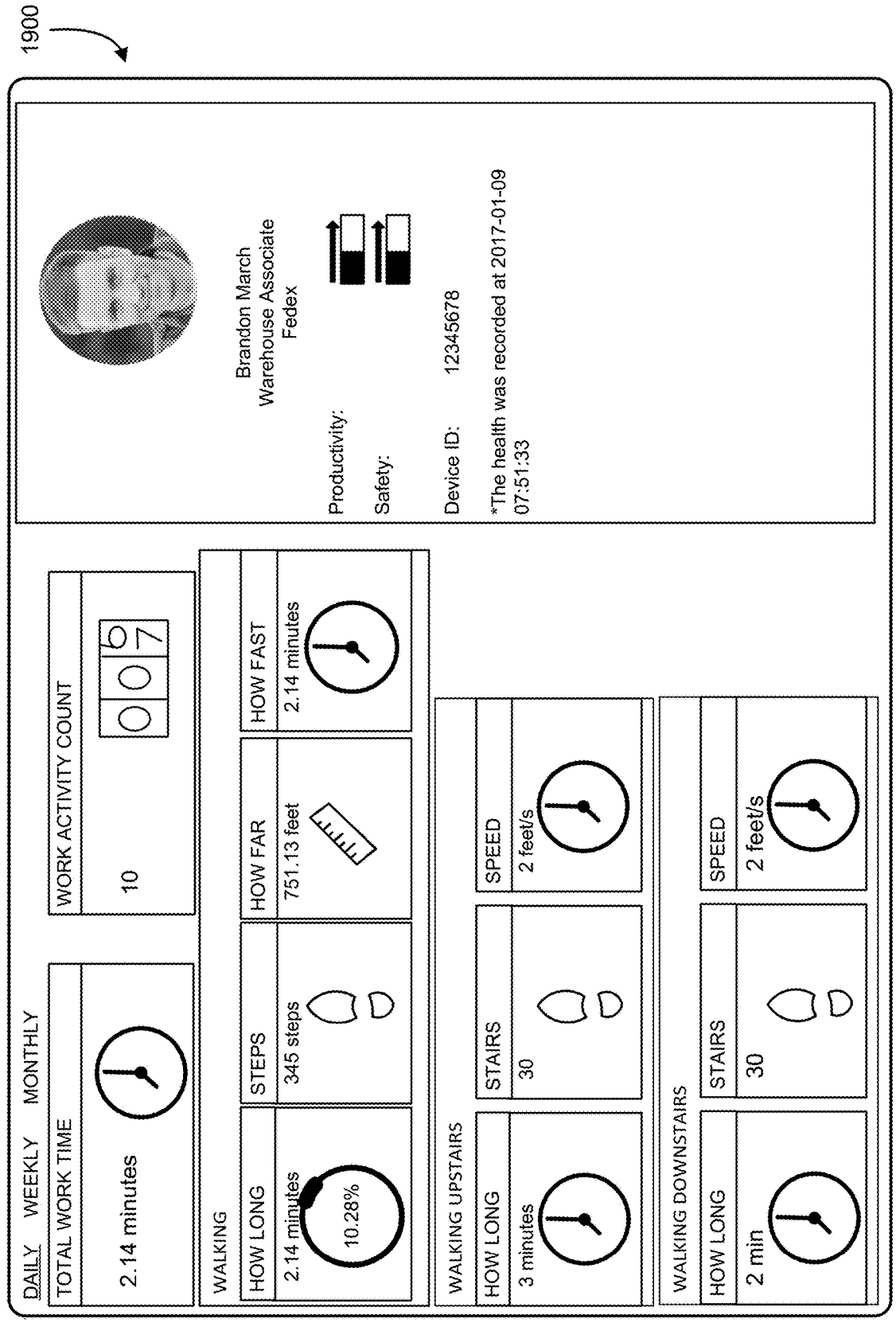
FIG. 19 illustrates an example of a user interface that shows an employee dashboard in accordance with an embodiment.

FIG. 19 illustrates an example of a user interface that shows an employee dashboard in accordance with an embodiment. On the employee dashboard, navigating to the productivity tab, the employee can access the "work" section to see metrics pertaining to different activities such as walking, walking upstairs, walking downstairs, running, etc. The metrics for walking are an aggregate of how long the employee walked, how many steps he took, how far he walked and how fast he walked. For walking upstairs and downstairs, the metrics are how long the employee took to climb/get down the stairs, how many steps he took, and what the speed of ascend/descend was. The metrics for running are similar to the metrics for walking.

Figure 20:
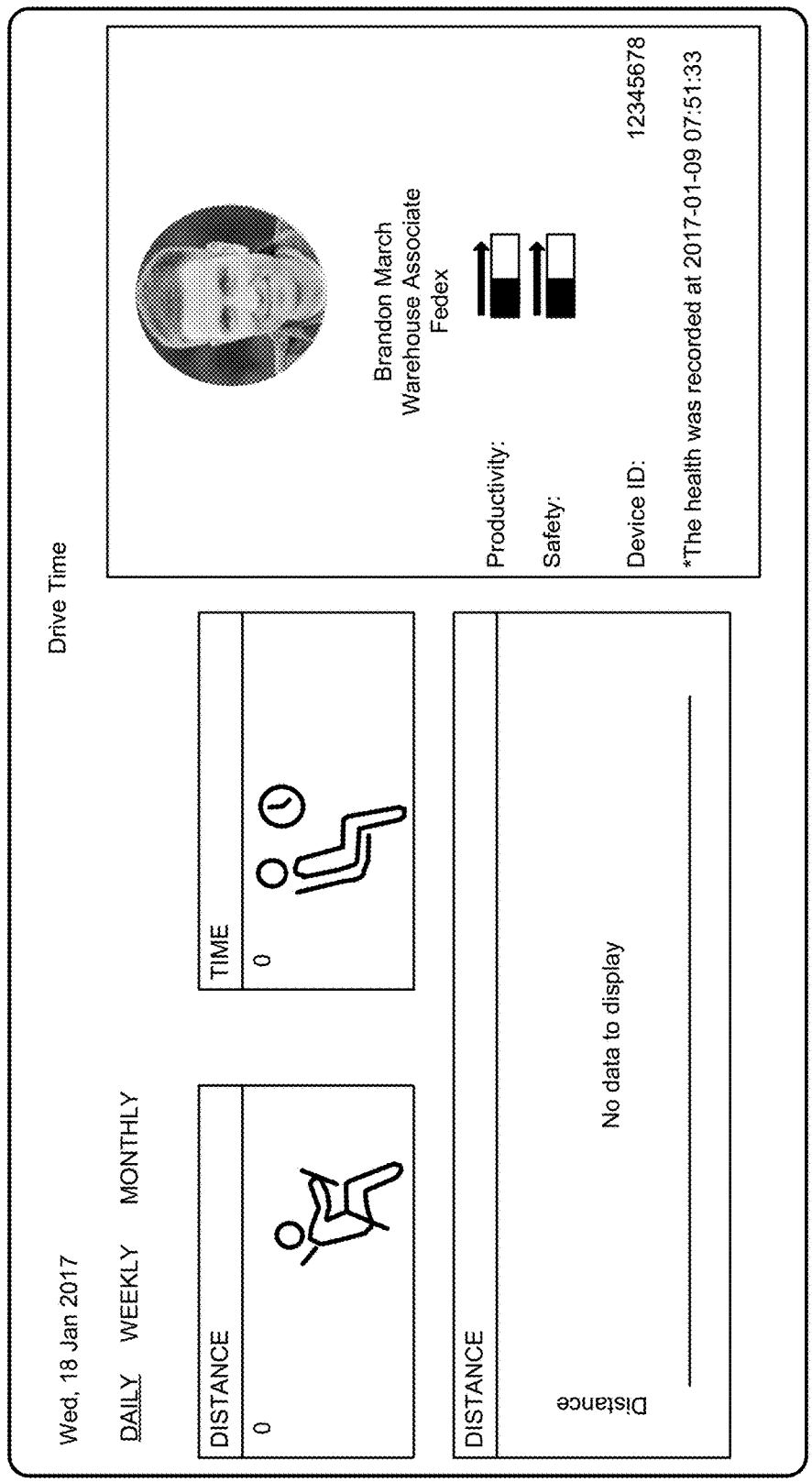
FIG. 20 illustrates an example of a user interface that shows driving activities of an employee in accordance with an embodiment.

FIG. 20 illustrates an example of a user interface that shows driving activities of an employee in accordance with an embodiment. On the employee dashboard, navigating to the productivity tab, in the work section the employee can see different metrics pertaining to their driving activity. The metrics related to driving are the total distance the employee drove, total time he took for getting there and a graph of the distance of how far he drove.

Figure 21:
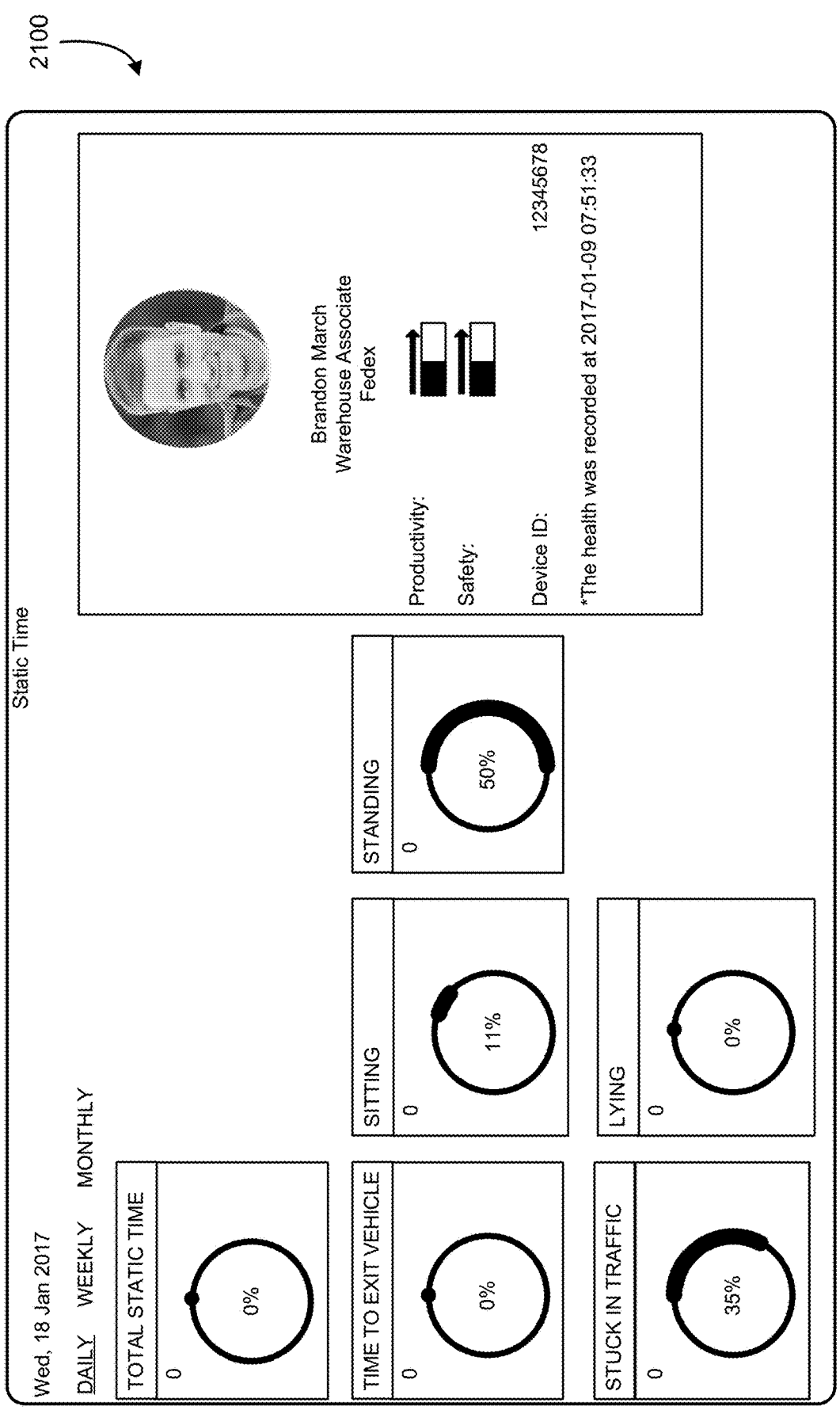
FIG. 21 illustrates an example of a user interface that shows the static time of an employee in accordance with an embodiment.

FIG. 21 illustrates an example of a user interface that shows the static time of an employee in accordance with an embodiment. On the employee dashboard, navigating to the productivity tab, in the work section the employee can see information pertaining to the idle time, which is when the employee doesn't do anything. The employee can see the total idle time in his entire shift and the breakdown. The breakdown includes time spent exiting the vehicle, the time spent sitting idle, standing, stuck in traffic, idling, etc. Beside every tab the employee can also see the percentage of total time spent doing that particular activity.

Figure 22:
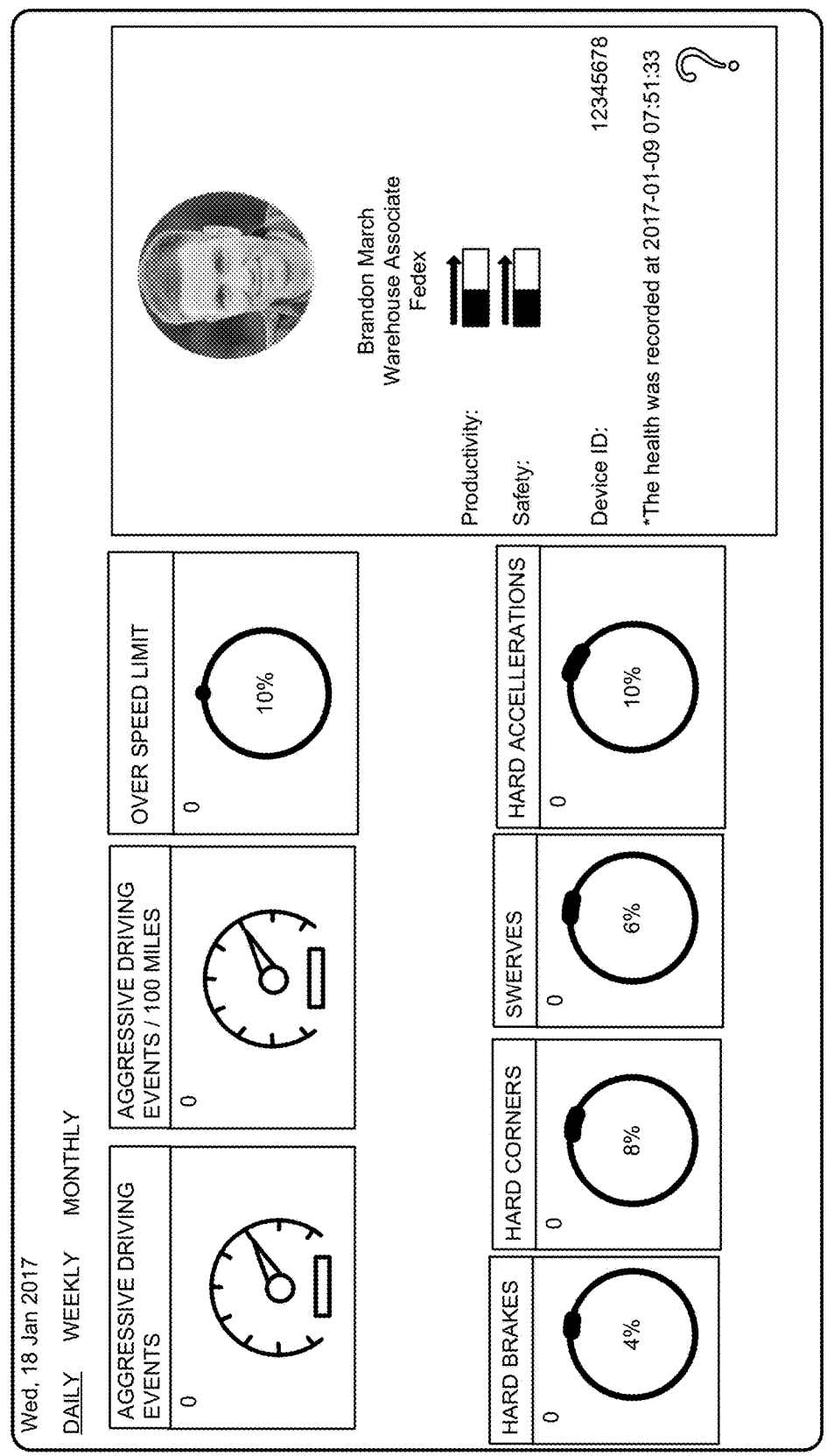
FIG. 22 illustrates an example of a user interface that shows the aggressive driving events of an employee in accordance with an embodiment.

FIG. 22 illustrates an example of a user interface that shows the aggressive driving events of an employee in accordance with an embodiment. On the employee dashboard, navigating to the safety tab, in the daily section the employee can see different metrics pertaining to the safety of their driving activity. The metrics include the total number of aggressive driving events, the number of aggressive events per 100 miles, how many times the employee was driving above the speed limit, number of hard brakes, number of hard corners, number of swerves, and number of hard accelerations. Similarly, the employee can switch the tab between daily, weekly, and monthly to see the all the above metrics tabulated by day, week and month respectively.

Figure 23:
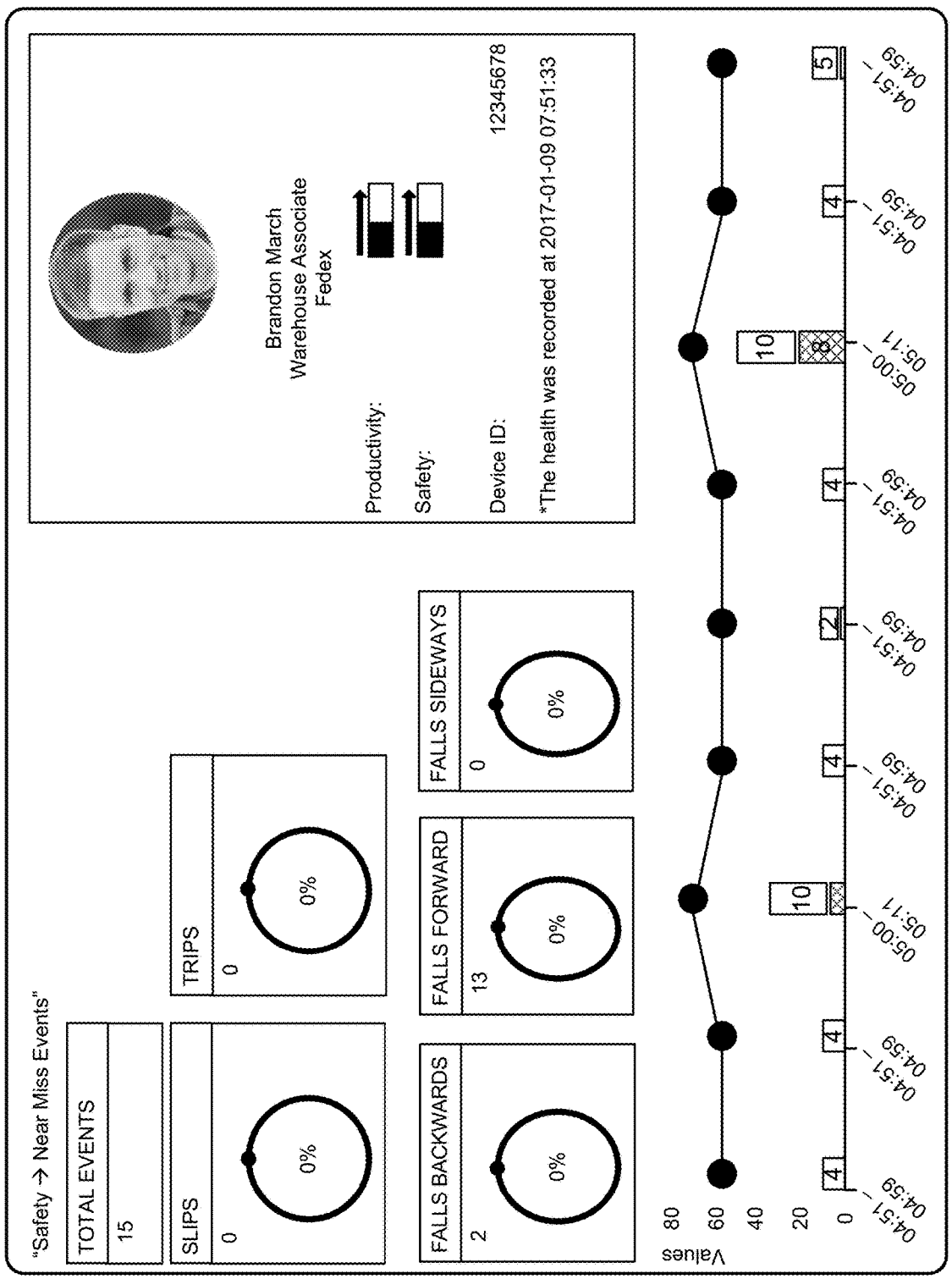
FIG. 23 illustrates an example of a user interface that shows the near miss events of an employee in accordance with an embodiment.

FIG. 23 illustrates an example of a user interface that shows the near-miss events of an employee in accordance with an embodiment. On the employee dashboard, going to the safety tab, in the near-miss events display the employee can see different metrics pertaining to their safety in their work environment. In an embodiment, these metrics include the number of slips, trips, falls backward, falls forward, and falls sideways. The "total events," in an embodiment, is the total sum of all the above near-miss events. In every individual tab, there is a small pie chart which indicates the percent of total near-miss event that particular tab contributed. Below the tabs is a graph which summarizes the total number of near-miss events which occurred in the space of every 10 minutes separated by color. It also shows the graph temperature spaced 10 minutes apart.

Figure 24:
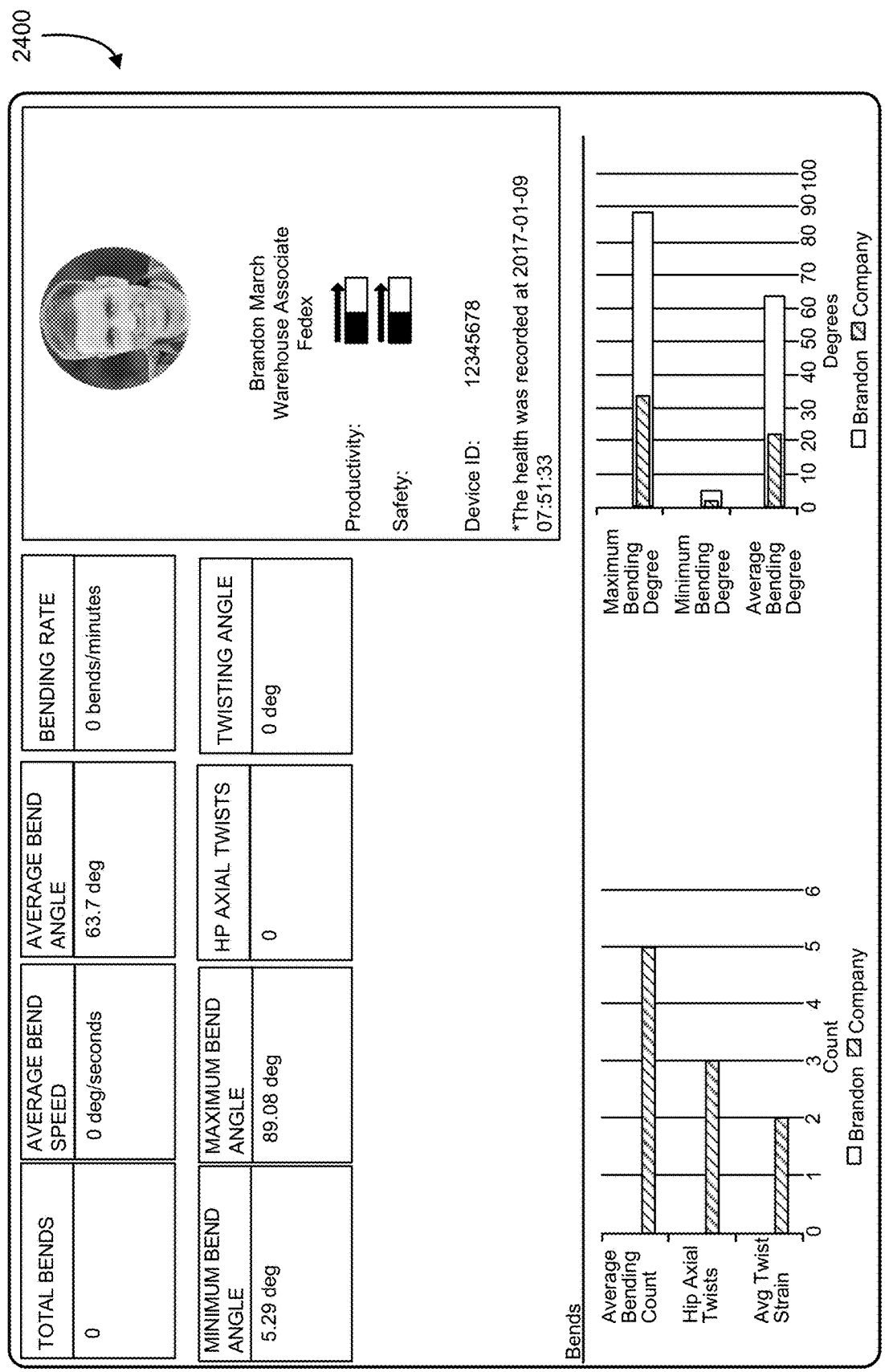
FIG. 24 illustrates an example of a user interface that shows the bending activities of an employee in accordance with an embodiment.

FIG. 24 illustrates an example of a user interface that shows the bending activities of an employee in accordance with an embodiment. On the employee dashboard, going to the safety tab, in the bending tab the employee is able to see different metrics pertaining to their safety while bending in their work environment. In an embodiment, the metrics include the total number of bends, the average bend speed measured in bend/seconds, the average bend angle measured in degrees, the bending rate measured in bends per minutes, the minimum and the maximum bend angle measured in degrees, the hip axial twists and the twisting angle measured in degrees. Below these tabs we are comparing graphically the employee's stats as compared to the company's average stats separated by tabs, which will give a pictorial representation of how much the employee is working.

Figure 25:
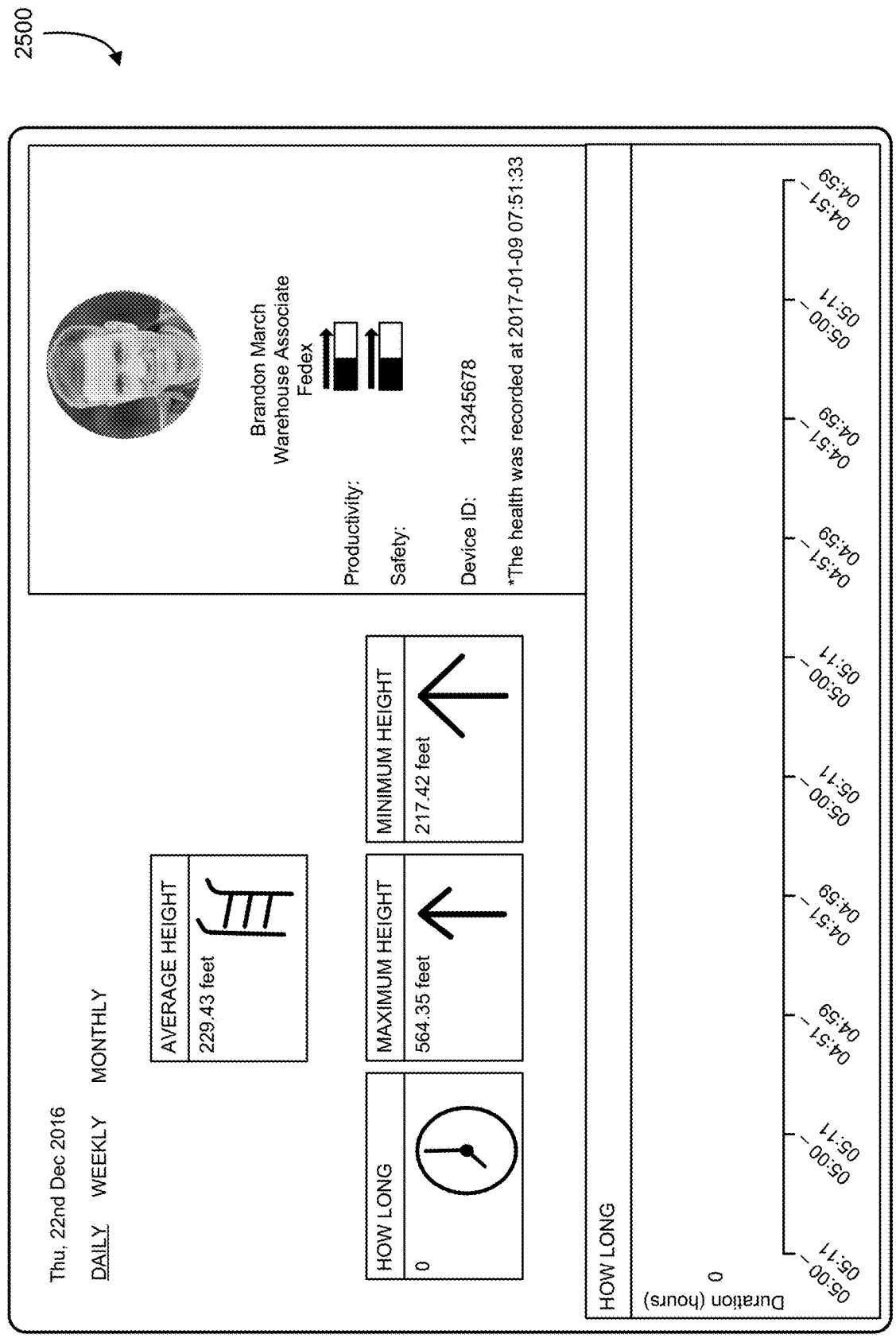
FIG. 25 illustrates an example of a user interface that shows the working from heights activities of an employee in accordance with an embodiment.

FIG. 25 illustrates an example of a user interface that shows the working from heights activities of an employee in accordance with an embodiment. On the employee dashboard, navigating to the safety tab, in the bending tab the employee is able to see different metrics pertaining to their safety in working from heights in their work environment. In an embodiment, the metrics that are calculated are the average height the employee has worked from as expressed in feet. The interface also provides the total time and the maximum and minimum height from which the employee has worked. Below these tabs, there is a graphical representation of the duration the employee worked from height for every hour. There are tabs for weekly and monthly which display the same information as mentioned above.

Figure 26:
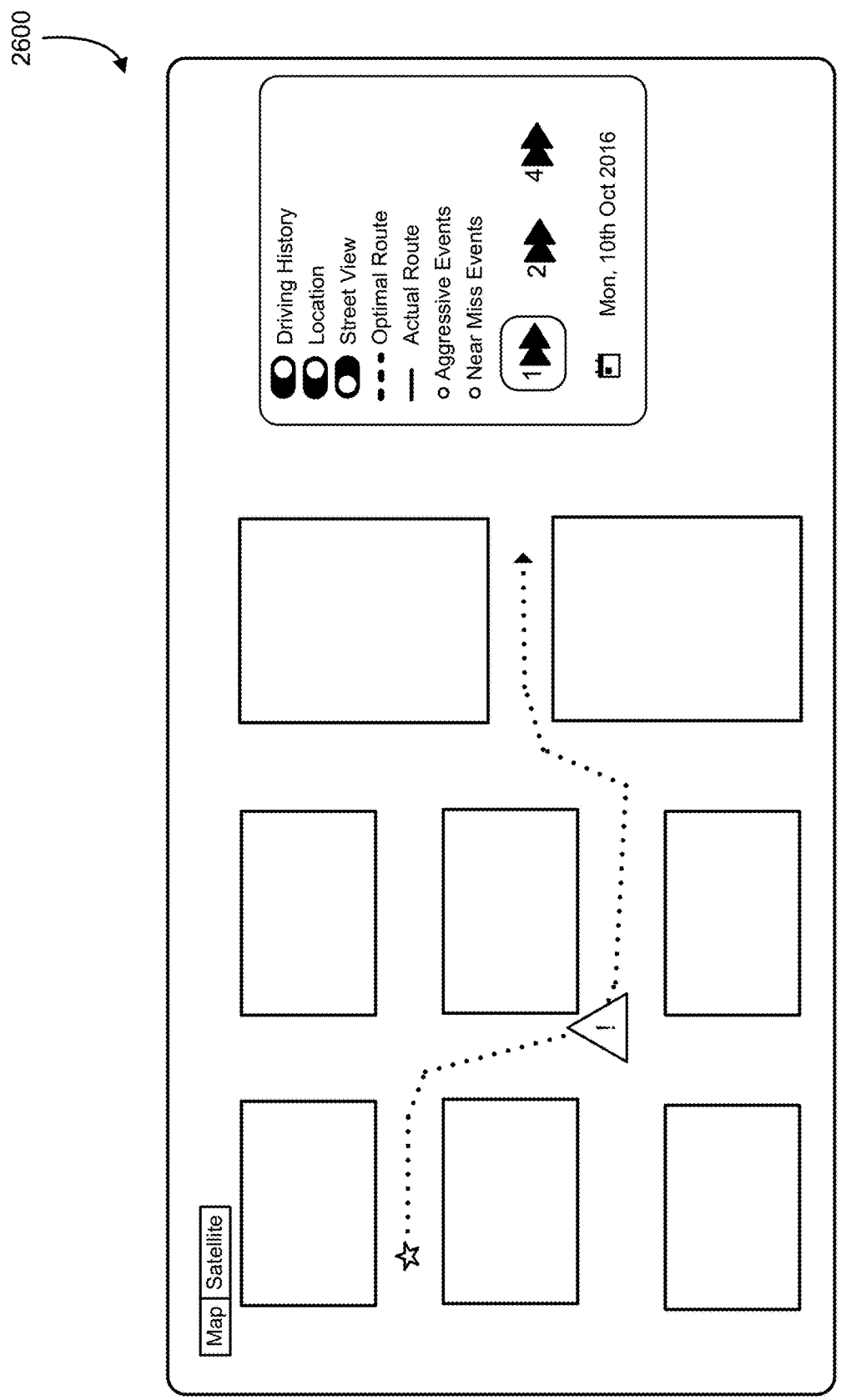
FIG. 26 illustrates an example of a user interface that shows the movement of an employee in accordance with an embodiment.

FIG. 26 illustrates an example of a user interface that shows the movement of an employee in accordance with an embodiment. On the employee dashboard, going on the breadcrumb tab, a user can see the map of the area in which the employee is working. On the top right, the user is able to activate a toggle to view the driving history, locations and street view. If the user toggles on the driving history, we can see the optimal route that could have been taken by the employee. It also shows the route the employee actually took. In the actual route, there are small red dots indicating where the aggressive events happened. There are also small yellow dots, indicating where the near-miss events happened. The employee can also view his route in fast forward mode. In an embodiment, the display offers three options, which are 1× (normal speed), 2× (two times the normal speed) and 4× (four times the normal speed). On the top left side, there is an option to switch between map and satellite view. On the bottom right there is an option to zoom in or zoom out the map.

Figure 27:
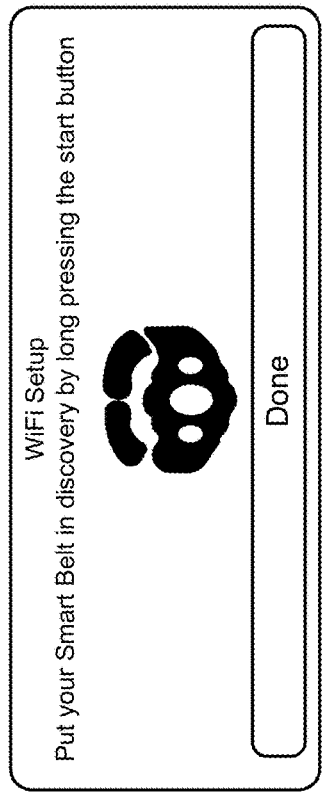
FIG. 27 illustrates an example of a user interface to connect a belt to a WiFi network in accordance with an embodiment.

FIG. 27 illustrates an example of a user interface to connect a belt to a WiFi network in accordance with an embodiment. This tab allows the employee to connect the belt to the WiFi. The employee places the belt in the discovery mode by pressing the start button on the belt. Once this is done, the user presses the "done" button on this page.

Figure 28:
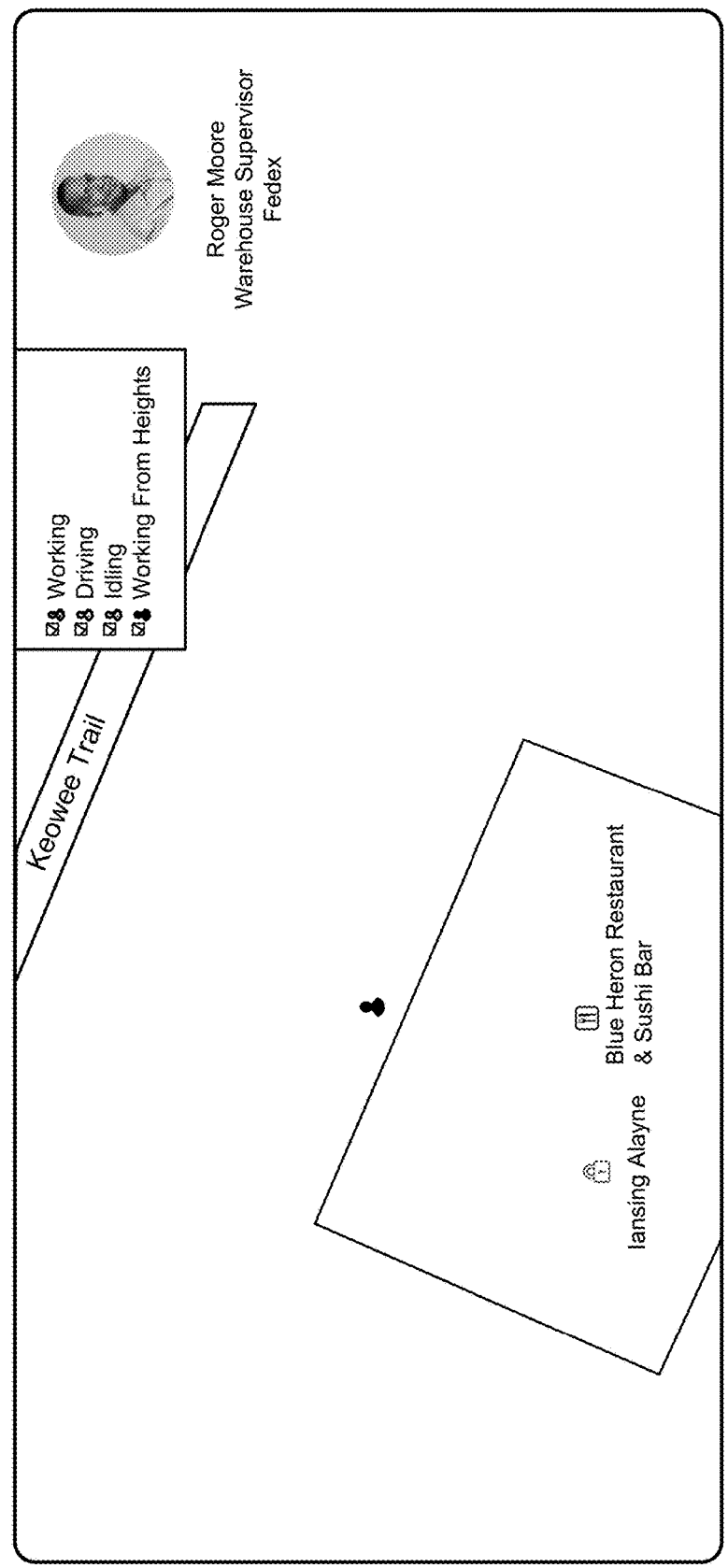
FIG. 28 illustrates an example of a supervisor dashboard in accordance with an embodiment.

FIG. 28 illustrates an example of a supervisor dashboard in accordance with an embodiment. On the supervisor dashboard, in the NOW tab, the supervisor is provided with real-time updates of what the employees are doing at that particular time. The supervisor is provided with the map of the warehouse, with all employees indicated on the map. In an embodiment, the employees are marked with a color: green indicates working, red indicates driving, blue indicates idling, and yellow indicates the employee is working from height. On the top left the supervisor can switch between map and satellite view.

Figure 29:
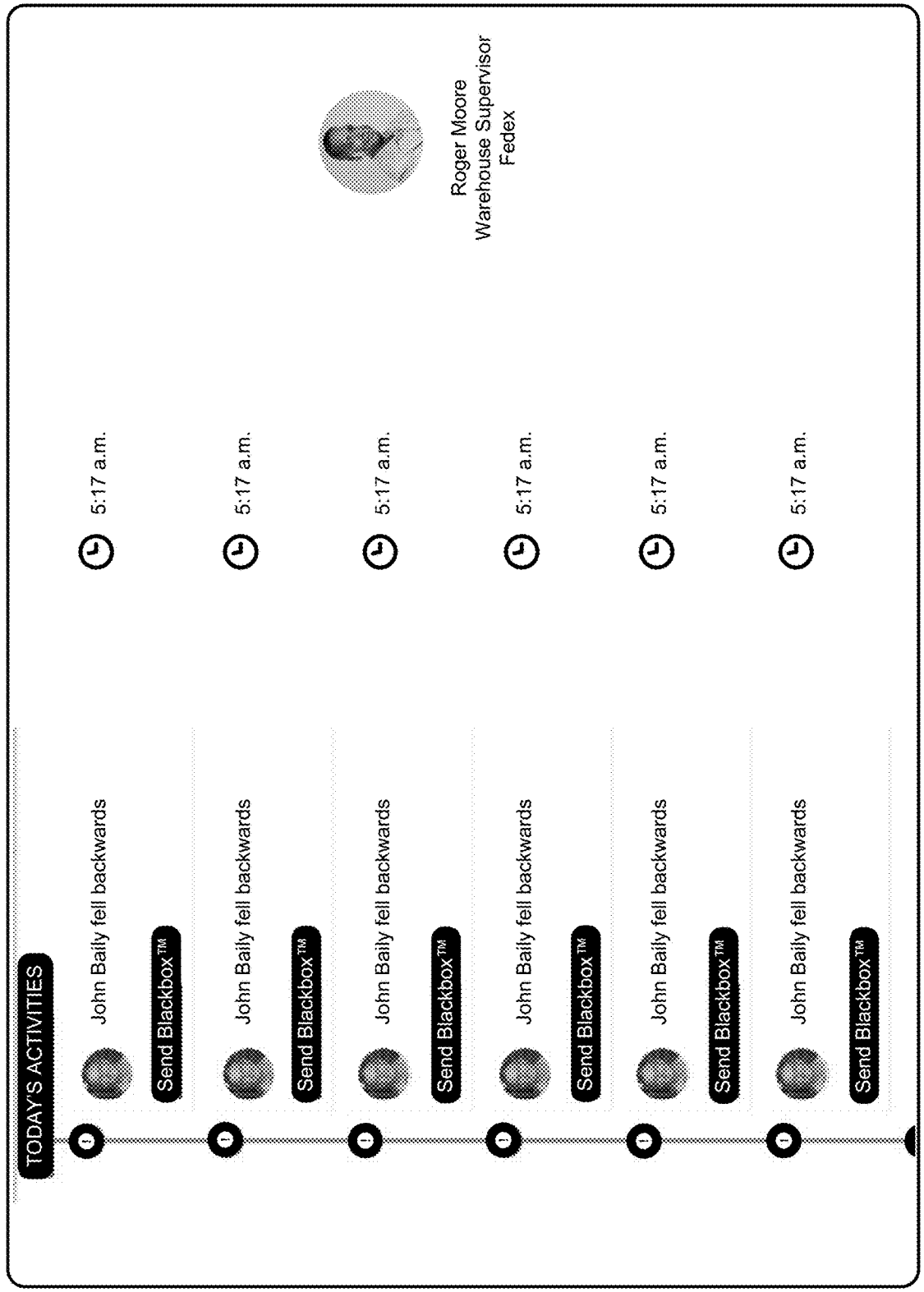
FIG. 29 illustrates an example of a feed tab on a supervisor dashboard in accordance with an embodiment.

FIG. 29 illustrates an example of a feed tab on a supervisor dashboard in accordance with an embodiment. On the supervisor dashboard, in the FEED tab, the supervisor gets real-time feed of events relating to the safety of his employees that occurred (e.g., John Bailey fell backwards). It also gives the time at which this event occurred. The supervisor can also select any date to see what safety-related events occurred with his employees.

Figure 30:
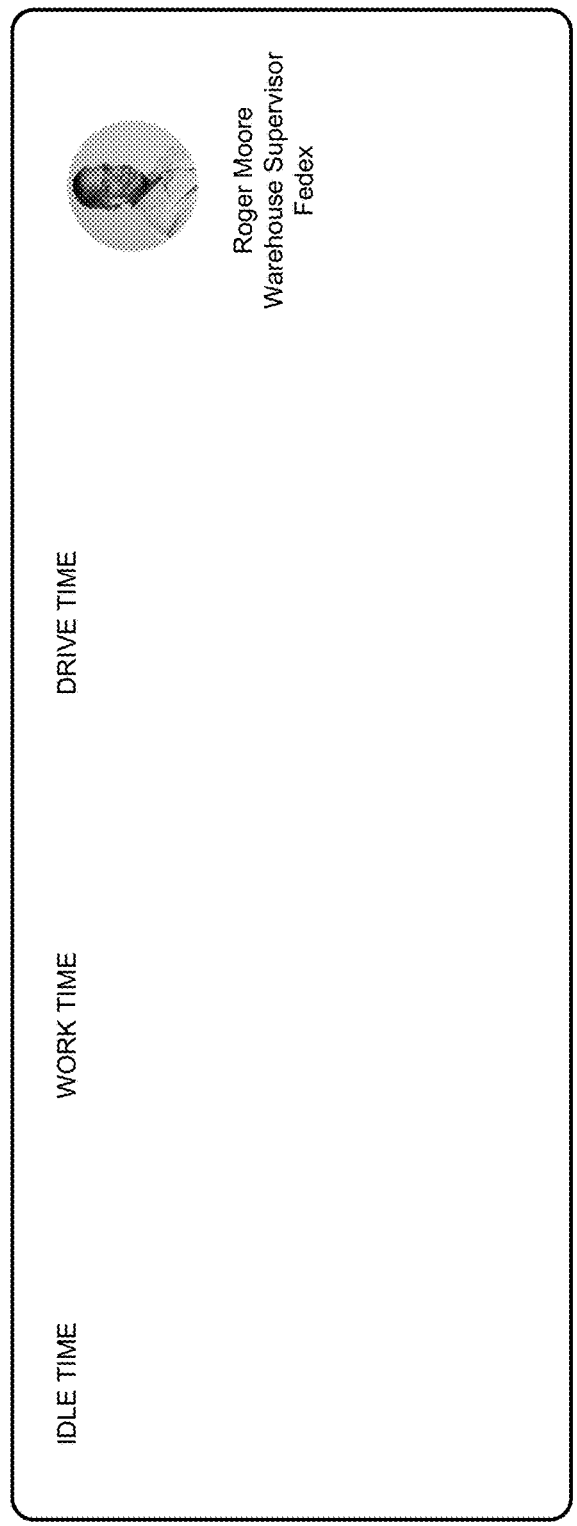
FIG. 30 illustrates an example of an employee ranking tab on a supervisor dashboard in accordance with an embodiment.

FIG. 30 illustrates an example of an employee ranking tab on a supervisor dashboard in accordance with an embodiment. On the supervisor dashboard, in the productivity tab, there are two options: employee rankings and metrics. The employee ranking tab ranks employees based on idle time, work time, and drive time. The supervisor can select one or more of the three parameters to rank his employees. In some implementations, for example, this tab may be used to provide an improved overview of how each employee is working in a warehouse.

Figure 31:
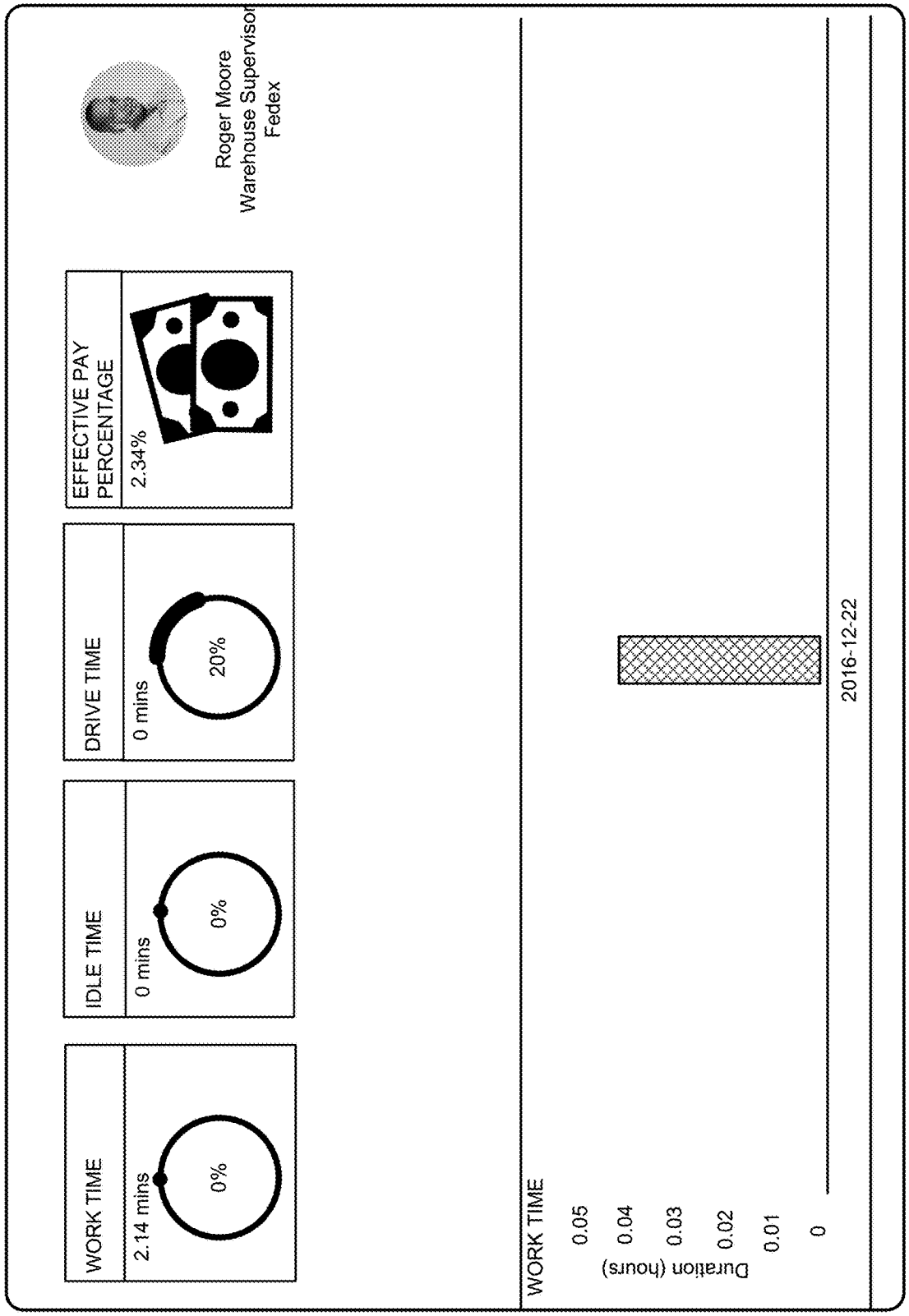
FIG. 31 illustrates an example of a metrics tab on a supervisor dashboard in accordance with an embodiment.

FIG. 31 illustrates an example of a metrics tab on a supervisor dashboard in accordance with an embodiment. In the metrics tab, the supervisor can select an employee and view the employee's metrics. In one example, the metrics which show up are the total work time, total idle time, total drive time, and effective pay percentage. It also has a bar graph which shows the employee's total work time per day. It also has an option on the top left to select daily, weekly, or monthly updates.

Figure 32:
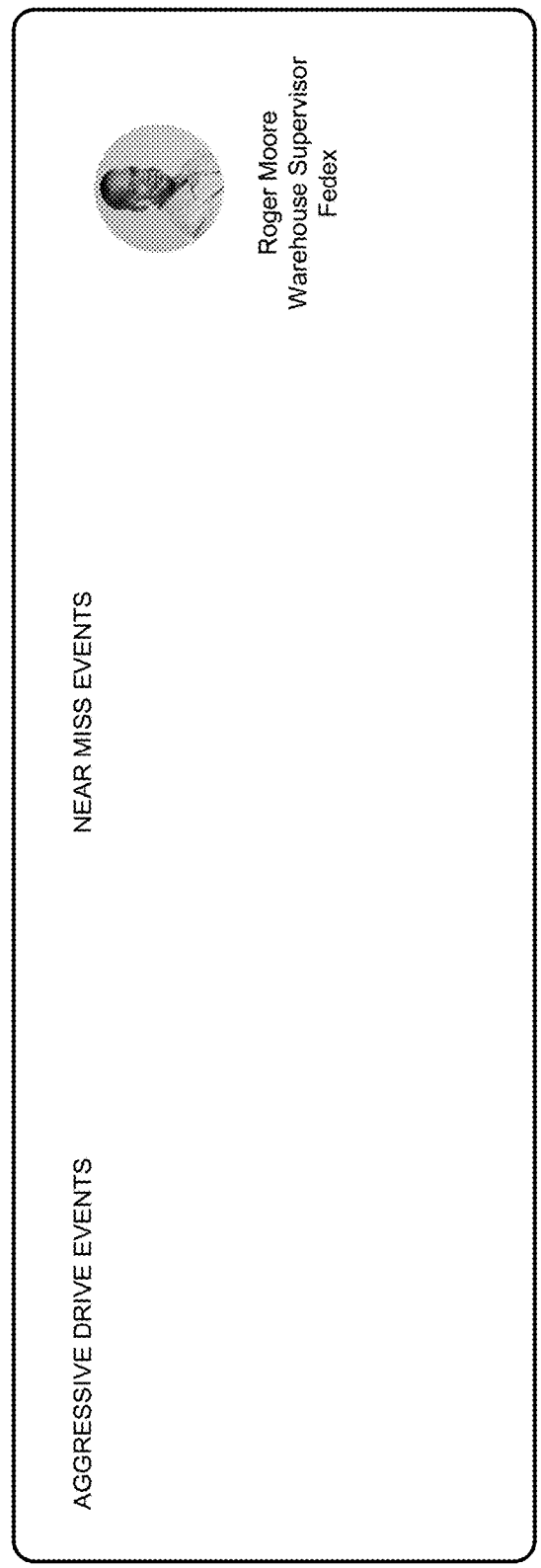
FIG. 32 illustrates an example of a safety tab on a supervisor dashboard in accordance with an embodiment.

FIG. 32 illustrates an example of a safety tab on a supervisor dashboard in accordance with an embodiment. On the supervisor dashboard, in the safety tab, there are two options: employee rankings and metrics. The employee ranking tab ranks employees based on aggressive drive events and near-miss events. The supervisor can select either of the two parameters to rank his employees. This can give a clear picture of how safe each employee is on the job.

Figure 33:
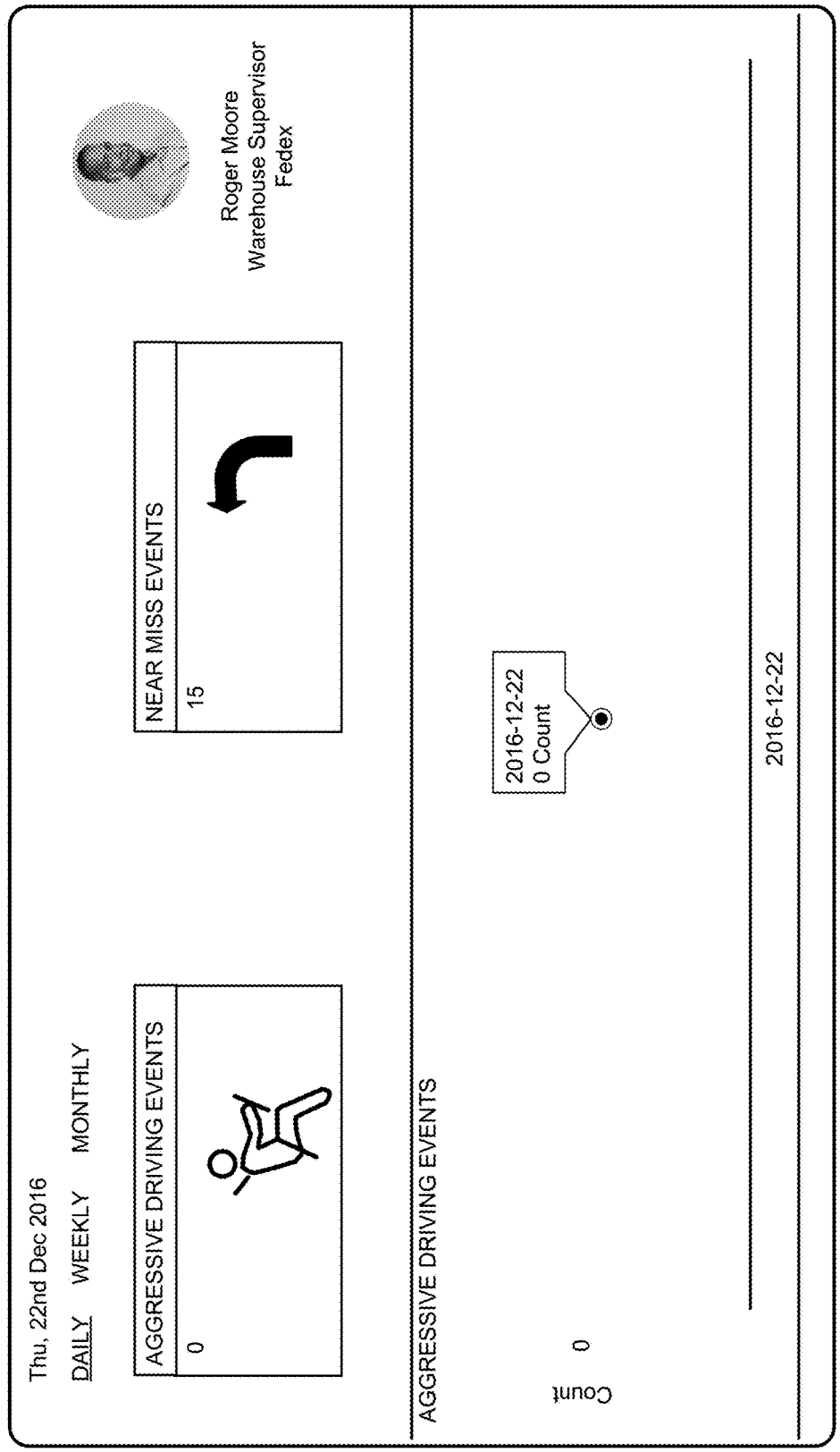
FIG. 33 illustrates an example of a safety metrics tab on a supervisor dashboard in accordance with an embodiment.

FIG. 33 illustrates an example of a safety metrics tab on a supervisor dashboard in accordance with an embodiment. In the metrics tab, the supervisor can select an employee and view associated metrics. The metrics show the aggressive driving events and near-miss events. It also has a graphical representation which shows the count for that employee's aggressive driving events. On the top left it has an option to select daily, weekly, or monthly updates.

FIG. 34 illustrates an example of an administration tab on a supervisor dashboard in accordance with an embodiment. The administration tab on the supervisor dashboard shows the data of all employees supervised by the supervisor. In various embodiments, the data has field options for Name, Designation, Role, Supervisor Name, Shift Start Time, Shift End Time, and the option to update the Shift Time. The data can be sorted based on any of these fields by clicking on them.

Figure 35:
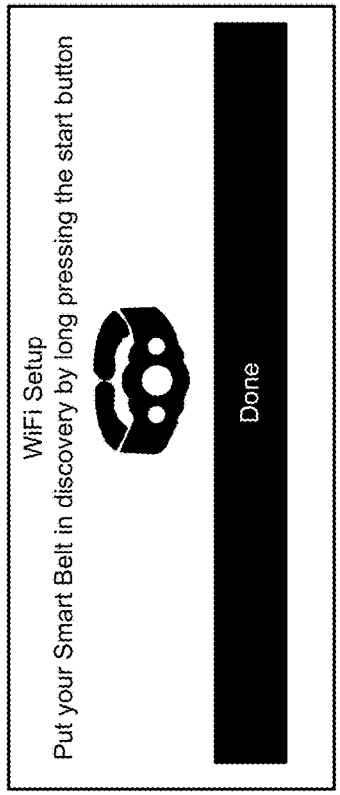
FIG. 35 illustrates an example of a WiFi setup tab on a supervisor dashboard in accordance with an embodiment.

FIG. 35 illustrates an example of a WiFi setup tab on a supervisor dashboard in accordance with an embodiment. The supervisor can set up the WiFi for the belts of his employees. It can also be set by putting the belt in discovery mode by pressing and holding the start button, then entering the Network SSID, password, and selecting the security algorithms.

Figure 36:
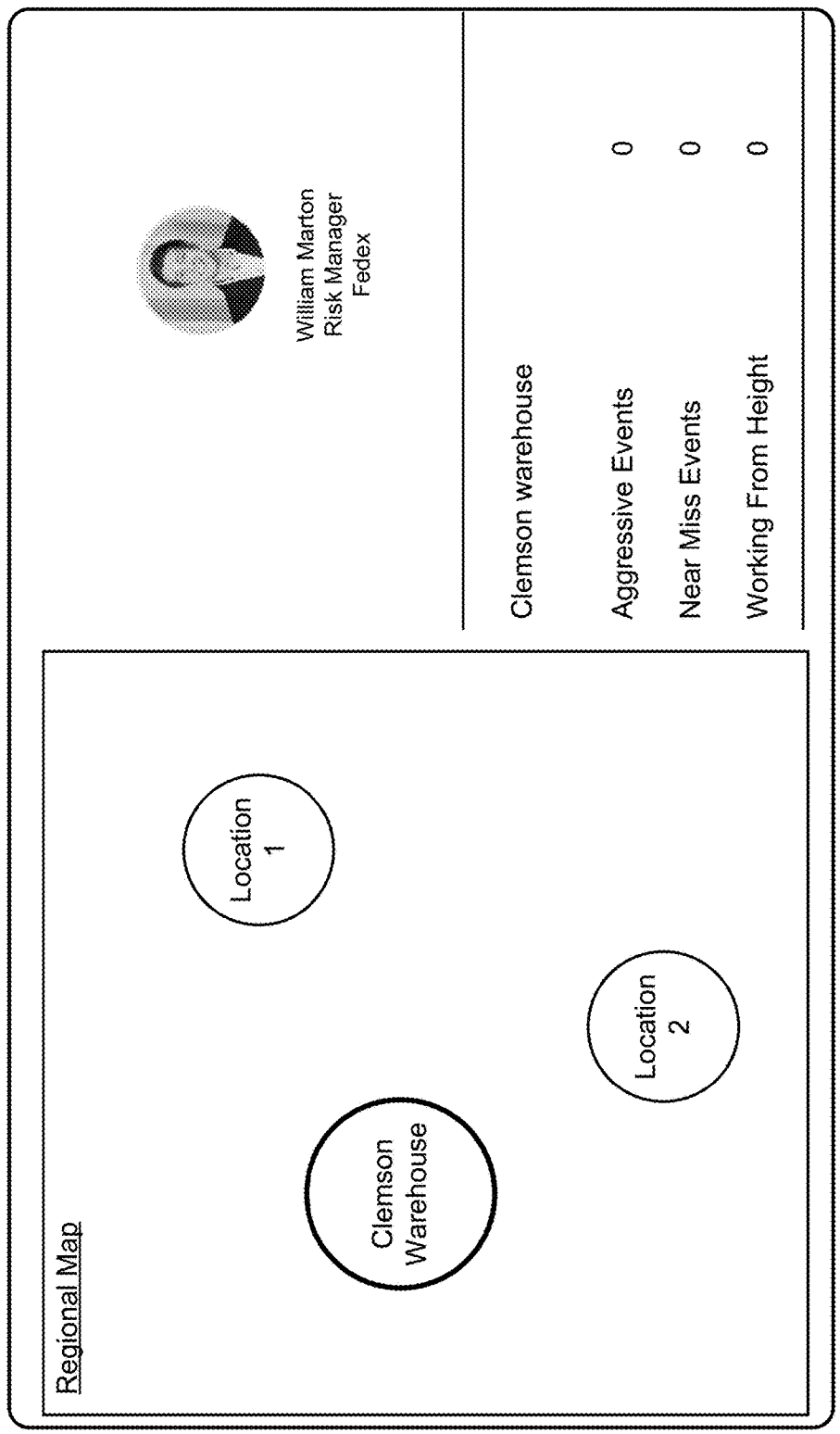
FIG. 36 illustrates an example of a risk manager dashboard in accordance with an embodiment.

FIG. 36 illustrates an example of a risk manager dashboard in accordance with an embodiment. The dashboard for the Risk Manager shows a map and locations of different warehouses the risk manager supervises. It also shows the count summary of "risky events" (aggressive events, near-miss events, and working from heights) for the selected warehouse, and the risk manager can select a particular warehouse for viewing from the drop-down list.

Figure 37:
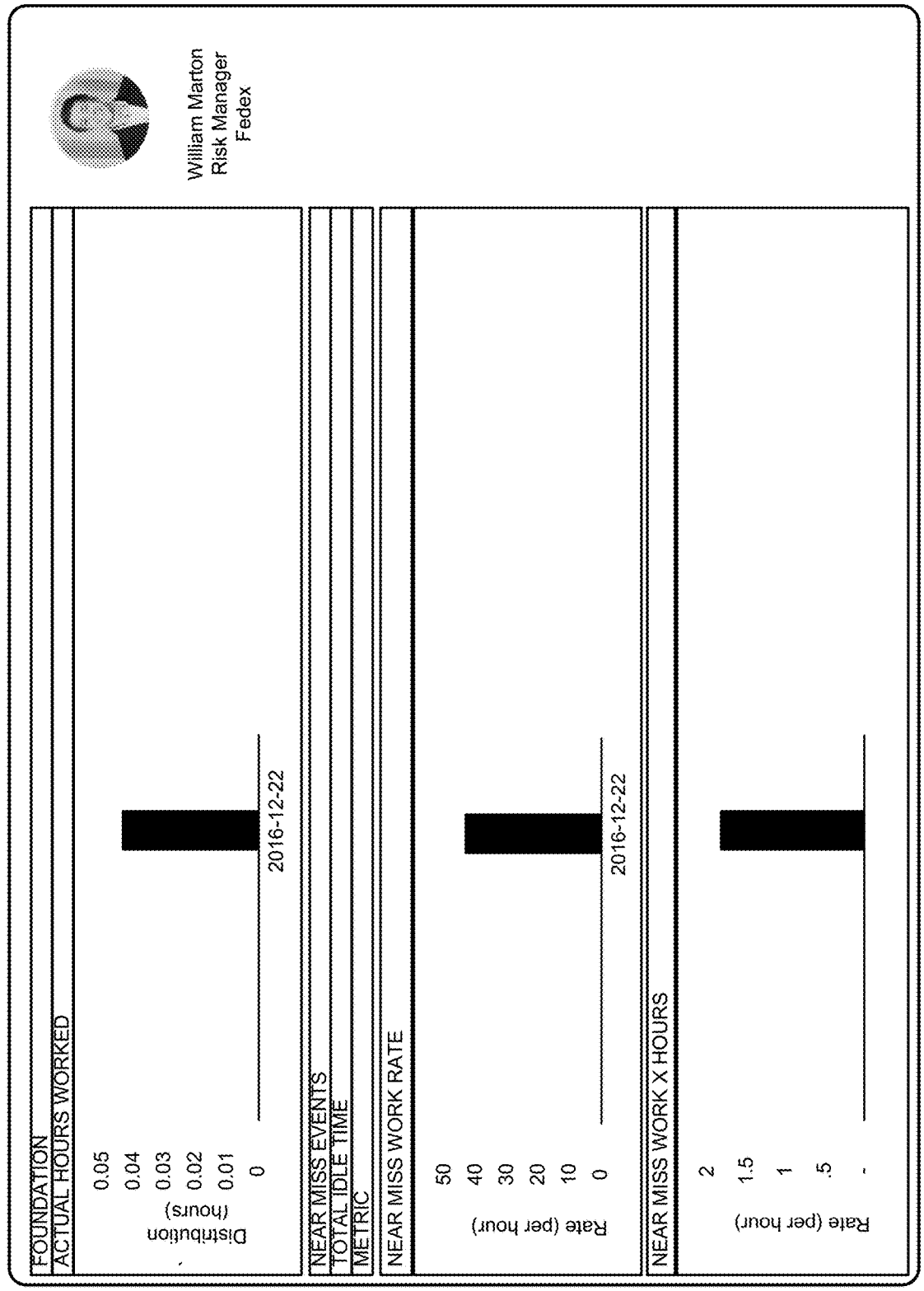
FIG. 37 illustrates an example of a work tab of a risk manager dashboard in accordance with an embodiment.

FIG. 37 illustrates an example of a work tab of a risk manager dashboard in accordance with an embodiment. The work tab under Risk Manager shows the summary of foundation, metrics, count, and height for the workplace (to be selected from the drop-down list). The work manager can see the daily, weekly, or monthly summary of these events for the selected workplace. Foundation contains the summary of actual hours worked, near-miss events and total idle time. Metric shows near-miss work rate and near-miss work hours. Slip contains the counts for slips, trips, falling forward, falling backwards, and falling sideways. These activities are identified by a predictive algorithm which gets the raw data from the sensors on the belt and updates the dashboard accordingly.

Figure 38:
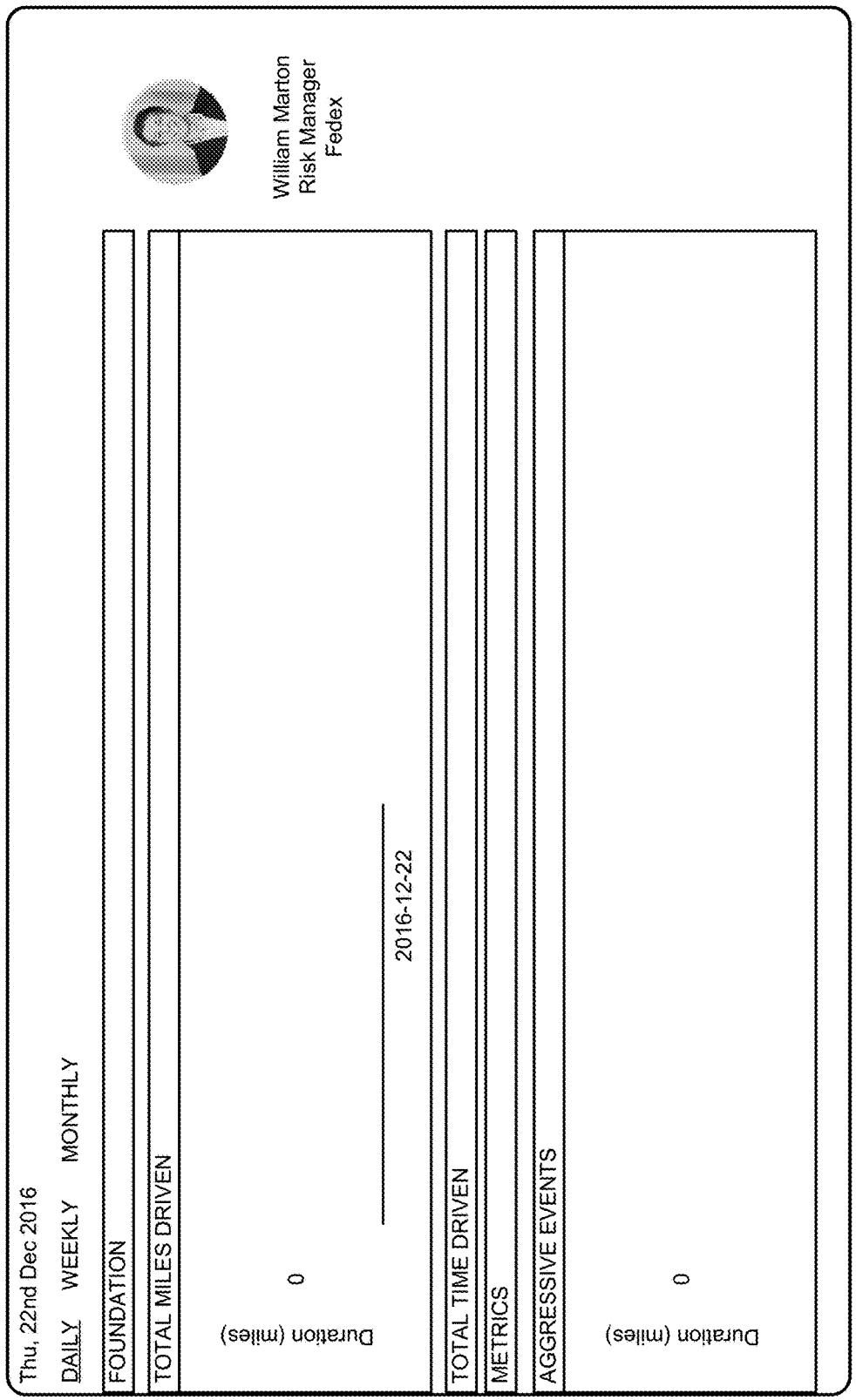
FIG. 38 illustrates an example of a drive tab of a risk manager dashboard in accordance with an embodiment.

FIG. 38 illustrates an example of a drive tab of a risk manager dashboard in accordance with an embodiment. The drive tab of the risk manager dashboard shows the summary of foundation, metrics, and counts for the driving activities for the selected warehouse. The risk manager can see the daily, weekly, or monthly summary of these events. Foundation contains the summary of total miles driven and total time driven. The metrics tab shows aggressive events, hard acceleration, hard brakes, hard corners, and swerves. These driving activities are identified by our predictive algorithm which gets the raw data from the sensors on the belt and updates the dashboard accordingly.

Figure 39:
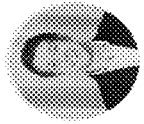
FIG. 39 illustrates an example of a blackbox tab of a risk manager dashboard in accordance with an embodiment.

FIG. 39 illustrates an example of a blackbox tab of a risk manager dashboard in accordance with an embodiment. The blackbox tab shows the data submitted for claims. Data has fields for beneficiary, submitted by, description, status, date, message, and location of the claim. The data can be sorted based on any of these fields by clicking on them.

Figure 40:
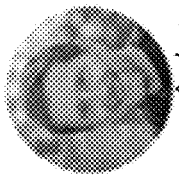
FIG. 40 illustrates an example of a chief information officer ("CIO") dashboard in accordance with an embodiment.

FIG. 40 illustrates an example of a chief information officer ("CIO") dashboard in accordance with an embodiment. Using the CIO dashboard, the CIO can add an employee to the organization individually by entering the personal details such as email, name, employee ID, designation and location name. Alternatively, employees can be added in bulk by uploading a file containing the above personal information in csv (comma separated format).

Figure 41:
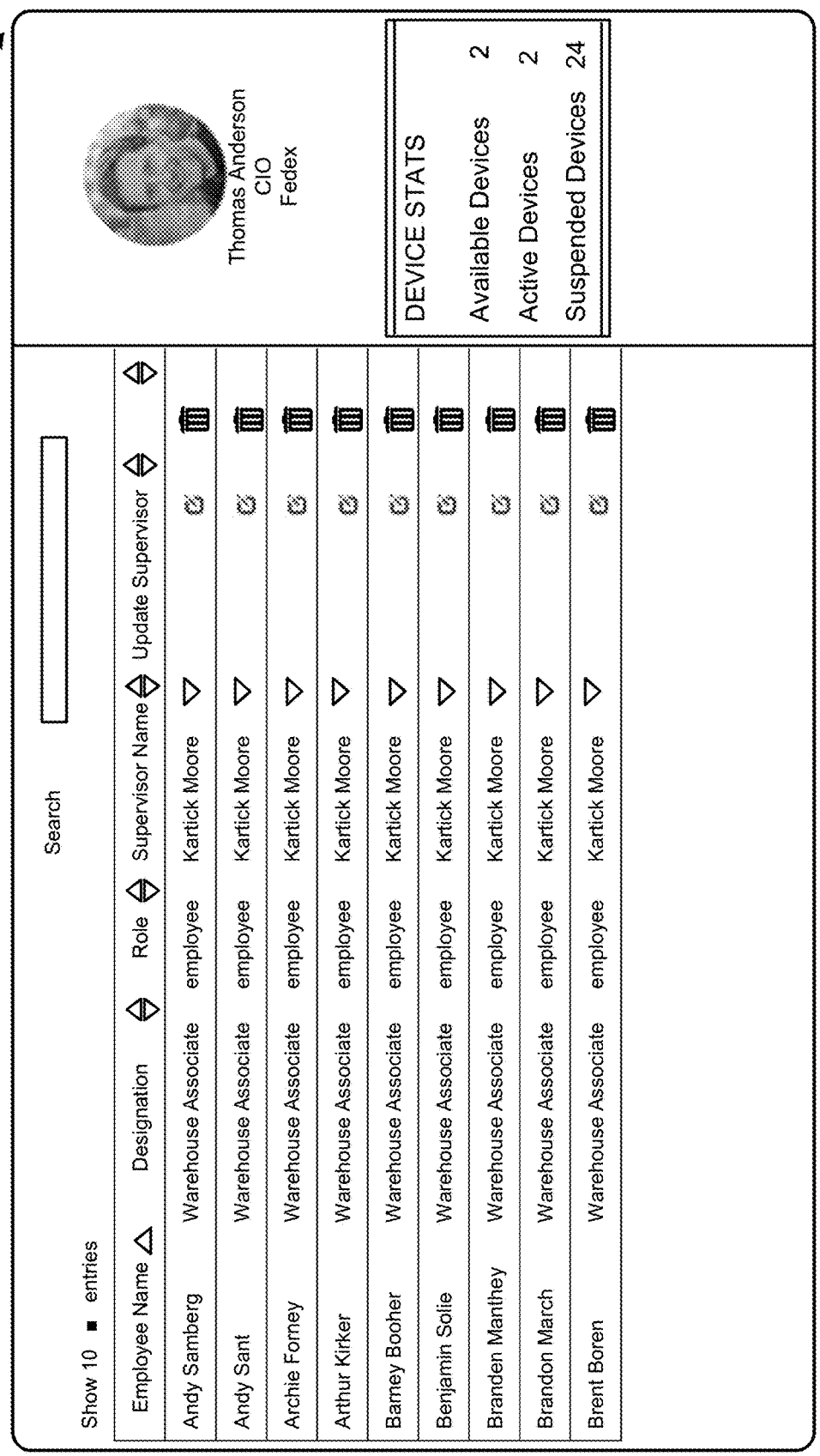
FIG. 41 illustrates an example of an employee list tab of a CIO dashboard in accordance with an embodiment.

FIG. 41 illustrates an example of an employee list tab of a CIO dashboard in accordance with an embodiment. The CIO can also view employees and their details by selecting "view employee list" under the employees tab. The CIO can also change the supervisor of the employees by selecting one of the supervisors populated in the drop-down list.

Figure 42:
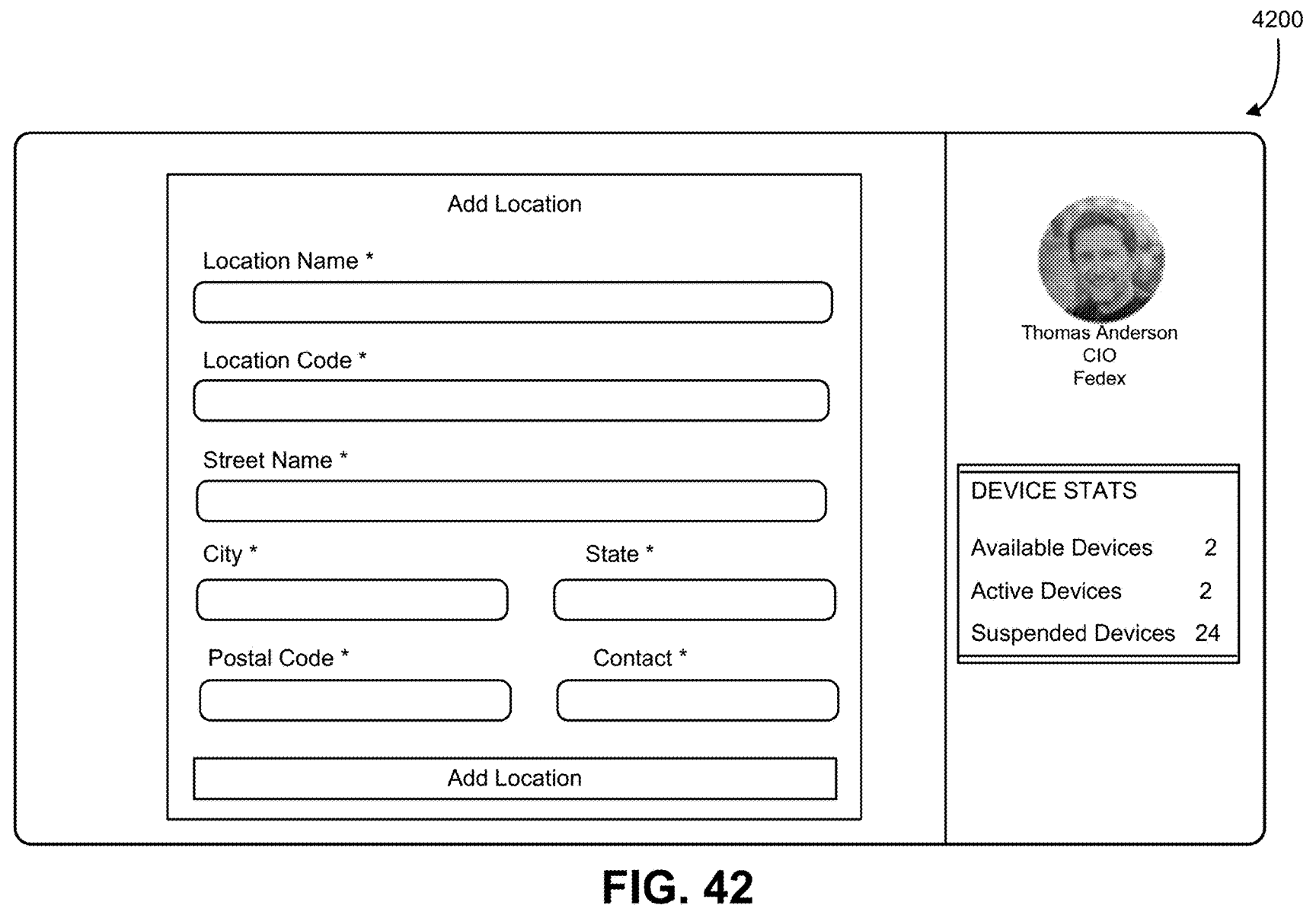

FIG. 42 illustrates an example of an organization tab of a CIO dashboard in accordance with an embodiment. The CIO has the option to add a new location to the organization by entering location name, code and address by clicking on the locations tab and selecting "add location."

FIG. 43 illustrates an example of a work location tab of a CIO dashboard in accordance with an embodiment. The CIO has the option to view the locations under the organization by clicking and customizing the view by sorting the locations by name, code, address, or contact number. He can delete any location by clicking the delete icon.

FIG. 44 illustrates an example of a metrics configuration tab of a CIO dashboard in accordance with an embodiment. The CIO has administrative privileges to configure the metrics for the company displayed on its dashboard. For example, for selecting the idle time, he has the option to select among the activities (sitting, standing, stuck on traffic, laying, and time to exit the vehicle) to be shown under the idle time.

Figure 45:
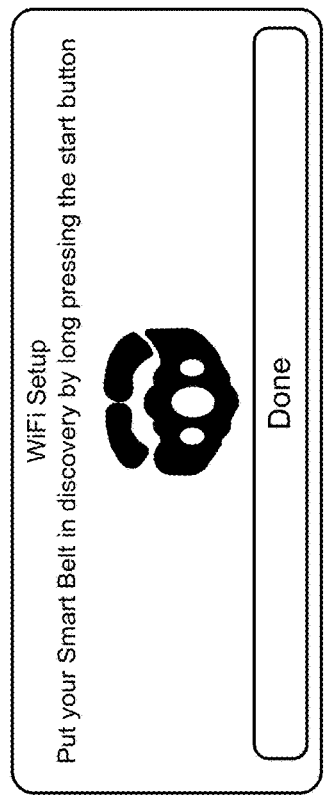
FIG. 45 illustrates an example of a WiFi configuration tab on a CIO dashboard in accordance with an embodiment.

FIG. 45 illustrates an example of a WiFi configuration tab on a CIO dashboard in accordance with an embodiment. The CIO can set up the WiFi for all the belts used in the organization by putting the belt in discovery mode and pressing and holding the start button, then entering the network SSID, password, and selecting the security algorithms.

Figure 46:
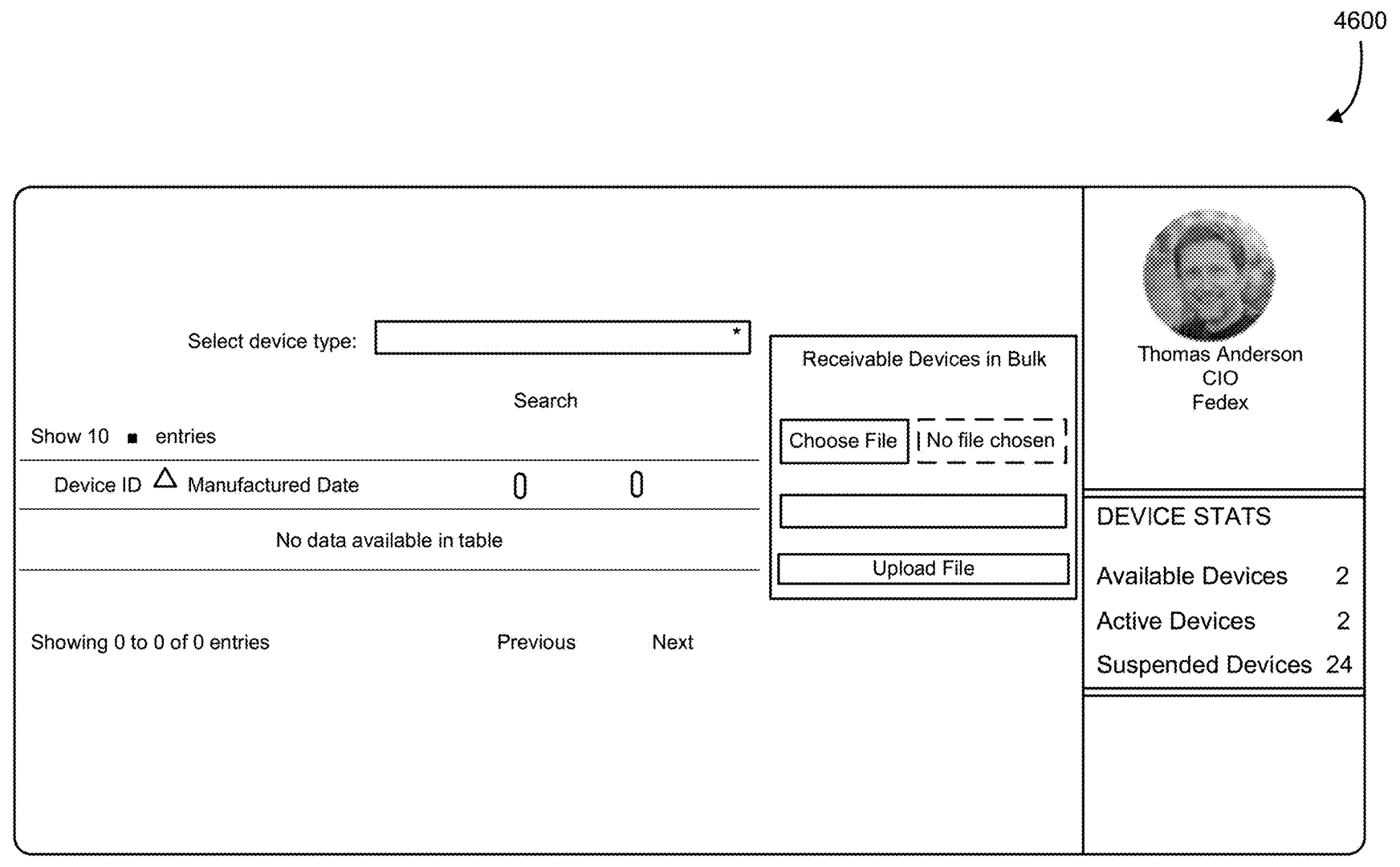

FIG. 46 illustrates an example of a device management tab of a CIO dashboard in accordance with an embodiment. The CIO has administrative privileges to receive new belt devices from a shipment, and the devices are automatically activated for the company by entering the device type and device ID. The CIO has also the option to activate belt devices in bulk by selecting a shipment file.

Figure 47:
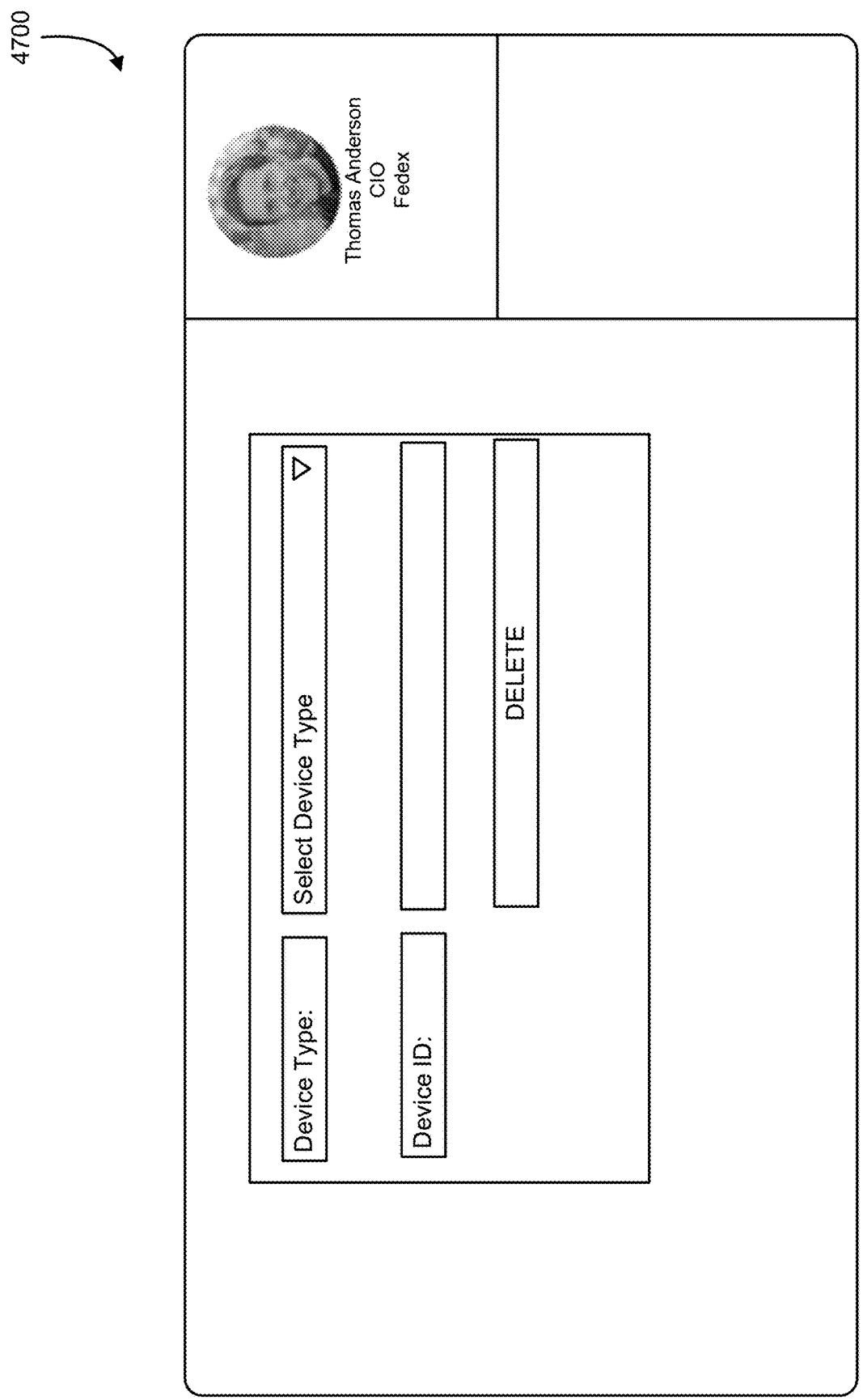
FIG. 47 illustrates an example of a delete device tab of a CIO dashboard in accordance with an embodiment. The CIO has administrative privileges to delete the devices for the organization by entering the device type and device ID.

FIG. 47 illustrates an example of a delete device tab of a CIO dashboard in accordance with an embodiment. The CIO has administrative privileges to delete the devices for the organization by entering the device type and device ID.

Various embodiments described in the present document provide advantages to managers and organizations that oversee employees who operate over distributed regions. For example, various embodiments may help improve the productivity of an employee based on idle time. Time spent on an activity related to a particular job is differentiated from time spent on other activities. Based on this, Idle Time of an employee is quantified and used to improve productivity and determine Effective Pay Rate. Idle Time may vary from company to company and depends on the job description. For example, Airline Baggage Handlers are responsible for driving carts to and from planes to load and unload cargo. Idle time for them would be defined by periods of time where they are standing still, such as waiting for planes to arrive.

In another embodiment, risk assessment models for individuals, particular job roles, locations, and other variables, link insurance to their risk-dynamic insurance pricing. Dynamic insurance policy rates for individuals and groups are based on number of accidents (trips, slips, falls etc.) in the past, combined with activity patterns, risk associated with jobs, location and other important factors. Data is collected over a period from individuals along with other information like their personal identifiable information (PII), job role, location, and other working conditions. Later this data will be used to correlate near-miss events (falls, trips, slips) to a person, job role, location, etc. In this way risk related to job roles, location, and other factors can be quantified over a period and used to determine insurance rates. For example, for driving score, the system uses a map-matching technique to find out whether a user is on a specific route and compares the user's driving with road requirements. The map-matching gives the user an optimal route for getting to their destination by calculating the impact a route has on the efficiency of completing a specific task. For example, if the user needs to drive to a specific location, the map-matching technique tells the user which route will get them there the fastest. Personalization of environmental data and models is provided by calculating personalized estimates of environmental impact and exposure. This may be inspired by the environmental impact reports and personal environmental impact reports.

In an embodiment, predictive modeling assesses the probability of accidents associated with a specific job, specific employee, time, and location. This information may be used to assign jobs for improved safety and productivity. In some examples, this information may predict the height of a free-fall motion using the aI–v and vI–v, inertial frame vertical acceleration and velocity, respectively $T_{air}$, the time the free-fall body is in the air, H the height of free-fall, and g the gravity acceleration. (aI–v=g, vI–v=gt, $T_{air}=(2H/g)^{1/2}$.

In an embodiment, behavioral modeling may be performed by monitoring the activities of people and observing physical and psychological behavioral changes of a person. For example, some medical conditions are known to slow down the walking rate of a person and may be detected by the system.

Figure 48A:
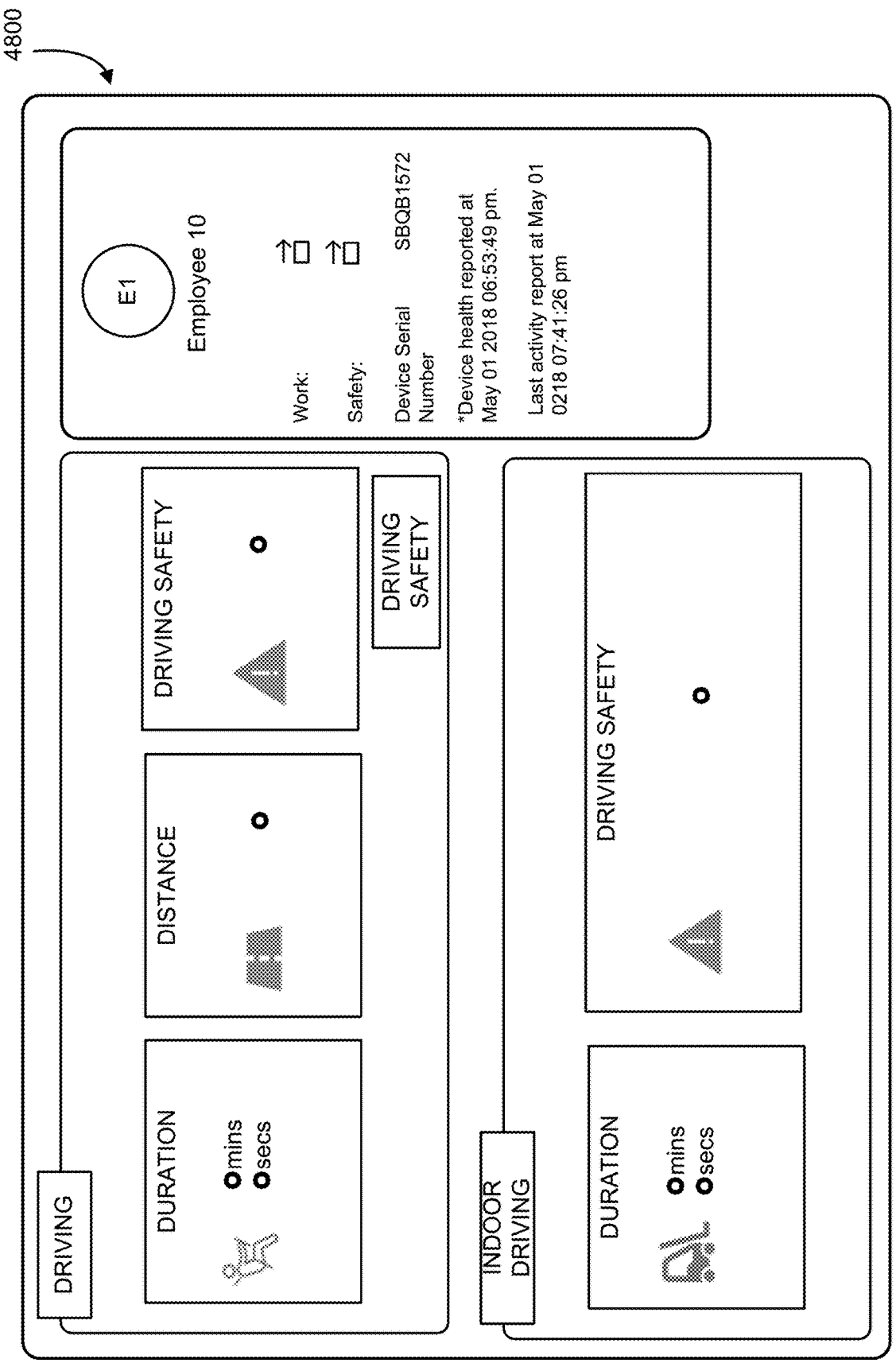
FIG. 48A illustrates an example of an indoor driving dashboard in accordance with an embodiment.
Figure 48B:
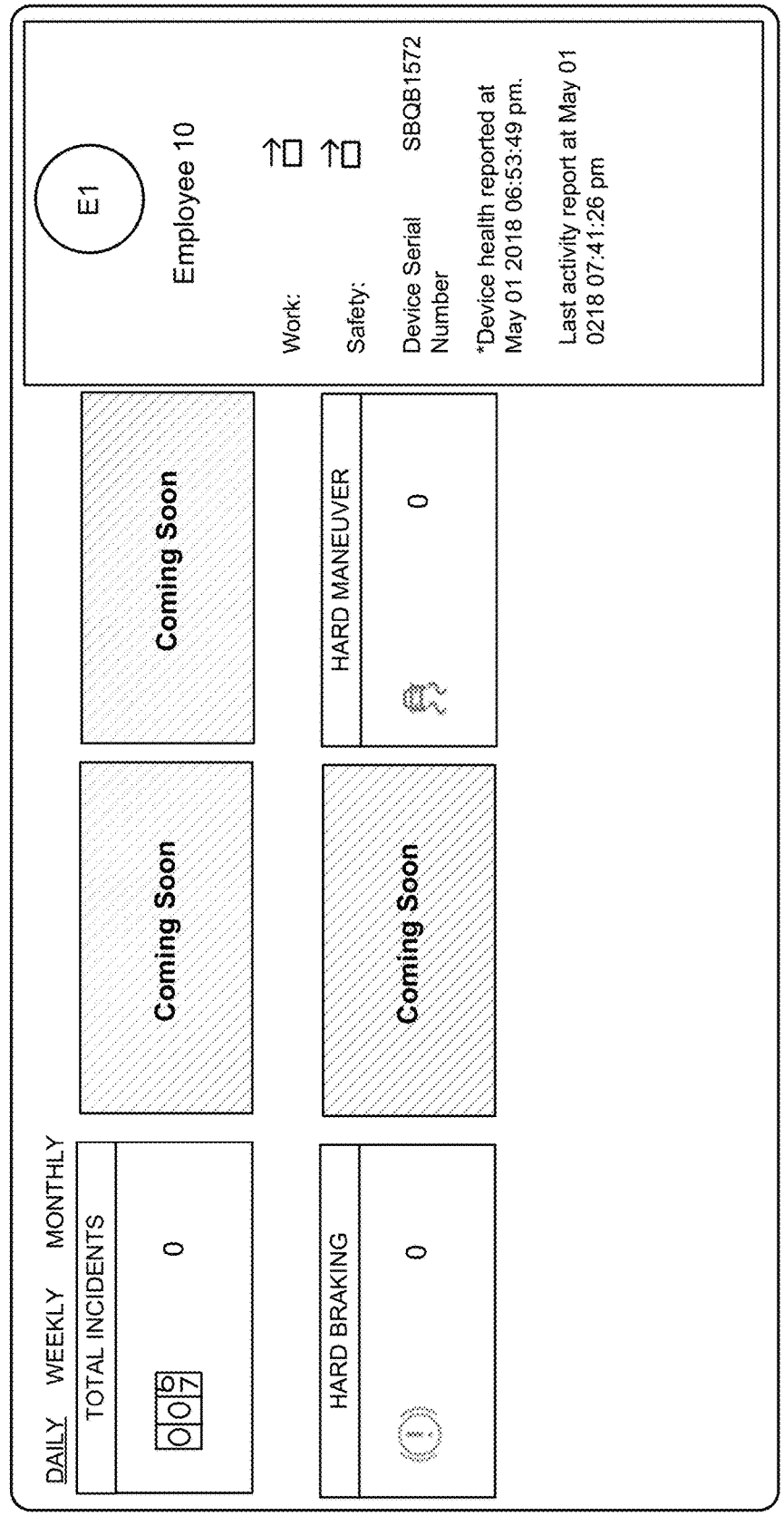
FIG. 48B illustrates an example of an extreme event dashboard for indoor driving in accordance with an embodiment.

FIGS. 48A and 48B illustrate an example of an indoor driving dashboard 4800 and 4801 in accordance with an embodiment. In an embodiment, indoor driving relates to forklifts and gives the details about the duration and safety-related incidents. Forklifts are a big reason for workplace accidents, and there are no devices in the market which can identify when a person is driving a forklift. The belt contains motion sensors which are sensitive enough to identify the vibration of an operational forklift. In an embodiment, the system calculates a quantity called 'vibration', which is the maximum of the absolute values of x, y and z components of accelerometer readings. For each second, we find the (max–min) value for vibration and call it vib_sec. Through testing, a threshold has been identified which differentiates between a person doing regular activities and driving a forklift. For windows of 30s we select sitting/standing/driving, if 75% of the time the vib_sec is above a set threshold, we mark all the sitting/standing/driving in those windows as indoor driving. The metrics associated with the forklift driving activity include duration and the count of aggressive events. Aggressive events like hard braking and hard cornering give information about the quality of forklift driving. Each axis of the motion sensor is monitored during indoor driving and when the pre-defined thresholds are crossed on the motion sensor, the events get recorded and classified into extreme events. The belt provides insights which can help in reducing the number of forklift-related accidents by a substantial amount.

In an embodiment, the whole body vibration Index is provided. There are job functions, like mining, which involve use of machines that have an impact on the human body. The human body, while operating heavy machinery, experiences vibrational forces which can have safety implications over time. The belt provides a feature called the 'whole-body vibration index' which gives the average value of vibration experienced by a worker.

When a person operates a machine causing the body to vibrate, the motion sensors and the pressures sensors are triggered. The normal values and changes of the motion and pressure sensors are used as references to derive the average whole-body vibration. The vibration values are broken down into the three axes to obtain the specific directions in which higher levels of vibration were experienced. This data is used to improve the operational methods of the machines and provide additional training wherever required.

In an embodiment, the belt provides a customizable alert system. Based on the safety concerns of each industry, there is a need to focus on some specific activities like extreme bending, twisting, or driving. The belt incorporates the provision to set the user alert functionality based on requirement. In some examples, the alert occurs in the form of a buzz. If an employee is doing an activity which is not considered safe as per the specific industry rules, the buzzer will be triggered, conveying to the employees that they need to alter the method of performing a certain activity. This alert can be set to trigger for a bend greater than 60 degrees, or a driving speed greater than 50 miles per hour, or a twisting motion with angular velocity greater than 300 degrees per second or other measurable thresholds. The supervisors in an organization can choose which factors to set as alert triggers.

In an embodiment, the techniques described herein enable detection of when a person is squatting using altimeter data to detect motion indicative of a sitting position, which is physiologically similar to a position that occurs during a squat. In many activities, squatting is the preferable method of lifting heavy weights and knowing how often a worker squats on the job can help identify the risk arising due of improper lifting techniques. A belt, such as described herein, uses the altimeter and motion sensor data to determine when a person is squatting, In an embodiment, data generated from an altimeter is analyzed by first filtering out erroneous altimeter readings by taking the time-differential of altimeter values and disregarding points with large changes (such as, for example, greater than 10 or less than –10 units). Then, a one-second average of altimeter readings is taken, in an embodiment, although other time intervals shorter or longer, regular or irregular, may be used. Any point where the one-second-averaged (or other) value increases beyond a threshold (such as, in an embodiment, 0.5 units or more) is defined as a 'trough.' For each trough, the system looks 5 prior seconds (five seconds back) or another amount of time, shorter or longer, and looks for a corresponding decrease in one-second-averaged value beyond a threshold (such as, in an embodiment, 0.4 units or less). If such a decrease is found, the system determines there was a squat. If not, the trough is disregarded and the system moves on to the next trough. In some embodiments, other data from other sensors is used to increase confidence in classifications of motion as squatting.

In an embodiment, the altimeter may be implemented using an electronic pressure sensor that produces a signal relative to atmospheric pressure. In another embodiment, the altimeter may be implemented using an ultrasonic ranger or radar altimeter that measures a distance from the sensor on the belt to the surface of the ground. If a radar altimeter or other ground sensing device is used, squatting may be identified by determining that the belt has descended to within a threshold range for an amount of time. The threshold range may be established based on the height and build of the wearer. A calibration process may be performed to establish the height of the belt above the ground when the wearer is standing, sitting, squatting, and prone. In an embodiment, a squat is indicated when the height of the belt is above the height established for the wearer being prone, and below the height established when sitting.

In yet another embodiment, an ultrasonic transponder is worn by the wearer on the wearer's foot. A sensor on the belt communicates with the transponder to identify the distance between the sensor on the belt and the transponder on the wearer's foot. The distance may be used, in some examples, to determine when the wearer is squatting, sitting, or kneeling.

Figure 49:
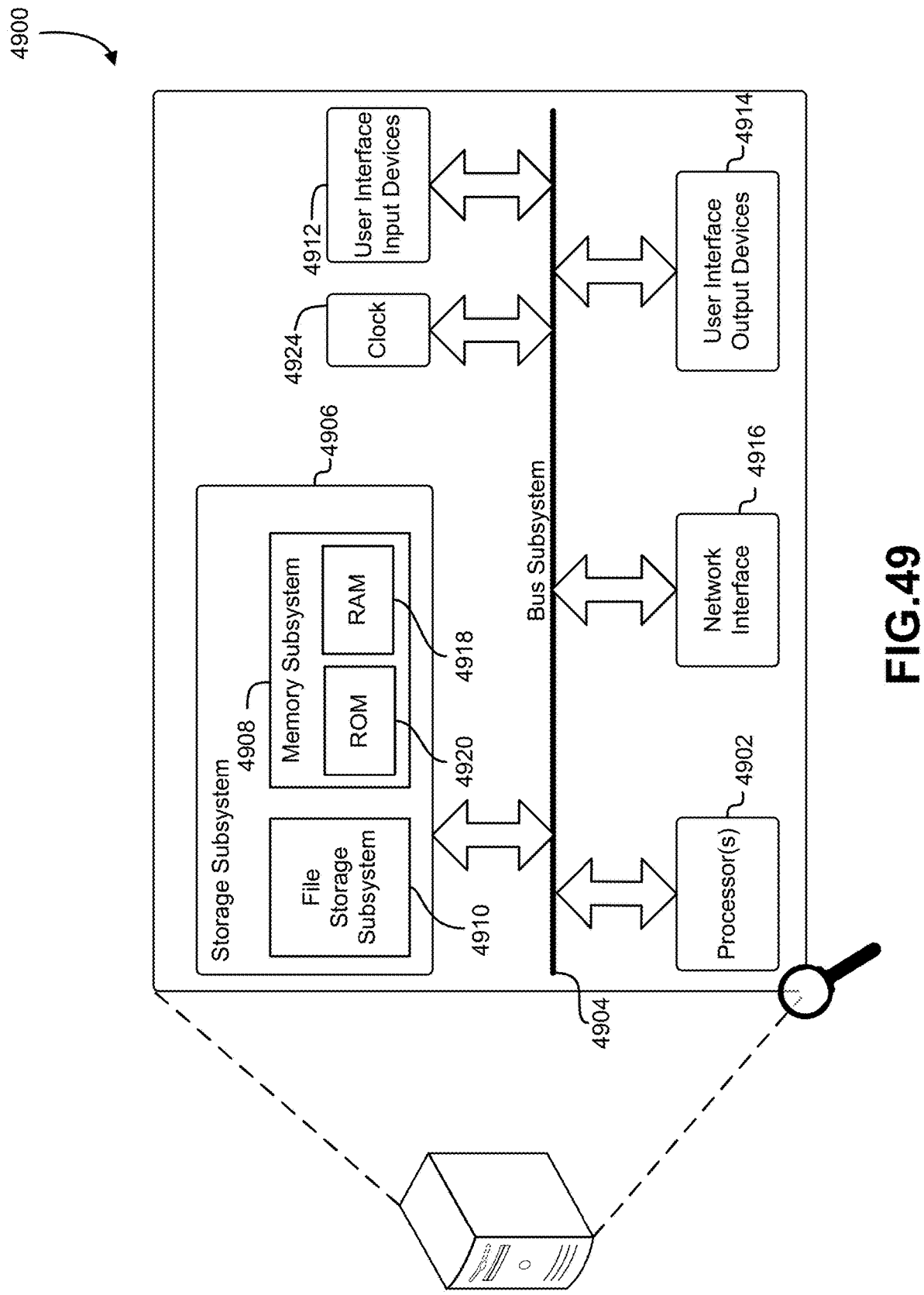
FIG. 49 illustrates an environment in which various embodiments can be implemented.

FIG. 49 illustrates an environment in which various embodiments can be implemented. FIG. 49 is an illustrative, simplified block diagram of an example computing device 4900 that may be used to practice at least one embodiment of the present disclosure. In various embodiments, the computing device 4900 may be used to implement any of the systems illustrated herein and described above. For example, the computing device 4900 may be configured for use as a data server, a web server, a portable computing device, a personal computer, or any electronic computing device. As shown in FIG. 49, the computing device 4900 may include one or more processors 4902 that may be configured to communicate with, and are operatively coupled to, a number of peripheral subsystems via a bus subsystem 4904. The processors 4902 may be utilized for the traversal of decision trees in random forest of supervised models in embodiments of the present disclosure (e.g., cause the evaluation of inverse document frequencies of various search terms, etc.). These peripheral subsystems may include a storage subsystem 4906, comprising a memory subsystem 4908 and a file storage subsystem 4910, one or more user interface input devices 4912, one or more user interface output devices 4914, and a network interface subsystem 4916. Such storage subsystem 4906 may be used for temporary or long-term storage of information such as details associated with transactions described in the present disclosure, databases of historical records described in the present disclosure, and storage of decision rules of the supervised models in the present disclosure).

The bus subsystem 4904 may provide a mechanism for enabling the various components and subsystems of computing device 4900 to communicate with each other as intended. Although the bus subsystem 4904 is shown schematically as a single bus, alternative embodiments of the bus subsystem utilize multiple busses. The network interface subsystem 4916 may provide an interface to other computing devices and networks. The network interface subsystem 4916 may serve as an interface for receiving data from, and transmitting data to, other systems from the computing device 4900. For example, the network interface subsystem 4916 may enable a data technician to connect the device to a wireless network such that the data technician may be able to transmit and receive data while in a remote location, such as a user data center. The bus subsystem 4904 may be utilized for communicating data, such as details, search terms, and so on to the supervised model of the present disclosure, and may be utilized for communicating the output of the supervised model to the one or more processors 4902 and to merchants and/or creditors via the network interface subsystem 4916.

The user interface input devices 4912 may include one or more user input devices, such as a keyboard, pointing devices such as an integrated mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to the computing device 4900. The one or more user interface output devices 4914 may include a display subsystem, a printer, or non-visual displays such as audio output devices, etc. The display subsystem may be a cathode ray tube (CRT), a flat-panel device such as a liquid crystal display (LCD), light emitting diode (LED) display, or a projection or other display device. In general, use of the term "output device" is intended to include all possible types of devices and mechanisms for outputting information from the computing device 4900. The one or more output devices 4914 may be used, for example, to present user interfaces to facilitate user interaction with applications performing processes described herein and variations therein, where such interaction may be appropriate.

The storage subsystem 4906 may provide a computer-readable storage medium for storing the basic programming and data constructs that may provide the functionality of at least one embodiment of the present disclosure. The applications (programs, code modules, instructions) that, as a result of being executed by one or more processors, may provide the functionality of one or more embodiments of the present disclosure, and may be stored in the storage subsystem 4906. These application modules or instructions may be executed by the one or more processors 4902. The storage subsystem 4906 may additionally provide a repository for storing data used in accordance with the present disclosure. The storage subsystem 4906 may comprise a memory subsystem 4908 and a file/disk storage subsystem 4910.

The memory subsystem 4908 may include a number of memories, including a main random access memory (RAM) 4918 for storage of instructions and data during program execution and a read only memory (ROM) 4920 in which fixed instructions may be stored. The file storage subsystem 4910 may provide a non-transitory persistent (non-volatile) storage for program and data files, and may include a hard disk drive, a floppy disk drive along with associated removable media, a Compact Disk Read Only Memory (CD-ROM) drive, an optical drive, removable media cartridges, and other like storage media.

The computing device 4900 may include at least one local clock 4924. The local clock 4924 may be a counter that represents the number of ticks that have transpired from a particular starting date and may be located integrally within the computing device 4900. The local clock 4924 may be used to synchronize data transfers in the processors for the computing device 4900 and all of the subsystems included therein at specific clock pulses and may be used to coordinate synchronous operations between the computing device 4900 and other systems in a data center. In one embodiment, the local clock 4924 is an atomic clock. In another embodiment, the local clock is a programmable interval timer.

The computing device 4900 may be of various types, including a portable computer device, tablet computer, a workstation, or any other device described below. Additionally, the computing device 4900 may include another device that may be connected to the computing device 4900 through one or more ports (e.g., USB, a headphone jack, Lightning connector, etc.). The device that may be connected to the computing device 4900 may include a plurality of ports configured to accept fiber-optic connectors. Accordingly, this device may be configured to convert optical signals to electrical signals that may be transmitted through the port connecting the device to the computing device 4900 for processing. Due to the ever-changing nature of computers and networks, the description of the computing device 4900 depicted in FIG. 49 is intended only as a specific example for purposes of illustrating the preferred embodiment of the device. Many other configurations having more or fewer components from the system depicted in FIG. 49 are possible.

Figure 50:
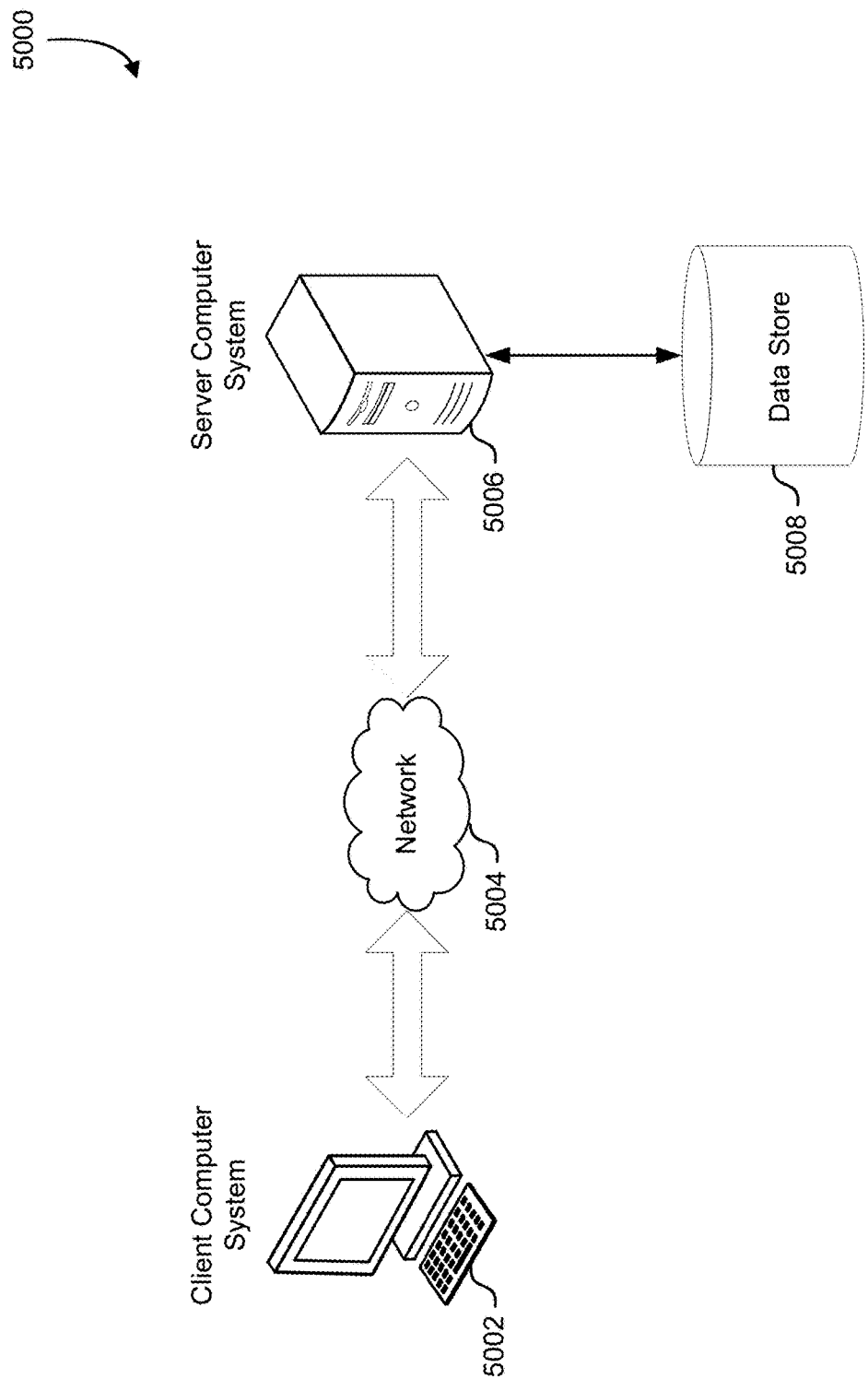
FIG. 50 illustrates aspects of an example environment for implementing aspects in accordance with various embodiments.

FIG. 50 illustrates aspects of an example environment 5000 for implementing aspects in accordance with various embodiments. A client/server environment is shown for the purposes of explanation, but other environments may be used in other implementations. The environment includes a client computer system 5002. The client computer system can be a desktop computer, laptop computer, computing appliance, or mobile device that is able to send or receive information over a computer network 5004. Other examples of client computer systems include cell phones, tablet computers, wearable devices, personal digital assistants ("PDA's"), embedded control systems, and smart appliances. The computer network 5004 can be a wired or wireless network. Wired networks can include wired networks such as Ethernet (10baseT, 100baseT, or Gigabit), AppleTalk, Token Ring, Fiber Channel, USB, RS-232, or Powerline networks, or wireless networks such as 802.11 Wi-Fi, Bluetooth, or infrared-communication-based networks. A variety of communication protocols may be used over the computer network 5004. The communication protocols may include TCP/IP, IPX, or DLC. A variety of intermediate protocols may operate on top of these protocols such as HTTP, HTTP secure ("HTTPS"), simple network management protocol ("SNMP"), and simple mail transfer protocol ("SMTP"). The computer network 5004 may include a combination of subnetworks including the Internet, internal home networks, or business intranets.

The environment includes a server computer system 5006. The server computer system 5006 receives requests from various computer systems connected to the computer network 5004 including the client computer system 5002. The server computer system 5006 can be a server computer system, a number of server computer systems arranged in a server cluster, or virtual computer system capable of receiving requests and sending responses over the computer network 5004. In some environments, a personal computer system, handheld device, or cell phone can perform the functions of the server computer system 5006. If more than one addressable device is used to process requests, a load balancer or other coordinating entity such as a firewall may be placed between the client computer system 5002 and a server computer system 5006. The load balancer may receive requests on behalf of a collection of server devices, and route requests across the collection of server devices.

The server computer system 5006 may implement a plurality of services by exporting more than one service interface. For example, a number of services may be implemented on the server computer system 5006 as a corresponding number of processes. Each process may be bound to different network address and/or network port. A particular network client can access a particular service by submitting a request to the corresponding network address and port.

The server computer system 5006 is connected to a data store 5008. The term data store may refer to a device capable of storing and retrieving computer readable information such as disk drives, semiconductor RAM, ROM, flash memory, optical disk, CD-ROM, EEPROM. In some implementations, right-once/read-many memory such as EEPROM memory may be used to generate a data store. In some implementations, a database may be used to store information. In some examples, a database may be created through the use of a commercial application such as SQL Server, Oracle, Access, or other relational database engine. Tables and keys are defined that allow for rapid and efficient access to information using particular key values. Tables may be linked for quick and efficient access to data. Relational database engines allow operations to be performed on stored data using a standard query language ("SQL"). SQL commands or scripts may be submitted that create, alter, delete, or synthesize information stored within the database. Those skilled in the art will appreciate that, in some systems, some database functions may be integrated into an application. Hash tables, ordered lists, stacks and queues may be implemented and arranged to perform similar functionality in many applications. The term "data store" refers to any device or combination of devices capable of storing, accessing and retrieving data, which may include any combination and number of data servers, databases, data storage devices and data storage media, in any standard, distributed, virtual or clustered environment. As used herein, the term "database" refers to both commercial database engines and custom implementations of database functionality using ordered and indexed data structures, hash tables, arrays, linked lists, key-value pair structures, and the like.

A server computer system 5006 may provide access and authentication controls that limit access to the information maintained in the data store 5008. An authentication system controls access to the server computer system by verifying the identity of the person or entity submitting a request to the server computer system 5006. Authentication is achieved by validating authentication information such as a username and password, a digital signature, or a biometric value. In some implementations, authentication occurs through the submission of a username and password known only by an authorized user. In another implementation, authentication affairs to the submission of a digital signature using a cryptographic key known to be under the control of the client computer system 5002. The cryptographic key may be a private cryptographic key associated with a digital certificate. Requests submitted to the server computer system 5006 may be subject to authorization controls. Authorization controls may be based at least in part on the identity of the requester or the requesting device. In some implementations, authorization controls may subject service requests to a time-based or data-rate throttling limitation.

Content stored on the data store 5008 and served by the server computer system 5006 may include documents, text, graphics, music or audio, video content, executable content, executable scripts, or binary data for use with a computer application. For example, content served by Web server may be in HyperText Markup Language ("HTML"), Extensible Markup Language ("XML"), JavaScript, Cascading Style Sheets ("CSS"), JavaScript Object Notation (JSON), and/or another appropriate format. Content may be served from the server computer system 5006 to the client computer system 5002 in plaintext or encrypted form.

Data encryption may be accomplished using various forms of symmetric and/or asymmetric cryptographic primitives. Symmetric key algorithms may include various schemes for performing cryptographic operations on data including block ciphers, stream ciphers and digital signature schemes. Example symmetric key algorithms include the advanced encryption standard (AES), the data encryption standard (DES), triple DES (3DES), Serpent, Twofish, blowfish, CASTS, RC4 and the international data encryption algorithm (IDEA). Symmetric key algorithms may also include those used to generate output of one way functions and include algorithms that utilize hash-based message authentication codes (HMACs), message authentication codes (MACs) in general, PBKDF2 and Bcrypt. Asymmetric key algorithms may also include various schemes for performing cryptographic operations on data. Example algorithms include those that utilize the Diffie-Hellman key exchange protocol, the digital signature standard (DSS), the digital signature algorithm, the ElGamal algorithm, various elliptic curve algorithms, password-authenticated key agreement techniques, the pallier cryptosystem, the RSA encryption algorithm (PKCS #1), the Cramer-Shoup cryptosystem, the YAK authenticated key agreement protocol, the NTRUEncrypt cryptosystem, the McEliece cryptosystem, and others. Elliptic curve algorithms include the elliptic curve Diffie-Hellman (ECDH) key agreement scheme, the Elliptic Curve Integrated Encryption Scheme (ECIES), the Elliptic Curve Digital Signature Algorithm (ECDSA), the ECMQV key agreement scheme and the ECQV implicit certificate scheme. Other algorithms and combinations of algorithms are also considered as being within the scope of the present disclosure and the above is not intended to be an exhaustive list.

Note that the term "digital signature" includes any information usable to cryptographically verify authenticity of a message including information generated using an RSA-based digital scheme (such as RSA-PSS), the digital signature algorithm (DSA) and the elliptic curve digital signature algorithm, the ElGamal signature scheme, the Schnorr signature scheme, the Pointcheval-Stern signature algorithm, the Rabin signature algorithm, pairing-based digital signature schemes (such as the Boneh-Lynn-Schacham signature scheme), undeniable digital signature schemes, and others. Further, message authentication codes (such as hash-based message authentication codes (HMACs), keyed cryptographic hash functions, and other types of information may also be used as digital signatures.

It should be noted that the phrase "one-way function" includes functions that are not necessarily one-way in the strict mathematical sense, but that exhibit properties (such as collision resistance, preimage resistance and second preimage resistance) that render the function useful in contexts in which the various techniques of the present disclosure are applied. In this manner, an entity with output of the function but without access to the corresponding input, is unable to determine the input without, for instance, extraordinary expenditure of computational resources necessary for a cryptographic (e.g., brute force) attack. One-way functions (also referred to as "effectively one-way functions") include, but are not limited to, cryptographic hash functions such as message authentication codes, (e.g., hash based message authentication code (HMAC)), key derivation functions, such as PBKDF2 and bcrypt (with the password being based at least in part on the plaintext and the cryptographic key, e.g.) and other secure randomization functions which may, but do not necessarily, have a domain (set of possible inputs) that is larger than their range (possible outputs). Other suitable functions (referred to as "f") for various embodiments include, but are not limited to, functions that take at least a plaintext and cryptographic key as input and that have a property of preimage resistance (given a value y, the probability of randomly generating an input x such that $f(x)=y$ is below a specified threshold), second preimage resistance (given an input x1, the probably of randomly generating another input x2, different from x1, such that $f(x1)=f(x2)$ is below a specified threshold) and/or collision resistance (the probability of two different inputs resulting in the same output is less than a specified threshold). The exact threshold for each probability may be context-dependent, with lower probabilities corresponding to higher security contexts. Hash functions usable as one-way functions in accordance with the techniques of the present disclosure include, but are not limited to, functions described in the National Institute of Standards and Technology (NIST) Special Publication 800-107, Revision 1 "Recommendation for Applications Using Approved Hash Algorithms," which is incorporated herein by reference.

The short-range wireless communication channel may be established using various technologies, such as induction wireless, infrared wireless (such as technologies operating according to specifications and protocols provided by the Infrared Data Association or IrDA) or ultra-wideband formats. In some embodiments, the first and second devices may utilize short-range, low-power and high-frequency radio transmissions, such as Bluetooth®. In still other embodiments, the first and second devices may support acoustic-based data transfer. For example, the second device may include software components and a speaker that enable the second device to broadcast data to the first device as sound waves, while the first device may include software components and microphone that enable the second device to receive the data embedded in the sound waves. Thus, one or more of radio signal-based data transfer (e.g., near field communication (NFC) or Bluetooth®), light-based data transfer (e.g., infrared data transfer), an acoustic-based data transfer (e.g., sound wave-embedded data), or magnetic field-based transfer (e.g., reading data from a magnetic stripe) may be used for inter-device communication. The protocols and components for enabling computing devices to perform the systems and methods of the present disclosure using such means for inter-device communication are well known to those skilled in the art of computer communications and thus, need not be described in more detail herein. Generally, embodiments described herein are not limited to those explicitly illustrated herein.

Note also that the examples used herein may be performed in compliance with one or more of: Request for Comments (RFC) 4250, RFC 4251, RFC 4252, RFC 4253, RFC 4254, RFC 4255, RFC 4256, RFC 4335, RFC 4344, RFC 4345, RFC 4419, RFC 4432, RFC 4462, RFC 4716, RFC 4819, RFC 5647, RFC 5656, RFC 6187, RFC 6239, RFC 6594, and RFC 6668, which are incorporated by reference.

Generally, embodiments of the present disclosure may use various protocols, such as a SSL or TLS protocol and extensions thereto, as defined in Request for Comments (RFC) 2246, RFC 2595, RFC 2712, RFC 2817, RFC 2818, RFC 3207, RFC 3268, RFC 3546, RFC 3749, RFC 3943, RFC 4132, RFC 4162, RFC 4217, RFC 4279, RFC 4347, RFC 4366, RFC 4492, RFC 4680, RFC 4681, RFC 4785, RFC 5054, RFC 5077, RFC 5081, RFC 5238, RFC 5246, RFC 5288, RFC 5289, RFC 5746, RFC 5764, RFC 5878, RFC 5932, RFC 6083, RFC 6066, RFC 6091, RFC 6176, RFC 6209, RFC 6347, RFC 6367, RFC 6460, RFC 6655, RFC 7027, and RFC 7366 which are incorporated herein by reference, to establish encrypted communications sessions. Other protocols implemented below the application layer of the Open Systems Interconnect (OSI) model may also be used and/or adapted to utilize techniques described herein. It should be noted that the techniques described herein are adaptable to other protocols such as the Real Time Messaging Protocol (RTMP), the Point-to-Point Tunneling Protocol (PPTP), the Layer 2 Tunneling Protocol, various virtual private network (VPN) protocols, Internet Protocol Security (e.g., as defined in RFC 1825 through 1829, RFC 2401, RFC 2412, RFC 4301, RFC 4309, and RFC 4303) and other protocols, such as protocols for secure communication that include a handshake.

Note that a system is said to be configured to trust a public cryptographic key if logic with which the system is configured to operate is dependent on whether an attempt to verify a digital signature with the public cryptographic key is successful. Similarly, a system is said to be configured to trust a symmetric cryptographic key if logic with which the system is configured to operate is dependent on whether an attempt to verify a digital signature with the symmetric cryptographic key is successful.

The location of the system can be determined using a variety of geolocation technologies such as global positioning systems ("GPS"), Wi-Fi based positioning systems ("WPS"), LORAN, GLONASS (Globalnaya navigatsionnaya sputnikovaya sistema), Galileo global navigation satellite system, BeiDou Navigation Satellite System, Bluetooth-based positioning systems such as Zonith, or other geolocation hardware built into the system. In some implementations, terrestrial aviation-navigation signals such as Automatic Direction Finding ("ADF"), VHF Omnirange ("VOR"), are used to determine the geolocation of the system.

In various embodiments, data objects such as digital signatures may be cryptographically verifiable. In one example, cryptographically verifiable data objects are created to be cryptographically verifiable by the system to which the data object is to be provided or another system that operates in conjunction with the system to which the data object is to be provided. For example, the data object may be encrypted so as to be decryptable by the system that will cryptographically verify the data object, where the ability to decrypt the data object serves as cryptographic verification of the data object. As another example, the data object may be digitally signed (thereby producing a digital signature of the data object) such that the digital signature is verifiable by the system that will cryptographically verify the data object. In other examples, both encryption and digital signatures are used for cryptographic verifiability and/or security. The key used to encrypt and/or digitally sign the data object may vary in accordance with various embodiments and the same key is not necessarily used for both encryption and digital signing, where applicable. In some embodiments, a key used to encrypt the data object is a public key of a public/private key pair where the private key of the key pair is maintained securely by the system to which the data object is to be provided, thereby enabling the system to decrypt the data object using the private key of the key pair. Using the public key to encrypt the data object may include generating a symmetric key, using the symmetric key to encrypt the data object, and encrypting the symmetric key using the public key, where the encrypted symmetric key is provided to a system with the encrypted data object to enable the system to use the corresponding private key to decrypt the symmetric key and use the decrypted symmetric key to decrypt the data object. Further, in some embodiments, the data object is digitally signed using a private key of a public/private key pair corresponding to the computer system that encrypts and/or digitally signs the data object (e.g., a user device). For example, an application may be provisioned with the private key and the data object may include a certificate for the private key for use by a system for verification of the digital signature of the data object. Other variations, including variations where a symmetric key shared between the user computer and the system that cryptographically verifies the data object can be used to encrypt and/or digitally sign the data object.

In the preceding and following description, various techniques are described. For purposes of explanation, specific configurations and details are set forth in order to provide a thorough understanding of possible ways of implementing the techniques. However, it will also be apparent that the techniques described below may be practiced in different configurations without the specific details. Furthermore, well-known features may be omitted or simplified to avoid obscuring the techniques being described.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. In some embodiments, the code is stored on set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media may comprise multiple non-transitory computer-readable storage media and one or more of individual non-transitory storage media of the multiple non-transitory computer-readable storage media may lack all of the code while the multiple non-transitory computer-readable storage media collectively store all of the code. Further, in some examples, the executable instructions are executed such that different instructions are executed by different processors. As an illustrative example, a non-transitory computer-readable storage medium may store instructions. A main CPU may execute some of the instructions and a graphics processor unit may execute other of the instructions. Generally, different components of a computer system may have separate processors and different processors may execute different subsets of the instructions.

Accordingly, in some examples, computer systems are configured to implement one or more services that singly or collectively perform operations of processes described herein. Such computer systems may, for instance, be configured with applicable hardware and/or software that enable the performance of the operations. Further, computer systems that implement various embodiments of the present disclosure may, in some examples, be single devices and, in other examples, be distributed computer systems comprising multiple devices that operate differently such that the distributed computer system performs the operations described herein and such that a single device may not perform all operations.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A non-transitory computer-readable storage medium having stored thereon executable instructions that, as a result of being executed by one or more processors of a computer system, cause the computer system to at least:
   obtain a set of sensor data from a belt worn by a subject, the sensor data describing a force applied to the belt;
   process the sensor data to identify a set of activities performed by the subject;
   generate a measure based at least in part on the set of activities;
   cause the measure to be displayed;
   determine, based at least in part on information obtained from the force sensor and the orientation sensor, that a lifting operation was performed by the subject;
   determine, based, at least in part on information obtained from the altimeter, that the subject is working from heights; and
   determine, based at least in part on information obtained from the global positioning sensor, that the subject is driving;
   wherein the belt includes;
      a force sensor that, indicates an amount of tension on the belt;
      an orientation sensor that indicates a posture of the subject;
      a global positioning sensor that tracks the location of the subject over time;
      an altimeter that helps indicate the height of the subject above the grounds.

2. The non-transitory computer-readable storage medium of claim 1, wherein:
   the belt includes an accelerometer; and
   the executable instructions further comprise instructions that, as a result of being executed by the one or more processors, cause the computer system to detect, based at least in part on information generated by the accelerometer, an aggressive driving event.

3. The non-transitory computer-readable storage medium of claim 2, wherein the executable instructions further comprise instructions that, as a result of being executed by the one or more processors, cause the computer system to detect, based at least in part on information generated by the accelerometer, that the subject has fallen.

4. The non-transitory computer-readable storage medium of claim 1, wherein the executable instructions further comprise instructions that, as a result of being executed by the one or more processors, cause the computer system to use tension on the belt as a proxy for estimating a lifting force exerted by the subject.

\* \* \* \* \*